US007588910B2

(12) United States Patent
Matsuoka et al.

(10) Patent No.: US 7,588,910 B2
(45) Date of Patent: Sep. 15, 2009

(54) HEMOGLOBIN A1C DETERMINATION METHOD, ENZYME TO BE USED THEREFOR, AND PRODUCTION METHOD THEREOF

(75) Inventors: Takeshi Matsuoka, Shizuoka (JP); Shinji Koga, Shizuoka (JP); Takuji Kouzuma, Shizuoka (JP); Issei Yoshioka, Shizuoka (JP); Atsuhisa Nishimura, Aichi (JP); Homare Itou, Aichi (JP); Toshihiko Kumazawa, Aichi (JP); Takashi Kuroyanagi, Aichi (JP)

(73) Assignees: Asahi Kasei Pharma Corporation, Tokyo (JP); Ichibiki Co., Ltd., Aichi (JP)

( * ) Notice: Subject to any disclaimer, the term of this patent is extended or adjusted under 35 U.S.C. 154(b) by 182 days.

(21) Appl. No.: 10/557,892

(22) PCT Filed: May 21, 2004

(86) PCT No.: PCT/JP2004/007341

§ 371 (c)(1),
(2), (4) Date: Nov. 18, 2005

(87) PCT Pub. No.: WO2004/104203

PCT Pub. Date: Dec. 2, 2004

(65) Prior Publication Data

US 2008/0113381 A1 May 15, 2008

(30) Foreign Application Priority Data

May 21, 2003 (JP) ............................ 2003-143966
Mar. 5, 2004 (JP) ............................ 2004-063100

(51) Int. Cl.
*C12Q 1/26* (2006.01)
*C12Q 1/37* (2006.01)
(52) U.S. Cl. ........................... 435/23; 435/25; 435/212; 435/219; 435/220
(58) Field of Classification Search ................... 435/23, 435/25, 220, 212, 219
See application file for complete search history.

(56) References Cited

U.S. PATENT DOCUMENTS

| | | | |
|---|---|---|---|
| 5,387,109 | A | 2/1995 | Ishikawa et al. |
| 5,824,527 | A | 10/1998 | Kato et al. |
| 6,033,867 | A | 3/2000 | Kato et al. |
| 6,797,503 | B1 | 9/2004 | Ishimaru et al. |
| 2003/0162242 | A1 | 8/2003 | Yonehara |
| 2003/0186346 | A1 | 10/2003 | Yagi et al. |

FOREIGN PATENT DOCUMENTS

| | | |
|---|---|---|
| EP | 0678576 | 10/1995 |
| EP | 1176191 | 1/2002 |
| EP | 1223224 | 7/2002 |
| EP | 1291416 | 3/2003 |
| JP | 61-280297 | 12/1986 |
| JP | 2000-245454 | 9/2000 |
| JP | 2000-300294 | 10/2000 |
| JP | 2000-300924 | 10/2000 |
| JP | 2001-054398 | 2/2001 |
| JP | 2001-057897 | 3/2001 |
| JP | 2001-204495 | 7/2001 |
| JP | 2002-315600 | 10/2002 |
| WO | 97/13872 | 4/1997 |
| WO | 97/21818 | 6/1997 |
| WO | 2005/028660 | 3/2005 |
| WO | 2005/049857 | 6/2005 |

OTHER PUBLICATIONS

English Language Abstract of JP 2000-300294.
English Language Abstract of W.I.P.O. 97/21818.
Cascon, A. et al.: "A major secreted elastase is essential for pathogenicity of *Aeromonas hydrophila*." Infection and Immunity vol. 68, No. 6, pp. 3233-3241 (2000).
Hase, C.C. et al.: "Cloning nucleotide sequence of the *Vibrio Cholerae* hemagglutin/protease (HA/protease) gene and construction of an HA/Protease-negative strain." Journal of Bacteriology, vol. 173, No. 11, pp. 3311-3317 (1991.
Database EMBL Jul. 15, 1999, "Achromolysin (EC 3.4.24.-) (Fragments)", XP002378424, retrievedd from EBI Database accession No. P81730.
Stenn, K.S. et al.: "Dispase, a neutral protease from *Bacillus polymyxa*, is a powerful fibronectinase and type IV collagenase." Journal of Investigative Dermatology, vol. 93, No. 2, pp. 287-290 (1991).
Takewa, S. et al.: "Proteases involved in generation of [beta]- and [alpha]-amylases from a large amylase precursor in *Bacillus polymyxa*". Journal of Bacteriology, vol. 173, No. 21, pp. 6820-6825 (1991).
Pasternack, R. et al.: "Bacterial pro-transglutaminase from Streptoverticillium mobarense". European Journal of Biochemistry, vol. 257, pp. 570-576, (1998).
Yoshida, N. et al.: "Primary structures of fungal fructosyl amino acid oxidases and their application to the measurement of glycated proteins." European Journal of Biochemistry, vol. 242, No. 3, pp. 499-505 (1996).

(Continued)

Primary Examiner—Tekchand Saidha
(74) Attorney, Agent, or Firm—Greenblum and Bernstein P.L.C.

(57) ABSTRACT

There is provided a method for specifically determining a glycated β-chain N-terminal of glycated hemoglobin using enzymes without a separation operation, and a determination reagent kit therefor. A protease that cleaves a glycated amino acid and/or a glycated peptide from a glycated β-chain N-terminal without substantially cleaving a glycated amino acid or a glycated peptide from a glycated α-chain N-terminal of glycated hemoglobin or a fragment thereof is screened. The method of specifically determining a glycated β-chain N-terminal of glycated hemoglobin and the determination reagent kit are provided by using the protease obtained by the screening method. According to the present invention, a glycated β-chain N-terminal of glycated hemoglobin can specifically be determined without a separation operation.

3 Claims, 10 Drawing Sheets

OTHER PUBLICATIONS

Sakurabayashi, I. et al.: "New enzymatic assay for glycohemoglobin." Clinical Chemistry, vol. 49, No. 2, pp. 269-274 (2003).

Jeppsson, J.-0. et al.: "Approved IFCC reference method for the measurement of $HbA_{1c}$ in human blood." Clinical Chemistry and Laboratory Medicine, vol. 40, No. 1, pp. 78-89 (2002).

Hirokawa, K. et al.: "Distribution and properties of novel deglycating enzymes for fructosyl peptide in fungi." Archives of Microbiology, vol. 180, No. 3, pp. 271-231 (2003).

Hirokawa, K. et al.: "Enzymes used for the determination of $HbA_{1c}$." FEMS Microbiology Letters, vol. 235, No. 1; pp. 157-162 (2004).

Hirokawa, K. et al.: "An enzymatic method for the determination of hemoglobin $A_{1c}$." Biotechnology Letters, vol. 27, No. 14, pp. 963-968 (2005).

English Language Abstract of W.I.P.O. 97/13872.

English Language Abstract of JP 2001-057897.

English Language Abstract of JP 61-280297.

English Language Abstract of JP 2000-245454.

English Language Abstract of W.I.P.O. 2005/028660.

English Language Abstract of W.I.P.O. 2005/049857.

English Language Abstract of JP 2001-054398.

English Language Abstract of JP 2001-204495.

Figure 1

```
NV   1:MTTPRKETTVLIIGGGGTIGSSTALHLLRAGYTPSNITVLDTYPIPSAQSAGNDLNKIMG  60
CS   1:MTSNRADTRVIVVGGGGTIGSSTALHLVRSGYAPANITVLDTFEIPSAQSAGHDLNKIMG  60
CC   1:MAPSRANTSVIVVGGGGTIGSSTALHLVRSGYTPSNITVLDTYPIPSAQSAGNDLNKIMG  60
ET   1:MAHSRASTKVVVVGGGGTIGSSTALHLIRSGYTPSNITVLDVYKTPSLQSAGHDLNKIMG  60
       *  *. * *  ..************ *.**.*.******.. .**.**** *******

NV  61:IRLRNKVDLQLSLEARDMWRNDALFRPFFHNTGRLDCESSAEGVEGLRREYQKLVEAGVG 120
CS  61:IRLRNKVDLQMSLEARQMWKEDELFQPFFHNTGRMDCEHTPEGIEDLKKQYQALHDAGAG 120
CC  61:IRLRNKVDLQLSLEARQMWREDDLFKEYFHNTGRLDCAHGEEGLADLRQAYQALLDANAG 120
ET  61:IRLRNGPDLQLSLESLDMWQNDELFKPFFHQVGMIDCSSSKEGIENLRRKYQTLLDAGIG 120
       *****..***.***.. ** * **..**..*. **      **. *. ** * .*. *

NV 121:LEETHEWLDSEEAILEKAPLLQREEIEGWKAIWSEEGGWLAAAKAINAIGEELQRQGVRF 180
CS 121:LEKTHAWLDNEDEILSKMPLLQRDQIQGWKAIWSQDGGWLAAAKAINAIGQFLKERGVKF 180
CC 121:LEETTEWLDSEDEILKKMPLLDREQIKGWKAVYSQDGGWLAAAKAINAIGEYLRDQGVKF 180
ET 121:LEKTNVWLESEDEILAKAPNFTREQVKGWKGLFCTDGGWLAAAKAINAIGIFLQDKGVKF 180
       ** * **..*..** * *..  *... ***.  . .************ *   **.*

NV 181:GFGGAGSFKRPLFADDGTTCIGVETVDGTQYHADKVVLAAGAWSPALVDLEEQCCSKAWV 240
CS 181:GFGGAGSFKQPLFDDEGTTCIGVETADGTKYYADKVVLAAGAWSPTLVDLEDQCCSKAWV 240
CC 181:GFGGAGSFKQPLLAEGV—CIGVETVDGTRYYADKVVLAAGAWSPVLVDLEDQCVSKAWV 238
ET 181:GFGGAGTFQQPLFAADGKTCIGLETTDGTKYFADKVVLAAGAWSPTLVDLEDQCVSKAWV 240
       ******.*..**..    . .***.** *** * ************* *****.** *****

NV 241:YAHMQLTPEEAAVYKGCPVVYHGDVGFFFEPNENGVIKVCDEFPGFTRFKQHQPYGAPAP 300
CS 241:YAHIQLTPEEAAEYKGVPVVYNGEFGFFFEPNEFGVIKVCDEFPGFSRFKEHQPYGAPSP 300
CC 239:YAHIQLTPEEAAEYKNVPVVYNGDVGFFFEPDEHGVIKVCDEFPGFTRFKQHQPYGAKAP 298
ET 241:FAHIQLTPKEADAYKNVPVVYDGEYGFFFEPNEYGVIKVCDEFPGFSRFKLHQPYGAASP 300
       .**.****.**. ** .****  *    ******.*  ************ *** ****** *

NV 301:KPVSVPRSHAKHPTDTYPDASEESIKRAVSTFLPRFKDKPLFNRALCWCTDTADSALLIC 360
CS 301:KHISVPRSHAKHPTDTYPDASEVSIKKAIATFLPRFQDKELFNRALCWCTDTADAALLMC 360
CC 299:KRISVPRSAAKHPTDTYPDASEKSIRKAIATFLPKFTEKELFNRHLCWCTDTADAALLMC 358
ET 301:KMISVPRSHAKHPTDTYPDASEVTIRKAIARFLPEFKDKELFNRTMCWCTDTADNLLIC 360
       * .*****.************ .* .*...*** * .*.**** .********..** *

NV 361:EHPRWKNFILATGDSGHSFKLLPIIGKHVVELVEGRLADDLAEAWRWRPGQGDARKSIRA 420
CS 361:EHPKWKNFILATGDSGHSFKILPNVGKHVVELIEGRLPEEMAYQWRWRPGGD-ALKSRRA 419
CC 359:EHPEWKNFVLATGDSGHTFKLLPNIGKHVVELLEGTLAEDLAHAWRWRPGTGDALKSRRA 418
ET 361:EHPKWKNFILATGDSGHSFKLLPNIGKHVVELLEGSLSQEMAGAWRWRPGGDALRSR-RG 419
       *** ****.********.**.****.**.*******. ** *    * .******  ... *.

NV 421:APAKDLADMPGWKHDQDSESR- 441      NV:Neocosmospora_vasinfecta
CS 420:APPKDLADMPGWKHDP——KL  437      CS:Coniochaeta_sp.
CC 419:APAKDLADMPGWKHDDVVKSKL 440      CC:Curvralia_cravatae
ET 420:APAKDLAEMPGWKHDA——HL—  437      ET:Eupenicillium_terrenum
       **.****.*******
```

Note: The described base numbers are counted from the position 471, which is considered as the first position, in the base sequence according to SEQ ID NO: 1.

HEMOGLOBIN A1C DETERMINATION METHOD, ENZYME TO BE USED
THEREFOR, AND PRODUCTION METHOD
THEREOF

TECHNICAL FIELD

The present invention relates to a method of specifically determining a glycated β-chain N-terminal of glycated hemoglobin using enzymes without a separation operation, a determination reagent kit, a protease that may be used for the specific determination, a production method thereof, a screening method thereof, and a ketoamine oxidase that may be used for the specific determination.

BACKGROUND ART

Determining glycated proteins is very important in diagnosing and controlling diabetes. In particular, recent studies on hemoglobin A1c have proved that risk of occurrence and progression of complications is significantly lowered by controlling the level to 7% or less, so that the level is often used as an index that is essential in clinical fields. As a quantification method for hemoglobin A1c, there are generally known electrophoresis, ion-exchange chromatography, affinity chromatography, immunization, and enzymatic methods. However, the electrophoresis and chromatography methods require expensive dedicated devices, and processing speeds thereof are low, so that those methods are inappropriate for clinical examinations to process many samples. Meanwhile, the analysis method of the immunization method is relatively easy and can be performed in a small amount of time, so that the method has rapidly spread in recent years. However, the method is performed using an antigen-antibody reaction, so that it is problematic that the accuracy is not always good due to reproducibility and effects of coexisting substances.

Meanwhile, the enzymatic method has been suggested as a determination method that requires no dedicated device, has a high processing speed, and is highly accurate, easy, and inexpensive (JP-A-08-336386, WO 97/13872, JP-A-2001-95598, JP-A-2000-300294, and Clinical Chemistry 49(2): 269-274 (2003)).

Hemoglobin is glycated at an ε-amino group of intramolecular lysine and at α-amino groups of valine in α- and β-chain N-terminals, but hemoglobin A1c is hemoglobin where an α-amino group of valine in a hemoglobin β-chain N-terminal has been glycated (definition accepted as the international standard in Clinical Chemistry and Laboratory Medicine 40(1): 78-89 (2002)). Therefore, in order to specifically determine a glycated β-chain N-terminal of glycated hemoglobin without a separation operation using a protease and a ketoamine oxidase, it is believed that specificity is required in enzymatic reactions of either or both of a protease and a ketoamine oxidase.

Specifically, glycated hemoglobin has three glycated sites, that is, intramolecular lysine, α-chain N-terminal, and β-chain N-terminal, so that in order to determine only the glycated β-chain N-terminal, it is necessary that those enzymes be combined according to specificity as below.

That is, in the case where proteases and ketoamine oxidases are classified into (P1) to (P4) and (K1) to (K5), respectively, it is necessary that those enzymes be combined as below: <(P1) and (K1) or (K2) or (K3) or (K4)>, <(P2) and (K1) or (K3)>, <(P3) and (K1) or (K2)>, <(P4) and (K1)>, <(P3) and (K5) and (K3)>, and <(P3) and (K5) and (K4)>.

The properties of the respective classified enzymes are as follows.

(P1) cleaves a glycated amino acid and/or a glycated peptide only from a glycated β-chain N-terminal of glycated hemoglobin, (P2) cleaves a glycated amino acid and/or a glycated peptide only from glycated α- and β-chain N-terminals of glycated hemoglobin, (P3) cleaves a glycated amino acid and/or a glycated peptide only from a glycated β-chain N-terminal of glycated hemoglobin and a site including a intramolecular lysine, (P4) cleaves a glycated amino acid and/or a glycated peptide from a glycated α- and β-chain N-terminals of glycated hemoglobin and a site including a intramolecular lysine, (K1) reacts only with a glycated amino acid and/or a glycated peptide derived from a glycated β-chain N-terminal of glycated amino acids and/or glycated peptides cleaved from glycated hemoglobin by a protease to be used in combination, (K2) reacts only with a glycated amino acid and/or a glycated peptide derived from glycated α- and β-chain N-terminals of glycated amino acids and/or glycated peptides cleaved from glycated hemoglobin by a protease to be used in combination, (K3) reacts only with a glycated amino acid and/or a glycated peptide derived from a glycated β-chain N-terminal and from a site including intramolecular lysine of glycated amino acids and/or glycated peptides cleaved from glycated hemoglobin by a protease to be used in combination, (K4) reacts with a glycated amino acid and/or a glycated peptide derived from glycated α- and β-chain N-terminals and from a site including intramolecular lysine that have been cleaved from glycated hemoglobin by a protease to be used in combination, and (K5) reacts with a glycated amino acid and/or a glycated peptide from a site including intramolecular lysine without reacting with a glycated amino acid and/or a glycated peptide derived from a glycated β-chain N-terminal of glycated amino acids and/or glycated peptides cleaved from glycated hemoglobin by a protease to be used in combination.

However, as proteases for generating a glycated amino acid and/or a glycated peptide, which serves as a substrate for a ketoamine oxidase, from glycated hemoglobin or a fragment thereof, there have already been known proteases described in JP-A-08-336386, WO 97/13872, JP-A-2001-95598, JP-A-2001-57897, WO 00/50579, WO 00/61732, Clinical Chemistry 49(2): 269-274 (2003), etc. However, there is no description about specificity to cleave a glycated amino acid and/or a glycated peptide from a glycated β-chain N-terminal without substantially cleaving a glycated amino acid or a glycated peptide from a glycated α-chain N-terminal from glycated hemoglobin or a fragment thereof.

Meanwhile, an angiotensin-converting enzyme described in JP-A-2000-300294 is also estimated to react with a β-chain N-terminal glycated tripeptide from its known substrate specificity, but there is no specific description that shows cleavage of a glycated amino acid and/or a glycated peptide from a glycated β-chain N-terminal without substantially cleaving a glycated amino acid and/or a glycated peptide from a glycated α-chain N-terminal of glycated hemoglobin or a fragment thereof, for example, there is no description that shows results of quantification of specificity of the angiotensin-converting enzyme to an α-chain N-terminal glycated tripeptide or to a β-chain N-terminal glycated tripeptide.

Meanwhile, in JP-A-2000-300294, there is no description showing that trypsin, proline-specific endoprotease, and carboxypeptidase P, which were used in generating a β-chain N-terminal glycated tripeptide from glycated hemoglobin, generate no glycated amino acid or no glycated peptide derived from a site including intramolecular lysine and a glycated α-chain N-terminal.

Furthermore, the inventors of the present invention have confirmed that an angiotensin-converting enzyme hardly cleaves fructosyl valine from a β-chain N-terminal glycated tripeptide under a general reaction condition, so that the angiotensin-converting enzyme is not considered to be a protease that cleaves a glycated amino acid and/or a glycated peptide from a glycated β-chain N-terminal without substantially cleaving a glycated amino acid or a glycated peptide from an α-chain N-terminal.

As described above, there has not been known a protease and a reaction condition for a protease that cleave a glycated amino acid and/or a glycated peptide from a glycated β-chain N-terminal without substantially cleaving a glycated amino acid or a glycated peptide from a glycated α-chain N-terminal of glycated hemoglobin or a fragment thereof, that is, a protease that has the above-described specificity (P1) or (P3) or a reaction condition for a protease that is designed so as to accomplish the above-described specificity (P1) or (P3).

Meanwhile, in general, the following screening method is viewed as a method of screening a protease that cleaves a glycated amino acid and/or a glycated peptide from a glycated β-chain N-terminal without substantially cleaving a glycated amino acid or a glycated peptide from a glycated α-chain N-terminal of glycated hemoglobin or a fragment thereof, that is, a screening method for a protease that has the above-described specificity (P1) or (P3). That is, glycated hemoglobins are divided into hemoglobin where an α-chain N-terminal has been glycated and hemoglobin where a β-chain N-terminal has been glycated, and a protease that selectively cleaves a glycated amino acid and/or a glycated peptide only from the hemoglobin where a β-chain N-terminal has been glycated when using those hemoglobins as substrates is searched using an enzyme (such as a ketoamine oxidase) that reacts with the glycated amino acid and/or the glycated peptide cleaved by the protease, based on coloring. However, the glycation rate of a glycated hemoglobin product existing in nature is low (about 5%). Therefore, the yield in separating hemoglobin where an α-chain N-terminal has been glycated and hemoglobin where a β-chain N-terminal has been glycated was extremely low, and it was difficult to detect the activity of the protease using those substances as substrates because hemoglobin is red. As described above, an easy and effective screening method has never been known.

On the other hand, ketoamine oxidases include the following enzymes.

1) A ketoamine oxidase that is derived from a microorganism belonging to the genus *Fusarium* (JP-A-07-289253), the genus *Gibberella*, the genus *Candida* (JP-A-06-46846), or the genus *Aspergillus* (WO 97/20039) and mainly reacts with ε-1-deoxyfructosyl-L-lysine (hereinafter also referred to as FK) or a peptide including it and fructosyl valine (hereinafter also referred to as FV), 2) a ketoamine oxidase that is derived from a microorganism belonging to the genus *Corynebacterium* (JP-A-61-280297), the genus *Penicillium* (JP-A-08-336386), or the genus *Trichosporon* (JP-A-2000-245454) and mainly reacts with FV. In general, a step for cleaving FV from a hemoglobin β-chain N-terminal glycated peptide using a protease has disadvantages in that the reaction hardly proceeds in general and must be performed using a large amount of enzymes for a long time, so that, in order to overcome such disadvantages, a ketoamine oxidase that reacts also with a glycated peptide cleaved from a hemoglobin β-chain N-terminal glycated peptide by a protease has been required as a ketoamine oxidase to be used in determining hemoglobin A1c. Thus, 3) a mutant ketoamine oxidase derived from *Corynebacterium* JP-A-2001-95598) and a ketoamine oxidase that is derived from a microorganism belonging to the genus *Achaetomiella*, the genus *Achaetomium*, the genus *Thielabia* the genus *Chaetomium*, the genus *Gelasinospora*, the genus *Microascus*, the genus *Coniochaeta*, or the genus *Eupenicillium* (EP 1,291,416) and reacts with 1-deoxyfructosyl-L-valyl-L-histidine (hereinafter also referred to as FVH), which have the above-described property, have been reported in recent years.

However, a ketoamine oxidase belonging to 1) has the property (K4) and a ketoamine oxidase belonging to 2) has the property (K2), but there is no description that they react with FVH. A ketoamine oxidase belonging to 3), even a ketoamine oxidase that is derived from a microorganism belonging to the genus *Eupenicillium* and reacts with FK at the most low rate, reacts with FK at a rate of 9.78% in the case where the reaction with FVH is defined as 100% (EP 1,291, 416). Therefore, it is considered that the ketoamine oxidase sufficiently reacts with a glycated amino acid and/or a glycated peptide from a site including intramolecular lysine cleaved from glycated hemoglobin by a protease, and there is no description about a reaction with a glycated peptide derived from a glycated α-chain N-terminal cleaved from glycated hemoglobin by a protease, for example, 1-deoxyfructosyl-L-valyl-L-leucine (hereinafter also referred to as FVL), so that it is not considered to be a ketoamine oxidase having the property (K1), (K2), or (K3).

As described above, there have not been reported ketoamine oxidases that: have the property (K1); have the property (K2) and reacts with FVH; or have the property (K3).

Meanwhile, in order to prepare ketoamine oxidases that have the property (K1), and have the property (K2) and reacts with FVH, it is considered to perform modification of known ketoamine oxidases by amino acid substitution, deletion, insertion, etc. However, it has not been known which amino acid residue in the primary structure of the enzyme contributes to reduction of a reaction with FK or FZK. Therefore, the activity to FK or ε-1-deoxyfructosyl-(α-benzyloxycarbonyl-L-lysine) (hereinafter also referred to as FZK) cannot be reduced by modification of any ketoamine oxidase gene, i.e., there has not been known preparation of ketoamine oxidases that have the property (K1), and have the property (K2) and reacts with FVH by modification.

Meanwhile, there has not been known reduction of a rate of the activity to FK or FZK compared to that to FVH by regulating a reaction condition for a ketoamine oxidase capable of reacting with FVH.

In order to clearly distinguish and determine glycation of an α-amino group of valine in a β-chain N-terminal existing in glycated hemoglobin using a protease and a ketoamine oxidase, the specificity of the protease and ketoamine oxidase must be combined as described above. However, in JP-A-08-336386, WO 97/13872, JP-A-2001-95598, and Clinical Chemistry 49(2): 269-274 (2003), there is no description about specific determination of a glycated β-chain N-terminal of hemoglobin, and there is only a description that the value that was obtained or may be obtained by the HPLC method significantly correlates with the determined value obtained by the disclosed enzymatic method. Moreover, there is no mention about specificity of the used protease and ketoamine oxidase, and a glycated amino acid and/or a glycated peptide cleaved simply by degrading glycated hemoglobin by a protease is detected by a ketoamine oxidase, so that it is considered that there was detected a mixture of hemoglobin where an ε-amino group of intramolecular lysine and α-amino groups of valine in α- and β-chain N-terminals have been glycated. Furthermore, in examples in JP-A-2001-95598, glycated hemoglobin was determined using a protease and a ketoamine oxidase that reacts with FVH. However, centrifugation was performed as an operation, and there is no description that the determination can be performed without a separation operation.

JP-A-2000-300294 suggests an enzymatic method of specifically determining only hemoglobin in which an α-amino group of valine in hemoglobin β-chain N-terminals has been glycated. In this method, sequential processing was performed by a protease capable of cleaving the carboxyl group side of leucine at the third position from a hemoglobin β-chain N-terminal and then by a protease capable of cleaving His-Leu from fructosyl-Val-His-Leu, to thereby generate fructosyl valine, and the amount of glycation of an α-amino groups of valine in a hemoglobin β-chain N-terminal was specifically determined. However, this method have the following disadvantages: it requires two stages of protease reactions; it is difficult to strictly control the protease reaction for cleaving the carboxyl group side of leucine at the third position from a hemoglobin β-chain N-terminal in the first stage; and a reaction of the step for cleaving an α-glycated amino acid from a hemoglobin β-chain N-terminal glycated peptide in the second stage hardly proceeds in general and must be performed using a large amount of enzymes for a long time. Moreover, in the method shown in examples, a cumbersome separation operation (ultrafiltration) was performed twice, and there is no description that the method of the present application enables specific determination of a glycated β-chain N-terminal of glycated hemoglobin without a separation operation.

EP 1,291,416 suggests a method of determining a glycated protein such as hemoglobin A1c with an oxidase capable of reacting with FVH to be released by a protease such as Molsin, AO-protease, Peptidase (available from Kikkoman Corporation), carboxypeptidase Y, or Protin P (available from Daiwa Kasei K.K.). The description further suggests, in the case where FK generated by a protease is problematic, determination by an oxidase capable of reacting with FVH after elimination of FK by a fructosyl amine oxidase that reacts with FK, or determination using an oxidase that reacts FVH and hardly reacts with FK. However, there is no mention about distinction between a glycated amino acid and/or a glycated peptide derived from a glycated α-chain N-terminal of glycated hemoglobin, and there are not demonstrated examples on determination of a glycated β-chain N-terminal of glycated hemoglobin by the suggested method. In addition, there is no description that the suggested method can be performed without a separation operation.

Although the above-described determination methods relating to glycated hemoglobin were known, there have not been known a method and a reagent kit for specifically determining a glycated β-chain N-terminal of glycated hemoglobin using enzymes without a separation operation.

SUMMARY OF THE INVENTION

An object of the present invention is to provide a method capable of specifically determining only a glycated β-chain N-terminal of glycated hemoglobin without a separation operation, a determination reagent kit, a protease that can be used for the specific determination, a production method thereof, a screening method thereof, and a ketoamine oxidase that can be used for the specific determination.

The inventors of the present invention have made extensive studies and as a result, firstly, we have invented a method of screening a protease that cleaves a glycated amino acid and/or a glycated peptide in a β-chain N-terminal without substantially cleaving a glycated amino acid or a glycated peptide in an α-chain N-terminal of glycated hemoglobin or a fragment thereof. That is, we have invented a method of detecting the activity of a protease that cleaves a glycated amino acid and/or a glycated peptide, which serves as a substrate for a ketoamine oxidase, from a glycated β-chain N-terminal without substantially cleaving a glycated amino acid or a glycated peptide, which serves as a substrate for a ketoamine oxidase, from a glycated α-chain N-terminal of glycated hemoglobin by using glycated peptides, which serve as substrates for a protease, existing in the α-chain N-terminal and β-chain N-terminal of glycated hemoglobin.

Next, the invented screening method is used for screening of a wide variety of proteases that cleave a glycated amino acid and/or a glycated peptide, which serves as a substrate for a ketoamine oxidase, from a β-chain N-terminal glycated pentapeptide without substantially cleaving a glycated amino acid or a glycated peptide, which serves as a substrate for a ketoamine oxidase, from an α-chain N-terminal glycated pentapeptide. As a result, it has been found out that the protease reaction of interest occurs in a commercially-available protease preparation such as a neutral proteinase derived from *Bacillus* sp. (manufactured by Toyobo Co., Ltd.) or in a protease produced by a bacterium such as *Bacillus* sp., *Aeromonas hydrophila*, or *Lysobacter enzymogenes*.

In addition, of those proteases, the proteases produced by *Aeromonas hydrophila* and *Lysobacter enzymogenes* have found to have homology to known elastases. Conventionally, it is known that an elastase has substrate specificity and is known as an enzyme that cleaves a peptide bond on the C-terminal side of leucine, isoleucine, valine, or alanine. The present invention revealed for the first time that the elastase cleaves a peptide bond not on the C-terminal side but on the N-terminal side of leucine in 1-deoxyfructosyl-L-valyl-L-histidyl-L-leucyl-L-threonyl-L-proline (SEQ ID NO: 36) (hereinafter also referred to as hemoglobin β-chain N-terminal glycated pentapeptide) to release FVH.

Next, there has been completed a method of specifically determining a glycated β-chain N-terminal of glycated hemoglobin or a fragment thereof using enzymes without a separation operation by previously eliminating FK and/or a glycated peptide including FK by a ketoamine oxidase that does not react with a glycated peptide derived from a glycated β-chain N-terminal and reacts with FK or a glycated peptide including FK, in the case where the protease of interest cleaves not only a glycated amino acid and/or a glycated peptide from a glycated β-chain N-terminal but also FK and/or a glycated peptide including FK from glycated hemoglobin or a fragment thereof without cleaving a glycated amino acid or a glycated peptide from a glycated α-chain N-terminal of glycated hemoglobin or a fragment thereof.

Moreover, there has been found out a reaction condition capable of significantly reducing reactivity to FZK of a ketoamine oxidase in the case where the protease cleaves not only a glycated amino acid and/or a glycated peptide from a glycated β-chain N-terminal but also FK and/or a peptide including FK from glycated hemoglobin or a fragment thereof, without cleaving a glycated amino acid or a glycated peptide from a glycated α-chain N-terminal of glycated hemoglobin or a fragment thereof. Meanwhile, preparation and use of a novel ketoamine oxidase having high specificity, which reacts with FZK at a rate of 5% or less in the case where the reaction with FVH is defined as 100%, enabled specific determination of only a glycated amino acid and/or a glycated peptide cleaved from a glycated β-chain N-terminal. That is, the inventors of the present invention have discovered that substitution of amino acids at position 58 and 62 in a ketoamine oxidase gene derived from *Curvularia clavata* contributes to reduction of reactivity to FZK. Preparation and use of the oxidase based on such fact led to completion of a method of specifically determining a glycated β-chain N-terminal of glycated hemoglobin or a fragment thereof using enzymes without a separation operation.

Furthermore, the following reaction conditions for the protease of interest for degradation of glycated hemoglobin or a fragment thereof were found out:

i) a condition not to cleave FK and/or a glycated peptide including FK, that can react with a ketoamine oxidase to be used in combination with the protease of interest;

ii) a condition not to cleave a glycated amino acid or a glycated peptide that is derived from a glycated α-chain N-terminal and can react with a keto amine oxidase to be used in combination with the protease of interest; and iii) a condition to cleave a glycated amino acid or a glycated peptide that is derived from a glycated β-chain N-terminal and can react with a ketoamine oxidase to be used in combination with the protease of interest. As the results, the inventors of the present invention have completed a method of specifically determining a glycated β-chain N-terminal of glycated hemoglobin or a fragment thereof using enzymes without separation operation.

That is, the present invention has the following configurations.

(1) A protease which cleaves a glycated amino acid and/or a glycated peptide from a glycated β-chain N-terminal of glycated hemoglobin without substantially cleaving a glycated amino acid or a glycated peptide from a glycated α-chain N-terminal of glycated hemoglobin.

(2) A protease which cleaves a glycated amino acid and/or a glycated peptide from a fragment including a glycated β-chain N-terminal of glycated hemoglobin without substantially cleaving a glycated amino acid or a glycated peptide from a fragment including a glycated α-chain N-terminal of glycated hemoglobin.

(3) A protease whose reaction to cleave a glycated amino acid or a glycated peptide from a glycated α-chain N-terminal of glycated hemoglobin occurs at 10% or less in the case where a reaction to cleave a glycated amino acid and/or a glycated peptide from a glycated β-chain N-terminal of glycated hemoglobin is defined as 100%.

(4) A protease according to any one of the above items (1) to (3), in which a glycated peptide cleaved from a glycated β-chain N-terminal of glycated hemoglobin or a fragment including a glycated β-chain N-terminal of glycated hemoglobin is 1-deoxyfructosyl-L-valyl-L-histidine.

(5) A protease according to any one of the above items (1) to (4), in which the glycated amino acid and glycated peptide that are not substantially cleaved from the glycated α-chain N-terminal of glycated hemoglobin or the fragment including the glycated α-chain N-terminal of glycated hemoglobin are 1-deoxyfructosyl-L-valine and 1-deoxyfructosyl-L-valyl-L-leucine, respectively.

(6) A protease according to any one of the above items (1) to (5), which is a protease derived from a bacterium belonging to the genus Lysobacter.

(7) A protease according to any one of the above items (1) to (5), which is a protease derived from Bacillus sp. ASP-842 (FERM BP-08641) or Aeromonas hydrophila NBRC 3820.

(8) A protease according to any one of the above items (1) to (7), which is a metalloprotease, neutral protease, or elastase.

(9) An elastase which cuts a peptide bond on the N-terminal side of leucine in a protein or peptide.

(10) A Lysobacter enzymogenes YK-366 (FERM BP-10010) strain.

(11) A Bacillus sp. ASP-842 (FERM BP-08641) strain.

(12) A method of producing a protease according to the above item (6), which includes the following steps (a) and (b):

(a) culturing a bacterium belonging to the genus Lysobacter in a culture solution; and (b) extracting a protease from the culture solution.

(13) A method of producing the protease according to the above item (7), which includes the following steps (a) and (b):

(a) culturing Bacillus sp. ASP-842 (FERM BP-08641) or Aeromonas hydrophila NBRC 3820 in a culture solution; and (b) extracting a protease from the culture solution.

(14) A ketoamine oxidase which has the following property (A):

(A) the reactivity to ε-1-deoxyfructosyl-(α-benzyloxycarbonyl-L-lysine) is 5% or less than that to 1-deoxyfructosyl-L-valyl-L-histidine.

(15) A ketoamine oxidase according to the above item (14), which further has the following properties (B) and (C):

(B) consisting of amino acids having at least 75% homology to the amino acid sequence described in SEQ ID NO: 1; and (C) at least an amino acid at position 58 or 62 in the amino acid sequence described in SEQ ID NO: 1 being substituted by another amino acid.

(16) A ketoamine oxidase according to the above item (15), in which in the amino acid substitution described in (C), the amino acid at position 58 is substituted by valine, threonine, asparagine, cysteine, serine, or alanine; and the amino acid at position 62 is substituted by histidine.

(17) A gene which encodes an amino acid sequence of a ketoamine oxidase according to any one of the above items (14) to (16).

(18) A ketoamine oxidase-expression vector which contains a gene according to the above item (17).

(19) A host cell which contains an expression vector according to the above item (18).

(20) A method of specifically determining a glycated β-chain N-terminal of glycated hemoglobin using enzymes without a separation operation.

(21) A determination method according to the above item (20), in which the enzymes include a protease (i).

(22) A determination method according to the above item (21), in which the enzymes further include a ketoamine oxidase (ii).

(23) A determination method according to the above item (22), in which the N-terminal is specifically determined via the following reaction steps (iii) and/or (iv):

(iii) a reaction step wherein the protease (i) cleaves a glycated amino acid and/or a glycated peptide from a glycated β-chain N-terminal of glycated hemoglobin without substantially cleaving ε-1-deoxyfructosyl-L-lysine and/or a glycated peptide including ε-1-deoxyfructosyl-L-lysine, which the ketoamine oxidase (ii) reacts with, from glycated hemoglobin; and (iv) a reaction step in which the reactivity of the ketoamine oxidase (ii) to ε-1-deoxyfructosyl-(α-benzyloxycarbonyl-L-lysine) is 30% or less compared with that to 1-deoxyfructosyl-L-valyl-L-histidine.

(24) A determination method according to the above item (23), in which the reaction step (iii) is performed under a reaction condition of pH 5.0 to 6.0.

(25) A determination method according to the above item (23) or (24), in which the reaction step (iv) is performed under a reaction condition of pH 5.5 to 6.5.

(26) A determination method according to any one of the above items (21) to (25), in which the protease (i) is a protease according to any one of the above items (1) to (8).

(27) A determination method according to any one of the above items (22) to (26), in which the ketoamine oxidase (ii) is a ketoamine oxidase that reacts with a glycated amino acid and/or a glycated peptide each cleaved from a glycated β-chain N-terminal of glycated hemoglobin by a protease.

(28) A determination method according to the above item (27), in which the ketoamine oxidase is derived from a bacterium belonging to the genus *Curvularia*.

(29) A determination method according to any one of the above items (22) to (28), in which the ketoamine oxidase (ii) includes the following two kinds of ketoamine oxidases (a) and (b):

(a) a ketoamine oxidase that reacts with a glycated amino acid and/or a glycated peptide each cleaved from a glycated β-chain N-terminal of glycated hemoglobin by a protease; and (b) a ketoamine oxidase that reacts with ε-1-deoxyfructosyl-L-lysine and/or a glycated peptide including ε-1-deoxyfructosyl-L-lysine without substantially reacting with a glycated amino acid and/or a glycated peptide each cleaved from a glycated β-chain N-terminal of glycated hemoglobin by a protease.

(30) A determination method according to the above item (29), in which the ketoamine oxidase (a) is derived from a bacterium belonging to the genus *Curvularia* and/or the ketoamine oxidase (b) is derived from a bacterium belonging to the genus *Fusarium*.

(31) A determination method according to any one of the above items (22) to (26), in which the ketoamine oxidase (ii) is a ketoamine oxidase according to any one of the above items (14) to (16).

(32) A method of screening a protease that cleaves a glycated amino acid and/or a glycated peptide from a glycated β-chain N-terminal without substantially cleaving a glycated amino acid or a glycated peptide from a glycated α-chain N-terminal of glycated hemoglobin or a fragment thereof, in which a hemoglobin α-chain N-terminal glycated peptide having a length of 3 amino acids to 20 amino acids and a hemoglobin β-chain N-terminal glycated peptide having a length of 3 amino acids to 20 amino acids are used.

(33) A screening method according to the above item (32), in which the hemoglobin α-chain N-terminal glycated peptide and hemoglobin β-chain N-terminal glycated peptide have a length of 5 amino acids.

(34) A reagent kit for specifically determining a glycated β-chain N-terminal of glycated hemoglobin without a separation operation, which includes the following (i) and (ii):

(i) a protease; and (ii) a ketoamine oxidase according to the above item (14).

According to the present invention, there are provided a method capable of specifically determining only a glycated β-chain N-terminal of glycated hemoglobin without a separation operation, a determination reagent kit, a protease to be used for the specific determination, a production method or a screening method for the protease, and a ketoamine oxidase that can be used for the specific determination.

BRIEF DESCRIPTION OF THE DRAWINGS

FIG. 1 shows the homology in amino acid sequences of ketoamine oxidases (SEQ ID NOS 33, 34, 32 & 35, disclosed respectively in order of appearance).

BEST MODE FOR CARRYING OUT THE INVENTION

Figure 2:
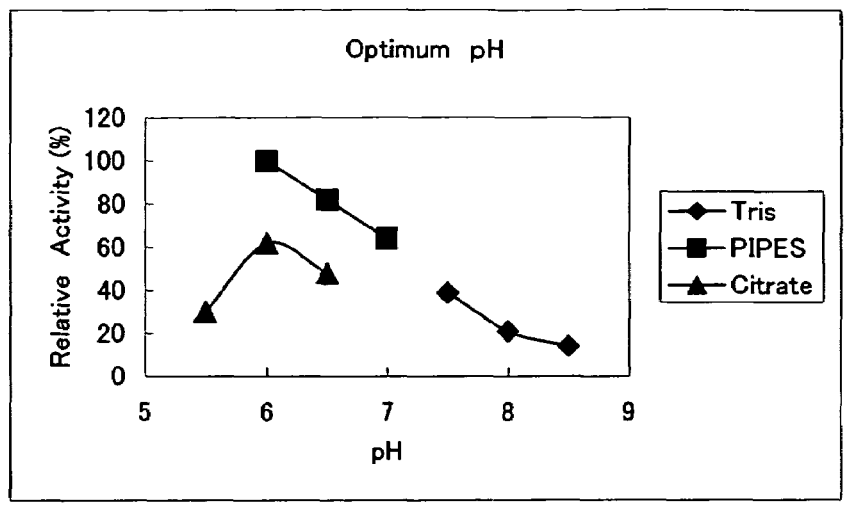
FIG. 2 shows the optimum pH for a protease derived from *Bacillus* sp. ASP 842.

Hereinafter, configurations and preferred modes of the present invention will be described in more detail.

<Amadori Compound>

The term "Amadori compound" in the present invention refers to a compound having a ketoamine structure represented by a general formula —(CO)—CHR—NH— (R represents a hydrogen atom or a hydroxyl group), which is generated by a Maillard reaction of a compound having an amino group such as a protein and a compound having an aldehyde group such as glucose. The Amadori compound includes: a glycated protein such as glycated hemoglobin or glycated albumin; a glycated peptide generated by glycation of a peptide; etc.

<Glycated Hemoglobin>

The term refers to an Amadori compound generated by glycation of hemoglobin by a Maillard reaction, in which each α-amino group of valine in α-chain and β-chain N-terminals or an ε-amino group of intramolecular lysine is considered to be glycated. The fragment of glycated hemoglobin refers to a peptide obtained by degradation of glycated hemoglobin.

<Hemoglobin A1c>

In a definition accepted as the international standard, hemoglobin A1c is believed to be glycated hemoglobin in which an α-amino group of valine in a hemoglobin β-chain N-terminal is glycated (Clinical Chemistry and Laboratory Medicine 36(5): 299-308 (1998)).

<Specifically>

The phrase "specifically determining a glycated β-chain N-terminal of glycated hemoglobin" is used in the case where a value obtained by determination of a glycation level of glycated hemoglobin is derived from glycation of an α-amino group of valine in a hemoglobin β-chain N-terminal at a rate of 80% or more, desirably 90% or more, more desirably 95% or more.

<Glycated Amino Acid and Glycated Peptide>

In the phrase "without a protease substantially cleaving a glycated amino acid or a glycated peptide from a glycated α-chain N-terminal of glycated hemoglobin or a fragment thereof", the term "glycated amino acid" refers to 1-deoxy-fructosyl-L-valine, while the term "glycated peptide" refers to a peptide that has a length of 20 amino acids or less from the α-chain N-terminal of hemoglobin, includes 1-deoxyfructo-syl-L-valine as an N-terminal valine, and is detected by a ketoamine oxidase to be used in combination with a protease. For example, in the case where a ketoamine oxidase derived from Curvularia clavata YH 923 (FERM BP-10009) is used in combination with a protease, the term refers to 1-deoxy-fructosyl-L-valyl-L-leucine.

In the phrase "a protease cleaves a glycated amino acid or a glycated peptide from a glycated β-chain N-terminal of glycated hemoglobin or a fragment thereof", the term "glycated amino acid" refers to 1-deoxyfructosyl-L-valine, while the term "glycated peptide" refers to a peptide that has a length of 20 amino acids or less from the β-chain N-terminal of hemoglobin, includes 1-deoxyfructosyl-L-valine as an N-terminal valine, and is detected by a ketoamine oxidase to be used in combination with a protease. For example, in the case where a ketoamine oxidase derived from Curvularia clavata YH 923 (FERM BP-10009) is used in combination with a protease, the term refers to 1-deoxyfructosyl-L-valyl-L-histidine. In the phrase "a protease cleaves a glycated peptide including ε-1-deoxyfructosyl-L-lysine from glycated hemoglobin", the term "glycated peptide" refers to a glycated peptide having a length of 50 amino acids or less.

Note that, Curvularia clavata YH 923 (FERM BP-10009) has been deposited in International Patent Organism Depositary, National Institute of Advanced Industrial Science and Technology, Tsukuba Central 6, 1-1-1 Higashi, Tsukuba, Ibaraki, Japan on Feb. 12, 2003.

<Substantially>

In a protease reaction, the phrase "cleaving a glycated amino acid and/or a glycated peptide from a glycated β-chain N-terminal without substantially cleaving a glycated amino acid or a glycated peptide from a glycated α-chain N-terminal" refers to the fact that the reactivity to cleave a glycated amino acid or a glycated peptide from a glycated α-chain N-terminal is 10% or less, desirably 1% or less, more desirably 0.1% or less in the case where the reactivity to cleave a glycated amino acid and/or a glycated peptide from a glycated β-chain N-terminal is defined as 100%. Note that the above-described protease reaction is determined by detecting cleaved products using a ketoamine oxidase, preferably a ketoamine oxidase derived from Curvularia clavata YH 923 (FERM BP-10009) or a ketoamine oxidase derived from Fusarium oxysporum (manufactured by Asahi Kasei Pharma Corporation).

In a ketoamine oxidase reaction, the phrase "reacting with an ε-glycated amino acid without substantially reacting with a glycated amino acid and/or a glycated peptide cleaved from a glycated β-chain N-terminal by a protease" refers to the fact that the reactivity to a glycated amino acid and/or a glycated peptide cleaved from a glycated β-chain N-terminal by a protease is 10% or less, preferably 8% or less, more preferably 1% or less, most preferably 0.1% or less in the case where the reactivity to an ε-glycated amino acid is defined as 100%. Meanwhile, in a ketoamine oxidase reaction, the phrase "reacting with a glycated amino acid and/or a glycated peptide cleaved from a glycated β-chain N-terminal by a protease without substantially reacting with an ε-glycated amino acid" refers to the fact that the reactivity to an ε-glycated amino acid is 8% or less, desirably 1% or less, more desirably 0.1% or less in the case where the reactivity to a glycated amino acid and/or a glycated peptide cleaved from a glycated β-chain N-terminal by a protease is defined as 100%. Note that the ketoamine oxidase reaction is determined by detecting generated hydrogen peroxide.

<Ketoamine Oxidase>

The term refers to an enzyme that reacts with a compound having a ketoamine structure to generate hydrogen peroxide, which is also known as fructosyl-amine oxidase.

<Ketoamine Oxidase having Reactivity to ε-1-deoxyfructo-syl-(α-benzyloxycarbonyl-L-lysine) of 5% or less Compared with Reactivity to 1-deoxyfructosyl-L-valyl-L-histidine>

The phrase "reactivity of a ketoamine oxidase to ε-1-deoxyfructosyl-(α-benzyloxycarbonyl-L-lysine) (hereinafter also referred to as FZK) is 5% or less compared with that to 1-deoxyfructosyl-L-valyl-L-histidine (hereinafter also referred to as FVH)" refers to the fact that the rate of the reactivity is 5% or less, which is determined by the following steps: adding 20 μl of a ketoamine oxidase solution to 200 μl of a reaction solution (50 mM Tris-HCl buffer (pH 7.5), 0.1% Triton X-100, 0.03% 4-aminoantipyrine, 0.02% TOOS, 5 U/ml peroxidase, and 2 mM FZK or FVH); allowing the mixture to react at 37° C. for 5 minutes; adding 0.5 ml of 0.5% SDS; determining an absorbance at 555 nm (A1); performing the same operations using a reaction solution containing no FZK and FVH to determine an absorbance (Ab); and determining the reactivity from the difference (A1–Ab).

<Separation Operation>

The term "separation operation" refers to an operation for increasing the purity or concentration of glycated hemoglobin or a substance derived from glycated hemoglobin, in a process of a series of determination steps for determining glycated hemoglobin in a sample such as a whole blood specimen or hemolyzed red blood cell specimen, which includes column chromatography operation, membrane filtration operation, adsorption separation operation, and precipitate separation operation.

In order to specifically determine a glycated β-chain N-terminal of glycated hemoglobin using enzymes without a separation operation, among three kinds of glycated sites in glycated hemoglobin, intramolecular lysine, α-chain N-terminal, and β-chain N-terminal, the enzymes must have specificity only to the glycated site of the β-chain N-terminal. As enzymes to be used for obtaining such specificity, one kind of enzyme may be used, or plural kinds of enzymes may be used in combination. For example, the specificity may be obtained by combining oxidases, dehydrogenases, kinases, etc., which are enzymes that react with a glycated amino acid and/or a glycated peptide derived from a glycated β-chain N-terminal cleaved by degradation of glycated hemoglobin by a protease. Moreover, in order to determine only a β-chain N-terminal glycated using a protease or a ketoamine oxidase, it is necessary that the enzymes be combined according to the specificity as below.

That is, in the case where proteases and ketoamine oxidases are classified into (P1) to (P4) and (K1) to (K5), respectively, it is necessary that those enzymes be combined as below: <(P1) and (K1) or (K2) or (K3) or (K4)>, <(P2) and (K1) or (K3)>, <(P3) and (K1) or (K2)>, <(P4) and (K1)>, <(P3) and (K5) and (K3)>, and <(P3) and (K5) and (K4)>.

The properties of the respective classified enzymes are as follows.

(P1) cleaves a glycated amino acid and/or a glycated peptide only from a glycated β-chain N-terminal of glycated hemoglobin, (P2) cleaves a glycated amino acid and/or a glycated peptide only from glycated α- and β-chain N-terminals of glycated hemoglobin, (P3) cleaves a glycated amino acid and/or a glycated peptide only from a glycated β-chain N-terminal of glycated hemoglobin and a site including a intramolecular lysine, (P4) cleaves a glycated amino acid and/or a glycated peptide from a glycated α- and β-chain N-terminals of glycated hemoglobin and a site including a intramolecular lysine, (K1) reacts only with a glycated amino acid and/or a glycated peptide derived from a glycated β-chain N-terminal of glycated amino acids and/or glycated peptides cleaved from glycated hemoglobin by a protease to be used in combination, (K2) reacts only with a glycated amino acid and/or a glycated peptide derived from glycated α- and β-chain N-terminals of glycated amino acids and/or glycated peptides cleaved from glycated hemoglobin by a protease to be used in combination, (K3) reacts only with a glycated amino acid and/or a glycated peptide derived from a glycated β-chain N-terminal and from a site including intramolecular lysine of glycated amino acids and/or glycated peptides cleaved from glycated hemoglobin by a protease to be used in combination, (K4) reacts with a glycated amino acid and/or a glycated peptide derived from glycated α- and β-chain N-terminals and from a site including intramolecular lysine that have been cleaved from glycated hemoglobin by a protease to be used in combination, and (K5) reacts with a glycated amino acid and/or a glycated peptide from a site including intramolecular lysine without reacting with a glycated amino acid and/or a glycated peptide derived from a glycated β-chain N-terminal of glycated amino acids and/or glycated peptides cleaved from glycated hemoglobin by a protease to be used in combination.

<Screening of Protease>

The inventors of the present invention have made extensive studies and as a result have invented, as a screening method of obtaining a protease having the specificity (P1) or (P3), a method of selecting a protease to cleave a glycated amino acid and/or a glycated peptide only when a hemoglobin β-chain N-terminal glycated peptide is used as a substrate in the case of using a hemoglobin α-chain N-terminal glycated peptide and a hemoglobin β-chain N-terminal glycated peptide as substrates. The lengths of the α-chain N-terminal glycated peptide and β-chain N-terminal glycated peptide used above are not particularly limited, but it has been found out that screening may be performed using a glycated peptide having a length of 3 amino acids to 20 amino acids. The peptides may be derived from chemically synthesized compounds or natural products such as glycated hemoglobin.

Specific examples thereof include: as the β-chain N-terminal glycated peptide, 1-deoxyfructosyl-L-valyl-L-histidyl-L-leucyl-L-threonyl-L-proline (SEQ ID NO: 36) (manufactured by Peptide Institute, Inc., hereinafter also referred to as β-glycated pentapeptide); and as the α-chain N-terminal glycated peptide, 1-deoxyfructosyl-L-valyl-L-leucyl-L-seryl-L-prolyl-L-alanine (SEQ ID NO: 50) (manufactured by Peptide Institute, Inc., hereinafter also referred to as α-glycated pentapeptide). In the case where those pentapeptides are used as substrates, a glycated amino acid, glycated dipeptide, glycated tripeptide, or glycated tetrapeptide may be cleaved by a protease. A glycated amino acid and/or a glycated peptide cleaved from an α-chain N-terminal glycated peptide and a β-chain N-terminal glycated peptide by a protease may be detected using an enzyme that reacts with the cleaved glycated amino acid and/or glycated peptide without substantially reacting with an α-chain N-terminal glycated peptide and a β-chain N-terminal glycated peptide, and examples of such enzyme include oxidases, dehydrogenases, and kinases.

An example of the oxidase includes ketoamine oxidase. Examples of the ketoamine oxidase include oxidases derived from the genus *Achaetomiella*, the genus *Achaetomium*, the genus *Thielavia*, the genus *Chaetomium*, the genus *Gelasinospora*, the genus *Microascus*, the genus *Coniochaeta*, the genus *Eupenicillium* (all of them are described in the description of EP 1,291,416), the genus *Corynebacterium* (JP-A-61-268178), the genus *Aspergillus* (JP-A-03-155780), the genus *Penicillium* (JP-A-04-4874), the genus *Fusarium* (JP-A-05-192193, JP-A-07-289253, JP-A-08-154672), the genus *Gibberella* (JP-A-05-192153, JP-A-07-289253), the genus *Candida* (JP-A-0646846), the genus *Aspergillus* (JP-A-10-33177, JP-A-10-33180), *Neocosmospora vasinfecta* (NBRC 7590), *Coniochaetidium savoryi* (ATCC36547), *Arthrinium* sp. TO6 (FERM P-19211), *Arthrinium phaeospermum* (NBRC 31950), *Arthrinium phaeospermum* (NBRC 6620), *Arthrinium japonicam* (NBRC 31098), *Pyrenochaeta* sp. YH807 (FERM P-19210), *Pyrenochaeta gentianicola* (MAFF425531), *Pyrenochaeta terrestris* (NBRC 30929), *Leptosphaeria nodorum* (name during the conidial generation is *Phoma hennebelgii*) (NBRC 7480), *Leptosphaeria doliolum* (JCM2742), *Leptosphaeria maculans* (name during the conidial generation is *Phoma lingam*) (MAFF726528), *Pleospora herbarum* (NBRC 32012), *Pleospora betae* (name during the conidial generation is *Phoma betae*) (NBRC 5918), *Ophiobolus herpotrichus* (NBRC 6158), *Curvularia clavata* YH923 (FERM BP-10009), and mutant enzymes thereof.

The substrate specificities of a ketoamine oxidase derived from *Curvularia clavata* YH 923 (FERM BP-10009) to FVH is 100%, while that to 1-deoxyfructosyl-L-valyl-L-histidyl-L-leucine (hereinafter also referred to as β-glycated tripeptide or FVHL), 1-deoxyfructosyl-L-valyl-L-histidyl-L-leucyl-L-threonine (SEQ ID NO: 37) (hereinafter also referred to as β-glycated tetrapeptide or FVHLT), β-glycated pentapeptide, 1-deoxyfructosyl-L-valyl-L-leucine (hereinafter also referred to as FVL) and α-glycated pentapeptide are 0.09%, 0.0009%, 0%, 3.4%, and 0.01%, respectively. Therefore, the activity of a protease to cleave FVH from a β-glycated pentapeptide and the activity of a protease to cleave FVL from an α-glycated pentapeptide may be detected by using the ketoamine oxidase. In the case where a glycated amino acid and/or a glycated peptide cleaved by a protease are detected using an oxidase, the amount of generated hydrogen peroxide may be detected by electrodes, luminescence, fluorescence, absorbance, etc, but it is easy to detect absorbance using peroxidase and a chromogen. For example, protease activity may easily be confirmed by determining absorbance changes from at 540 to 570 nm using 4-aminoantipyrine (manufactured by Wako Pure Chemical Industries, Ltd.) and TODB (manufactured by Dojindo Laboratories) as chromogens.

Examples of a protease that is obtained by the above-described screening method and has the specificity (P1) or (P3) include proteases derived from bacteria belonging to the genus *Bacillus*, the genus *Aeromonas*, and the genus *Lysobacter*. More specific examples thereof include: neutral proteinase derived from *Bacillus* sp. (manufactured by Toyobo Co., Ltd.); and a protease derived from *Bacillus* sp. ASP 842 (FERM BP-08641), *Aeromonas hydrophila* NBRC 3820, or *Lysobacter enzymogenes* YK-366 (FERM BP-10010).

Of those strains, *Bacillus* sp. ASP 842 (FERM BP-08641) and *Lysobacter enzymogenes* YK-366 (FERM BP-10010) are novel strains that have been isolated by the inventors of the present invention, and *Bacillus* sp. ASP 842 (FERM BP-08641) and *Lysobacter enzymogenes* YK-366 (FERM BP-10010) have been deposited in International Patent Organism Depositary, National Institute of Advanced Industrial Science and Technology, Tsukuba Central 6, 1-1-1 Higashi, Tsukuba, Ibaraki, Japan on Feb. 24, 2004 and on Jan. 30, 2004, respectively.

The mycological properties of those deposited strains are shown below and were identified as follows.

1. ASP842 (FERM BP-08641) is a Gram-positive *bacillus* having a size of 0.8 to 1.0×2.0 to 3.0 μm and has the properties shown in Table 1, so that it was identified as *Bacillus* sp. by Bergy's Manual of Systematic Bacteriology (1984).

TABLE 1

| | |
|---|---|
| (a) Morphological Properties | |
| Culture condition (Medium: Nutrient Agar; 30 degree C.) | |
| Cell shape | 0.8-1.0 × 2.0-3.0 μm |
| Cell polymorphism | − |
| Motility | + (peritrichous) |
| Sporulation | + |
| (b) Cultural Properties | |
| Culture condition (Medium: Nutrient Agar; 30 degree C.) | |
| Color | creamy |
| Gloss | − |
| Pigment production | − |
| Culture condition (Liquid medium: Nutrient Broth; 30 degree C.) | |
| Growth on the surface | + |
| Opacity of medium | − |
| Culture condition (gelatin stab culture; 30 degree C.) | |
| Growth | + |
| Gelatin liquefaction | + |
| Culture codintion (litmus milk; 30 degree C.) | |
| coagulation | − |
| liquefaction | − |
| (c) Physiological Properties | |
| 1) Gram staining | + |
| 2) Nitrate Reduction | + |
| 3) Denitrification Reaction | − |
| 4) MR test | − |
| 5) VP test | + |
| 6) Indole Production | − |
| 7) Hydrogen sulfide production | − |
| 8) Starch Hydrolysis | + |
| 9) Utilization of citrate (Koser/Christensen) | −/+ |
| 10) Utilization of inorganic nitorgen source (nitrate/ammonium salt) | −/+w |
| 12) Urease activity | − |

TABLE 1-continued

| | |
|---|---|
| 13) Oxidase | + |
| 14) Catalase | + |
| 15) Growth Range pH 5/8/10 | +/+/+w |
| Growth Range Temperature 20/25/45/50 | +/+/+/+ |
| 16) Growth Condition (aerobic/anerobic) | +/− |
| 17) O-F Test (oxidation/fermentation) | −/− |
| 18) Acid/Gas production from sugars | |
| L-arabinose | −/− |
| D-glucose | +/− |
| D-fructose | +/− |
| maltose | +/− |
| lactose | +/− |
| D-sorbitol | +/− |
| inositol | +/− |
| D-xylose | +/− |
| D-mannose | +/− |
| D-galactose | −/− |
| sucrose | +/− |
| trehalose | +/− |
| D-mannitol | +/− |
| glycerin | +/− |
| (d) Other physiological properties | |
| beta-galactosidase activity | − |
| arginine dihydrolase activity | − |
| lysine decarboxylase activity | − |
| tryptophan deaminase activity | + |
| gelatinase activity | + |
| phosphatase activity | + |
| Propionate utilization | − |
| Growth in the presence of 10% NaCl | + |
| Casein hydrolysis | + |
| Hippuric acid hydrolysis | − |

2. YK-366 (FERM BP-10010) is a Gram-negative aerobic *bacillus* having a size of 0.4×5 to 50 μm and has the properties shown in Table 2, so that it was identified as *Lysobacter enzymogenes* by Bergy's Manual of Systematic Bacteriology (1989).

TABLE 2

| Tests | Results |
|---|---|
| Shape | *bacillus* |
| Gram Staining | − |
| Motility | − |
| Pigment production* | +, brown |
| Colony texture | mucoid |
| Colony color | pale yellow |
| Catalase | − |
| Oxidase | − |
| VP reaction | − |
| Methyl red reaction | − |
| Indole production | − |
| L-arginine Utilization | − |
| Urease | − |
| Hydorolysis | |
| esculin | + |
| gelatin | + |
| starch | − |
| beta-galactosidase | + |
| Growth on EMB agar medium | +, pink |
| Assimilation of carbon sources | |
| glucose | + |
| L-arabinose | − |
| D-mannose | + |
| D-mannitol | + |
| N-acetyl-D-glucosamine | − |
| maltose | + |
| potassium gluconate | + |

TABLE 2-continued

| Tests | Results |
| --- | --- |
| n-caproic acid | − |
| adipic acid | − |
| DL-malic acid | + |
| sodium citrate | − |
| phenyl acetate | − |

*PCA Plate Colony Count Agar

<Production of Protease from Cultured Product>

Next, there will be described a method of culturing a protease-producing bacterium that may be used in the present invention and a method of producing the protease. As means for culturing the protease-producing bacterium of the present invention, solid culture or liquid culture may be employed, but preferable is aeration liquid culture using a flask, jar fermenter, or the like. As a medium, a wide variety of media to be generally used for culture of bacteria may be used. Examples of a carbon source to be used include glucose, glycerol, sorbitol, lactose, mannose, or the like. Examples of a nitrogen source to be used include an yeast extract, a meat extract, tryptone, peptone, or the like. Examples of an inorganic salt to be used include sodium chloride, magnesium chloride, magnesium sulfate, calcium chloride, or the like. For culture conditions, there may be employed a culture time such that the target protease gains the maximum titer or maximum purity at pH 5.0 to 8.0 and culture temperature of from 25 to 37° C., and for example, culture may be performed for 16 to 72 hours.

Subsequently, collection of the protease will be described. In the case where the protease is secreted from cells, a solution containing a crude protease obtained by removing the cells from a culture medium by filtration, centrifugation, etc is use. Meanwhile, in the case where the protease is present in cells, there is used a solution containing a crude protease that is obtained by the following steps: separating the cells from a culture medium by filtration, centrifugation, etc.; suspending the cells in a buffer such as a phosphate buffer or Tris-HCl buffer supplemented with, if necessary, a surfactant, metallic salt, saccharide, amino acid, polyol, chelator, etc.; homogenizing the cells using lysozyme, ultrasonic waves, glass beads, etc.; and removing insoluble products by filtration, centrifugation, etc. The solution containing the crude protease is treated using a known isolation or purification means for proteins or enzymes to yield a purified protease. For example, general enzyme purification methods such as a fractional precipitation method using an organic solvent including acetone or ethanol, salting-out method using ammonium sulfate or the like, ion-exchange chromatography method, hydrophobic chromatography method, affinity chromatography method, and gel filtration method may be appropriately selected and combined, to thereby obtaining a purified protease. The purified protease may be cryopreserved after adding appropriate stabilizer(s) such as sucrose, glycerol, or an amino acid (about 1 to 50%) and a coenzyme or the like (about 0.01 to 1%) singly or in combination of two or more of them.

<Screening of Ketoamine Oxidase>

Examples of a screening method for obtaining a ketoamine oxidase that has the property (K1); has the property (K2) and reacts with FVH; or has the property (K3) include a method based on an index for reactivity to: FVL as a representative example of a glycated amino acid and/or a glycated peptide derived from an α-chain N-terminal; FVH as a representative example of a glycated amino acid and/or a glycated peptide derived from an β-chain N-terminal; or FK or ZFK as a representative example of a glycated amino acid and/or a glycated peptide from a site including intramolecular lysine, which have been cleaved from glycated hemoglobin by a protease. In particular, the method is performed based on an index such that the reactivity to FK or FZK is 5% or less compared with that to FVH. The reactivity is preferably 4% or less, more preferably 2% or less. The thus-obtained ketoamine oxidase that has the property (K1); has the property (K2) and reacts with FVH; or has the property (K3) may be: a natural ketoamine oxidase isolated from nature; a mutant ketoamine oxidase obtained by artificial modification of a natural ketoamine oxidase using a known genetic engineering technique such as amino acid substitution, deletion, or insertion; and ketoamine oxidase that may be obtained by chemically modifying natural and mutant ketoamine oxidases using a polyethylene glycol derivative, succinimide derivative, maleimide derivative, etc.

<Mutated Ketoamine Oxidase>

No particular limitations are imposed on an existing ketoamine oxidase that may be used in obtaining a mutated ketoamine oxidase that has a property described in (K1); has a property described in (K2) and reacts with FVH; or has a property described in (K3) by artificial modification of one or more amino acids of an existing ketoamine oxidase such as substitution, deletion, or insertion. Examples thereof include the ketoamine oxidase for obtaining a protease having the specificity (P1) or (P3), which is described in the screening method.

Meanwhile, examples of a ketoamine oxidase that reacts with FVH include ketoamine oxidases derived from microorganisms belonging to the genera *Coniochaeta* (EP 1,291, 416), *Eupenicillium* (EP 1,291,416), *Curvularia*, and *Neocosmospora*.

Those enzymes have been analyzed on a genetic level, and the primary structures have been estimated as shown in FIG. 1. The homology of those enzymes on an amino acid level is 75% or more, and there are conserved regions represented by the symbols "*", so that those enzymes are included as examples of a ketoamine oxidase that includes an amino acid sequence having at least 75% of homology to the amino acid sequence described in SEQ ID NO: 1. Meanwhile, substitution, deletion, or insertion of an amino acid is not limited as long as mutation is performed so as to have the property (K1); have the property (K2) and react with FVH; or have the property (K3), but it is desirable that, for example, at least one of amino acids corresponding to amino acids at positions 58 and 62 in the amino acid sequence described in SEQ ID NO: 1 be substituted. It is more desirable that an amino acid corresponding to an amino acid at position 58 be substituted by valine, threonine, asparagine, cysteine, serine, or alanine; and an amino acid corresponding to an amino acid at position 62 be substituted by histidine.

<Mutated Ketoamine Oxidase Expression Vector and Host Cell>

A ketoamine oxidase that has the property K1); has the property (K2) and reacts with FVH; or has the property (K3) may be obtained as follows: if necessary, a gene encoding the enzyme is ligated to a plasmid vector; the gene is transferred to a host microorganism such as a microorganism belonging to the genus *Saccharomyces*, the genus *Pichia*, the genus *Acremonium*, the genus *Bacillus*, the genus *Pseudomonas*, the genus *Thermus*, or the genus *Escherichia*; the microorganism is cultured; alternatively the encoding gene is transcribed and translated in vitro; and a treatment is performed using a known isolation or purification means for proteins or enzymes.

<Determination Reagent Kit>

A method and reagent kit for specifically determining a glycated β-chain N-terminal of glycated hemoglobin using a protease and a ketoamine oxidase without a separation operation may include a combination of a protease and a ketoamine oxidase to obtain specificity to a glycated β-chain N-terminal as well as a peroxidase and chromogen, and if necessary, there may be appropriately added a buffer component, salt, surfactant, metallic ion, electron acceptor, chelator, sugar, amino acid, ascorbate oxidase, tetrazolium salt, polyol, enzyme stabilizer, enzyme reaction promoter, antibacterial agent, antioxidant, reductant, coenzyme, etc.

In the case where proteases and ketoamine oxidases are divided into (P1) to (P4) and (K1) to (K5), respectively, as described above, all combinations of <(P1) and (K1) or (K2) or (K3) or (K4)>, <(P2) and (K1) or (K3)>, <(P3) and (K1) or (K2)>, <(P4) and (K1)>, <(P3) and (K5) and (K3)>, and <(P3) and (K5) and (K4)> may be employed as combinations of a protease and a ketoamine oxidase to obtain specificity to a glycated β-chain N-terminal. However, in general, in the case where an N-terminal amino group of a protein has been glycated, reactivity for cleavage of a glycated amino acid from an N-terminal region is low. Therefore, desirable is a protease to cleave a glycated peptide from a glycated amino acid in a β-chain N-terminal. Examples of a protease that is obtained by the above-described screening of a protease, has the property (P3), and has a property to cleave FVH from a β-chain N-terminal include proteases derived from bacteria belonging to the genera *Bacillus, Aeromonas, Lysobacter*, etc. More specific examples thereof include a neutral proteinase derived from *Bacillus* sp. (manufactured by Toyobo Co., Ltd.), proteases derived from *Bacillus* sp. ASP-842 (FERM BP-08641), *Aeromonas hydrophila* NBRC 3820, and *Lysobacter enzymogenes* YK-366 (FERM BP-10010). Meanwhile, in order to improve the reactivity while maintaining the specificity, the screened protease may be used in combination with other appropriate protease.

The length of a glycated peptide cleaved from a glycated β-chain N-terminal of hemoglobin by a protease is 20 amino acids or less and is not particularly limited as long as the peptide may be detected with a ketoamine oxidase used in combination. For example, in the case of using a ketoamine oxidase derived from *Curvularia clavata* YH 923 (FERM BP-10009), it is desirable that a glycated peptide cleaved from a glycated β-chain N-terminal of hemoglobin by a protease be FVH.

Although the ketoamine oxidase is not limited as long as it may construct the above-described combination with a protease, desirable is a protease to cleave a glycated peptide rather than a glycated amino acid from a β-chain N-terminal in terms of reactivity. Therefore, a glycated amino acid and/or a glycated peptide derived from a glycated β-chain N-terminal mentioned in (K1) to (K5) is desirably a glycated peptide derived from a glycated β-chain N-terminal. For example, a ketoamine oxidase derived from *Curvularia clavata* YH 923 (FERM BP-10009) reacts with a glycated dipeptide derived from a glycated β-chain N-terminal (FVH) and does not substantially react with a glycated dipeptide derived from a glycated α-chain N-terminal (FVL), so that it may be used as a ketoamine oxidase having the property (K3). Meanwhile, a mutant having reactivity to FZK of 5% or less compared to that to FVH may be used as a ketoamine oxidase having the property (K1), and fructosyl amine oxidase derived from *Fusarium oxysporum* (manufactured by Asahi Kasei Pharma Corporation) may be used as a ketoamine oxidase having the property (K5).

<Reaction Condition>

The reaction condition of a protease to cleave a glycated amino acid and/or a glycated peptide derived from a glycated β-chain N-terminal of glycated hemoglobin is not limited as long as it is sufficient for reaction proceeding. For example, desirable is generally a reaction condition to obtain the property (P1) by regulating the pH, salt concentration, added surfactant amount, added metallic ion amount, reaction temperature, added oxidant-reductant amount, or buffer concentration to enhance the specificity of a protease having the property (P3) or (P2). In particular, for a neutral proteinase derived from *Bacillus* sp. (manufactured by Toyobo Co., Ltd.), and proteases derived from *Bacillus* sp. ASP-842 (FERM BP-08641), *Aeromonas hydrophila* NBRC 3820, and *Lysobacter enzymogenes* YK-366 (FERM BP-10010), when a ketoamine oxidase derived from *Curvularia clavata* YH 923 (FERM BP-10009) is used as a ketoamine oxidase to be combined, those protease necessarily become proteases having the property (P1) under a reaction condition of pH 5.0 to 6.0, so that such reaction condition is preferable.

The reaction condition of a ketoamine oxidase is not limited as long as it is sufficient for reaction proceeding. For example, desirable is a reaction condition to obtain the reactivity to FZK of 30% or less by regulating the pH, salt concentration, added surfactant amount, added metallic ion amount, reaction temperature, added redox amount, or buffer concentration. Particularly desirable is a reaction condition of pH 5.5 to 6.5 because the specificity to FVH that is a glycated amino acid and/or glycated peptide derived from a β-chain N-terminal which is cleaved by a protease may be enhanced.

The correct determination of a glycated β-chain N-terminal of glycated hemoglobin by the above-described method and reagent kit for specifically determining a glycated β-chain N-terminal of glycated hemoglobin using a protease and a ketoamine oxidase without a separation operation may be confirmed by using a sample whose hemoglobin content and glycation rate of a β-chain N-terminal of the hemoglobin are correctly shown. As the sample whose hemoglobin content and glycation rate of a 3-chain N-terminal of the hemoglobin are correctly shown, a sample whose a determination value obtained by the method described in Clinical Chemistry and Laboratory Medicine 40(1): 78-89 (2002) (IFCC value) is specified is desirably used. Alternatively, in a sample whose a determination value obtained by other method is specified, the IFCC value may be obtained by the conversion equation described in Rinsho Kensa 46(6), 729-734 (2002). Meanwhile, a sample of glycated hemoglobin may be prepared from human blood by appropriately combining operations such as blood corpuscle separation, hemolysis, centrifugation, dialysis, ion-exchange chromatography, and affinity chromatography (Clinical Chemistry and Laboratory Medicine 36(5): 299-308 (1998)), or a commercially available sample may be purchased and used.

<Determining Object>

The determining object of the above-described method and reagent kit for specifically determining a glycated β-chain N-terminal of glycated hemoglobin using a protease and a ketoamine oxidase without a separation operation is not limited as long as it includes glycated hemoglobin, and examples thereof include a whole blood sample, hemolyzed blood cell sample, and purified hemoglobin sample.

Next, the present invention will be described by way of reference examples and examples.

Reference Example

Production Method of Ketoamine Oxidase Derived from *Curvularia clavata* YH 923 (FERM BP-10009)

Although *Curvularia clavata* YH 923 (FERM BP-10009) produces a ketoamine oxidase that reacts with FVH (hereinafter also referred to as FOD923), the amount of the produced ketoamine oxidase is small. Therefore, as shown below, FOD923 gene was expressed in *Escherichia coli* and purified, to thereby yield FOD923.

(1) Preparation of *Curvularia clavata* YH 923 (FERM BP-10009) Chromosomal DNA 100 ml of Sabouraud medium (glucose 4.0%, polypeptone 1.0%, pH 5.6) was poured into a 500 ml-volume shaking flask and sterilized by an autoclave, and *Curvularia clavata* YH 923 (FERM BP-10009) was inoculated thereto and cultured with shaking at 25° C. for 4 days, followed by filtration of the culture medium using a No. 2 Filter Paper, to thereby collect the cells. The collected cells were frozen with liquid nitrogen and pulverized in a mortar to yield fine powder. Then, 15 ml of a buffer for DNA extraction (5.0% SDS, 0.1 M NaCl, 50 mM Tris-HCl, pH 8.0) was added thereto, and the mixture was slowly shaken to dissolve the powder. Subsequently, the supernatant was collected by centrifugation (5,000 rpm, 6 min, room temperature), and phenol/chloroform extraction and ether extraction were performed three times and twice, respectively, to evaporate ethers remaining in the aqueous layer. Then, 1 ml of 3 M sodium acetate and 25 ml of ethanol were added thereto, and the mixture was allowed to stand at −30° C. for 30 minutes. Thereafter, chromosomal DNA was collected by centrifugation (12,000 rpm, 10 min, 4° C.), washed with 70% ethanol, and dissolved in 400 µl of TE. Subsequently, 10 µl (0.132 U) of RNase was added to the resultant DNA solution, and the mixture was treated at 37° C. for 1 hour. Then, 5 µl (0.6 U) of proteinase K was added thereto, and the mixture was treated at 50° C. for 1 hour. Thereafter, phenol/chloroform extraction (twice) and chloroform/isoamyl alcohol extraction (once) were performed, and ethanol precipitation was performed to collect DNA. Subsequently, the collected DNA was washed with a 70% ethanol solution, and ethanol was removed, followed by dissolution in 200 µl of TE, to thereby yield a chromosomal DNA solution.

(2) Amplification of FOD923 Gene Fragment (a) Acquirement of FOD923 Gene Fragment On the basis of known gene information of ketoamine oxidases, the following primers P11 and P12 were designed.

P11
(SEQ ID NO: 2)
AA (A/G) GC (C/T) AT (C/T) AACGC (C/T) AT (C/T) GG

P12
(SEQ ID NO: 3)
AC (C/G) ACGTGCTT (A/G) CC (A/G) ATGTT 35 cycles of PCR were performed using the chromosomal DNA obtained by the above-described method as a template DNA and a primer P11 and a primer P12 in combination. As a result, a DNA fragment having a size of about 800 bp was specifically amplified, and the amplified DNA fragment (sequence from the 1021st base to the 1790th base in SEQ ID NO: 1) was sequenced.

(b) FOD923 Gene Sequencing

A DNA fragment of the 5' upstream region adjacent to the DNA fragment having a size of about 800 bp obtained in (a) was amplified by cassette-ligation-medicated PCR using an LA-PCR in vitro Cloning kit (manufactured by Takara Bio Inc.) after digesting chromosomal DNA with a restriction enzyme XbaI. That is, XbaI cassette (manufactured by Takara Bio Inc.) was bound to a fragment obtained by a restriction enzyme treatment of the chromosomal DNA, and 35 cycles of PCR were performed using the resultant DNA as a template DNA, a primer C1 (manufactured by Takara Bio Inc.), and the following primer P13. Then, 35 cycles of PCR were further performed using a solution obtained by diluting the reaction solution 100-fold as a template, a primer C2 (manufactured by Takara Bio Inc.), and the following primer P14. As a result, a DNA fragment having a size of 1,200 bp was specifically amplified. Then, the amplified DNA fragment (sequence from the 1st base to the 1044th base in SEQ ID NO: 1) was sequenced.

A DNA fragment of the 3' downstream region adjacent to the DNA fragment having a size of about 800 bp obtained in (a) was amplified by cassette-ligation-medicated PCR using an LA-PCR in vitro Cloning kit (manufactured by Takara Bio Inc.) after digesting chromosomal DNA with a restriction enzyme SalI. That is, SalI cassette (manufactured by Takara Bio Inc.) was bound to a fragment obtained by a restriction enzyme treatment of the chromosomal DNA, and 35 cycles of PCR were performed using the resultant-DNA as a template DNA, a primer C1 (manufactured by Takara Bio Inc.), and the following primer P15. Then, 35 cycles of PCR were further performed using a solution obtained by diluting the reaction solution 100-fold as a template, a primer C2 (manufactured by Takara Bio Inc.), and the following primer P16. As a result, a DNA fragment having a size of 1,000 bp was specifically amplified. Then, the amplified DNA fragment (sequence from the 1775th base to the 2212th base in SEQ ID NO: 1) was sequenced.

The base sequences determined as above were ligated to determine a base sequence of FOD923 gene (SEQ ID NO: 1).

P13  GCCAAAAGAGGCTGCTTGAACGAT  (SEQ ID NO: 38)

(a complementary sequence to the base sequence from 1,083 to 1,106 of SEQ ID NO: 1)

P14  GCATCCAGCACCACCAAAACAAAC  (SEQ ID NO: 39)

(a complementary sequence to the base sequence from 1,062 to 1,086 of SEQ ID NO: 1)

P15  TGGTGCCAGAACAACATGTACTGACC  (SEQ ID NO: 40)

(a base sequence from 1,713 to 1,738 of SEQ ID NO: 1)

P16  ACCTGGTTTGCCTAGGCACACA  (SEQ ID NO: 41)

(a base sequence from 1,736 to 1,757 of SEQ ID NO: 1)

(3) Preparation of *Escherichia coli* Expressing Ketoamine Oxidase Derived from *Curvularia clavata* YH 923 (FERM BP-10009)

In order to express FOD923 in *Escherichia coli*, three regions, i.e., the sequence from the 753rd base to the 807th base in SEQ ID NO: 1, sequence from the 1231st base to the 1279th base in SEQ ID NO: 1, and sequence from the 1696th base to the 1750th base in SEQ ID NO: 1 were estimated as introns from the homology between a ketoamine oxidase derived from *Penicillium janthinellum* (JP-A-11-46769) and a ketoamine oxidase derived from *Aspergillus nidulans*.

The following operations were performed to remove introns and to create an expression plasmid in *Escherichia coli*.

First, there were synthesized: DNA fragments P22 to P27 having positive and complementary sequences of a sequence including 40 to 50 bases so as to flank intron-existing regions to be removed; a DNA fragment P21 obtained by adding a restriction sequence of a restriction enzyme NcoI onto the initiating codon ATG of FOD923 gene; and a DNA fragment P28 having a complementary sequence obtained by adding a restriction enzyme SacI onto the site just behind the stop codon of FOD923 gene.

Subsequently, 4 kinds of PCR were performed using a chromosomal DNA of *Curvularia clavata* YH 923 (FERM BP-10009) as a template and using primers P21 and P23, P22 and P25, P24 and P27, and P26 and P28 respectively in combination, to thereby yield amplified DNA fragments each having a size of 327 bp, 480 bp, 471 bp, or 254 bp where intron regions had been removed. Then, the resultant four fragments were mixed and used as templates to perform PCR again using P21 and P28 as primers, to thereby yield a DNA fragment that has a size of about 1.4 kb and has one FOD923 gene ligated to four fragments at three homologous regions where introns had been removed.

In order to produce FOD923 in *Escherichia coli* at a high level, there was used a pyruvate oxidase promoter (JP-A-07-67390) derived from *Aerococcus viridans* that is a high expression promoter. Specific procedures thereof will be described below.

1) In order to obtain a promoter region of a pyruvate oxidase gene from a plasmid pOXI3 including a pyruvate oxidase gene of *Aerococcus viridans* shown in JP-B-07-67390, pOXI3 was cleaved with DraI to separate a promoter region of a pyruvate oxidase gene that has a DNA sequence having a size of 202 bp described in SEQ ID NO: 6, and it was ligated to a fragment obtained by cleaving pUC13 with SalI and blunting it with T4 DNA polymerase, to thereby yield a plasmid pKN19 where the direction of an ampicillin-resistant gene in pUC13 and the direction of a pyruvate oxidase gene promoter are the same.

2) In order to perform more effective expression by a promoter, there were synthesized: a DNA fragment P31 having a base sequence described in SEQ ID NO: 7, which was designed so as to provide a ribosome-binding sequence region and multicloning site in the downstream of a pyruvate oxidase gene promoter of pKN19; and a DNA fragment P32 that is a complementary sequence thereof and has a base sequence described in SEQ ID NO: 8. Then, annealing was performed, and the fragments were ligated to pKN19 cleaved with XbaI and EcoRI, to thereby prepare a plasmid pPOS2.

3) A DNA fragment that has a size of about 1.4 kb and includes the above-described FOD923 gene where introns had been removed was cleaved with NcoI and SacI, and the resultant product was integrated in pPOS2 cleaved with NcoI and SacI as well, to thereby prepare a plasmid pPOSFOD923 where FOD923 gene was integrated in the downstream of a pyruvate oxidase gene promoter.

4) *Escherichia coli* W3110 was transformed with the resultant pPOSFOD923 to create *Escherichia coli* FAOD923 that expresses FOD923.

P21
(SEQ ID NO: 4)
CACACATCCTCGTCATTTCGCCATGGCGCCCTCAAGAGCAAAC

P22
CAAAGAGTATTTCCACAACACTGGAAGACTCGACTGTGCACATGGGGAAG

AGG (SEQ ID NO: 42)
(a base sequence from 725 to 752 and 808 to 832 of

SEQ ID NO: 1)

P23
CCTCTTCCCCATGTGCACAGTCGAGTCTTCCAGTGTTGTGGAAATACTCT

TTG (SEQ ID NO: 43)
(a complementary sequence to the base sequence from 725 to 752 and 808 to 832 of SEQ ID NO: 1)

P24
GACCTGGAAGATCAATGCGTTTCAAAAGCTTGGGTATATGCTCACATACA

GCTTAC (SEQ ID NO: 44)
(a base sequence from 1,204 to 1,230 and 1,280 to 1,308 of SEQ ID NO: 1)

P25
GTAAGCTGTATGTGAGCATATACCCAAGCTTTTGAAACGCATTGATCTTC

CAGGTC (SEQ ID NO: 45)
(a complementary sequence to the base sequence from 1,204 to 1,230 and 1,280 to 1,308 of SEQ ID NO: 1)

P26
CTTTGTGCTGGCGACAGGGGACAGCGGGCACACATTCAAACTTTTGCCAA

ATATC (SEQ ID NO: 46)
(a base sequence from 1,669 to 1,695 and 1,751 to 1,778 of SEQ ID NO: 1)

P27
GATATTTGGCAAAAGTTTGAATGTGTGCCCGCTGTCCCCTGTCGCCAGCA

CAAAG (SEQ ID NO: 47)
(a complementary sequence to the base sequence from 1,669 to 1,695 and 1,751 to 1,778 of

SEQ ID NO: 1)

P28
(SEQ ID NO: 5)
CACGCTACAAGACGAGTTTCGAGCTCTATAACTTGGACTTGACAAC

P31
(SEQ ID NO: 7)
CTAGAGGAATAACACCATGGCCGTCGACGCTAGCATGCATGGATCCCGGG

TACCGAGCTCG

P32
(SEQ ID NO: 8)
AATTCGAGCTCGGTACCCGGGATCCATGCAGCTAGCGTCGACGGCCATGG

TGTTATTCCT (4) Production of Ketoamine Oxidase Derived from *Curvularia clavata* YH923 (FERM BP-10009)

The above-prepared *Escherichia coli* FAOD923 was inoculated in a 2.4 cm diameter test tube that each contains 10 ml of a medium (pH 7.0) containing with 3% sorbitol, 1.5% peptone, 1.5% beer yeast extract, and 50 µg/ml ampicillin and cultured with shaking at 28° C. for 12 hours, to thereby yield an inoculum. The inoculum was inoculated in a 30 L jar fermenter that contains 20 L of a medium (pH 7.0) containing 3% sorbitol, 1.5% peptone, 1.5% beer yeast extract, 0.1% antifoamer, and 50 μg/ml ampicillin and cultured with stirring at 37° C. for 18 hours.

After completion of the culture, the cultured cells were collected and suspended in 4 L of 10 mM Tris-HCl buffer (pH 7.5), and solubilized by ultrasonic disintegration (212 KU). The solubilized solution was centrifuged at 8,000 rpm for 30 minutes, and the supernatant was subjected to ion-exchange chromatography using Q-Sepharose Big Beads resin (2 L) (manufactured by Amersham). Meanwhile, elution was performed with Tris-HCl buffer (pH 7.5) including 0 M, 0.1 M, 0.3 M, or 0.5 M NaCl. As a result, fractions eluted with buffers including 0.3 M and 0.5 M NaCl were collected as active fractions (180 KU). The enzyme solutions were concentrated to 750 ml by a module (manufactured by Amicon), and the concentrated solution was dialyzed against 10 mM Tris-HCl buffer (pH 7.5) overnight. The dialyzed solution was subjected to ion-exchange chromatography again using Q-Sepharose HP resin (500 ml) (manufactured by Amersham). Meanwhile, elution was performed with Tris-HCl buffer (pH 7.5) including 0 to 0.3 M NaCl by linear gradient, and fractions eluted with buffers including 0.15 to 0.2 M NaCl (92 KU) were collected. The enzyme solutions were concentrated to 500 ml, and the concentrated solution was dialyzed against 10 mM Tris-HCl buffer (pH 7.5) overnight, followed by freeze-drying, to thereby yield purified FOD923. The determination reagent and determination method for FOD923 activity will be described below.

<Determination Reagent>

50 mM Tris-HCl buffer (pH 7.5)

1 mM FVH (manufactured by Peptide Institute, Inc.)

0.02% 4-aminoantipyrine (manufactured by Wako Pure Chemical Industries, Ltd.)

0.02% TOOS (manufactured by Dojindo Laboratories)

5 U/ml Peroxidase (manufactured by Sigma Corporation)

(TOOS: N-ethyl-N-(2-hydroxy-3-sulfopropyl)-3-methylaniline)

<Determination Method>

1 ml of a determination reagent was poured into a test tube and preheated at 37° C. for 5 minutes, and then 0.05 ml of an enzyme solution was added thereto, and the solution was allowed to react for 5 minutes. After the reaction, 2 ml of 0.5% SDS was added to terminate the reaction, and the absorbance at a wavelength of 550 nm (Aa) was determined. Meanwhile, as a blank, the same operations were performed using a determination reagent including no FVH to determine the absorbance (Ab). From the absorbance difference (Aa–Ab) between the absorbance (Aa) and absorbance of the blank (Ab), the enzyme activity was calculated.

One unit of the enzyme activity was defined as an enzyme amount for generation of 1 μmol of hydrogen peroxide at 37° C. for 1 minute.

Reference Example

Production Method of Ketoamine Oxidase Derived from Neocosmospora vasinfecta 474

Although Neocosmospora vasinfecta 474 produces a ketoamine oxidase that reacts with FVH (hereinafter also referred to as FOD474), the amount of the produced ketoamine oxidase is small. Therefore, as shown below, the ketoamine oxidase gene was expressed in Escherichia coli and purified, to thereby yield the ketoamine oxidase.

(1) Preparation of Chromosomal DNA of Neocosmospora vasinfecta 474

100 ml of Sabouraud medium (glucose 4.0%, polypeptone 1.0%, pH 5.6) was poured into a 500 ml-volume Sakaguchi flask and sterilized by an autoclave, and Neocosmospora vasinfecta 474 was inoculated thereto and cultured with shaking at 25° C. for 4 days, followed by filtration of the culture medium using a No. 2 Filter Paper, to thereby collect the cells. The collected cells were frozen with liquid nitrogen and pulverized in a mortar to yield fine powder, and a chromosomal DNA solution was obtained using a DNeasy Plant Maxi Kit (manufactured by QIAGEN).

(2) Cloning of Ketoamine Oxidase Gene (a) Preparation of Radioactive DNA Probe

The ketoamine oxidase gene of Neocosmospora vasinfecta 474 was expected to have the homology to FOD923 gene. Accordingly, the above-described plasmid pPOSFOD923 including the FOD923 gene was cleaved with restriction enzymes NcoI and SacI, and a DNA fragment that has a size of about 1.4 kb and includes a ketoamine oxidase gene was separated. Then, the DNA fragment was used with BcaBEST Labeling Kit (manufactured by Takara Bio Inc.) and [α-32P] dCTP to prepare a radioactive DNA probe.

(b) Assay of DNA Fragment Containing Ketoamine Oxidase Gene by Southern Hybridization In order to create a gene library from the chromosomal DNA of Neocosmospora vasinfecta 474 obtained by operations described in (1), operations to cleave the chromosome with various restriction enzymes and to assay the length of a DNA fragment containing a target gene were performed. First, the chromosomal DNA of Neocosmospora vasinfecta 474 was cleaved with various restriction enzymes and subjected to electrophoresis in a 1.5% agarose gel, and the DNA was transferred from the agarose gel to a nylon membrane (Biodyne A: manufactured by PALL corporation). Next, the membrane was air-dried and immersed in a hybridization solution (0.1% Ficoll, 0.1% polyvinyl pyrrolidone, 0.1% bovine serum albumin, 0.75 M sodium chloride, 75 mM sodium citrate, 50 mM trisodium phosphate, 0.1% sodium dodecyl sulfate, 250 μg/ml salmon sperm DNA, and 50% formamide), and prehybridization was performed at 42° C. for 2 hours. After the prehybridization, the hybridization solution was exchanged for a new one, and the radioactive DNA probe created in (a) was added thereto, followed by a hybridization treatment overnight at 42° C. After the hybridization, the membrane was washed with a washing solution (75 mM sodium chloride, 7.5 mM sodium citrate, and 0.1% SDS) at 50° C. for 10 minutes and dried naturally. The dried membrane was placed on an X-ray film and exposed at −70° C. for 24 hours.

After the exposure, the film was developed, and there were observed the sizes of positive bands shown by the chromosomes cleaved with various restriction enzymes. As a result, it was found that a ketoamine oxidase gene is present on a DNA fragment having a size of about 8 kb which was obtained by cleavage with SacI, and a gene library was to be created using the fragment of chromosomal DNA having a size of 8 kb which was obtained by cleavage with SacI.

(c) Creation of Gene Library

The chromosomal DNA of Neocosmospora vasinfecta 474 obtained by operations described in (1) was cleaved with a restriction enzyme SacI, and agarose electrophoresis was performed to separate a DNA fragment having a size of about 8 kb. The resultant DNA fragment was ligated to pUC119 being dephosphorylated with alkaline phosphatase using a DNA Ligation Kit (manufactured by Takara Bio Inc.) after being cleaved with a restriction enzyme SacI. *Escherichia coli* JM 109 competent cell (manufactured by Takara Bio Inc.) was transformed with the resultant and cultured on LB agar medium (manufactured by Becton, Dickinson and Company) containing 50 μg/ml ampicillin, to thereby yield about 5,000 ampicillin-resistant colonies, which were used as a gene library.

(d) Screening of Recombinant *Escherichia coli* Including DNA Fragment Containing Ketoamine Oxidase Gene by Colony Hybridization The gene library obtained in (c) was replicated on a nylon membrane (Biodyne A: manufactured by PALL Corporation), and DNAs of the cells were fixed thereon according to an appended manual of the membrane. The DNA-fixed membrane was immersed in the hybridization solution shown in (b), and prehybridization was performed at 42° C. for 1 hour. After the prehybridization, the hybridization solution was exchanged for a new one, and the radioactive DNA probe created in (a) was added thereto, followed by a hybridization treatment overnight at 42° C. as well. After the hybridization, the membrane was washed with the washing solution shown in (b) at 50° C. for 10 minutes and dried naturally. The dried membrane was placed on an X-ray film and exposed at −70° C. for 24 hours. After the exposure, the film was developed, and 8 colonies showing positive signals were identified.

(e) Extraction of Recombinant Plasmid and Sequencing of Ketoamine Oxidase Gene

The colonies showing positive signals, which had been selected in (d), were inoculated in 1.5 ml of LB liquid medium (manufactured by Becton, Dickinson and Company) containing 50 μg/ml ampicillin and cultured with shaking at 37° C. for 16 hours, and plasmids were extracted. As a result, the plasmids derived from 8 colonies were found to have the same chromosomal DNA fragment. For one of those plasmids, a region having the homology to FOD923 gene was identified, and FOD474 gene was sequenced. SEQ ID NO: 9 shows the determined base sequence of FOD474 gene and amino acid sequence encoded thereby.

(3) Construction of *Escherichia coli* Expressing Ketoamine Oxidase Derived from *Neocosmospora vasinfecta* 474

In order to express FOD474 in *Escherichia coli*, there were synthesized: a primer P41 (SEQ ID NO: 10) added with the recognition sequence of a restriction enzyme BspHI on an initiating codon ATG of FOD474 gene; and a primer P42 (SEQ ID NO: 11) having a complementary sequence added with the recognition sequence of a restriction enzyme SacI on the site just behind the stop codon of a ketoamine oxidase gene.

Subsequently, 25 cycles of PCR were performed using a chromosomal DNA of *Neocosmospora vasinfecta* 474 as a template and P41 and P42 as primers, to thereby yield a DNA fragment having a size of about 1.4 kb and including FOD474 gene. The DNA fragment was cleaved with BspHI and SacI, and the resultant product was integrated into pPOS2 cleaved with NcoI and SacI to prepare a plasmid pPOSFOD474 where a ketoamine oxidase gene was integrated in the downstream of a pyruvate oxidase gene promoter. Meanwhile, a DNA fragment that has a size of about 1.4 kb and includes a FOD474 gene obtained by cleavage with XbaI and SacI, was integrated into plasmid pUC19 to thereby create a plasmid p119-FOD474 (FERM BP-08642), and sequenced. As a result, it was confirmed that mutation due to PCR had not occurred. *Escherichia coli* W3110 was transformed with the resultant pPOSFOD474 to construct *Escherichia coli* FAOD474 that expresses FOD474.

The plasmid p119-FOD474 (FERM BP-08642) has been deposited in International Patent Organism Depositary, National Institute of Advanced Industrial Science and Technology, Tsukuba Central 6, 1-1-1 Higashi, Tsukuba, Ibaraki, Japan on Feb. 24, 2004.

```
                                              (SEQ ID NO: 10)
P41   TTTTTTCATGACCACCCCCCGCAAAGAAACCACCGTCCTC (SEQ ID NO: 11)
P42   TTTTTGAGCTCATCTTGACTCGCTGTCCTGATCGTGCTTC
```

(4) Production of Ketoamine Oxidase Derived from *Neocosmospora vasinfecta* 474

Operations were performed using *Escherichia coli* FAOD474 in the same way as the above-described FOD923. Meanwhile, the determination reagent for FOD474 activity and method were also the same as those of the above-described FOD923.

Reference Example

Substrate Specificities of Ketoamine Oxidase Derived from *Curvularia clavata* YH923 (FERM BP-10009), Ketoamine Oxidase Derived from *Neocosmospora vasinfecta* 474, and Ketoamine Oxidase Derived from *Fusarium oxysporum* (Manufactured by Asahi Kasei Pharma Corporation)

20 μl of an enzyme solution was added to 200 μl of a reaction solution (50 mM Tris-HCl buffer (pH 7.5), 0.1% Triton X-100, 0.03% 4-aminoantipyrine, 0.02% TOOS, 5 U/ml peroxidase, and 2 mM substrate, the mixture was subjected to a reaction at 37° C. for 5 minutes, and 0.5 ml of 0.5% SDS was then added. Absorbance at 555 nm (A1) was determined and the same operations were performed using a reaction solution containing no substrate to determine absorbance (Ab) to thereby determining the reactivity from the difference (A1−Ab). Table 3 shows: the concentrations of used enzyme solutions of ketoamine oxidase derived from FOD923, FOD474, and *Fusarium oxysporum* (manufactured by Asahi Kasei Pharma Corporation: hereinafter also referred to as FOD2); used substrates; absorbance differences (A1−Ab); and relative activities (%).

Reference Example

Reaction for Releasing Fructosyl Valine from FVHL by Angiotensin-Converting Enzyme An angiotensin-converting enzyme derived from porcine kidney (manufactured by Sigma Corporation: hereinafter referred to as ACEP) and an angiotensin-converting enzyme derived from rabbit lung (manufactured by Sigma Corporation: hereinafter referred to as ACER) were dissolved in an enzyme-dissolving solution (100 mM HEPES (pH 8.3), 300 mM NaCl) so as to have a concentration of 20 U/ml, to thereby prepare an ACEP solution and ACER solution. Subsequently, 20 μl of the enzyme-dissolving solution, ACEP solution, and ACER solution were separately added to three tubes each containing 20 μl of 2 mM FVHL (manufactured by Peptide Institute, Inc.) solution, and the mixture was allowed to react at 37° C. for 1 hour. Then, 200 μl of a coloring solution (50 mM Tris-HCl (pH 7.5), 0.1% Triton X-100, 5 U/ml POD, 50 U/ml FOD2, and 0.02 mM DA-64) was added to each resultant, and the mixture was allowed to react at 37° C. for 5 minutes. Thereafter, 500 μl of 0.5% SDS was added to terminate the coloring reaction, and the absorbance at 730 nm was determined. The same reaction was performed except that distilled water was used instead of the 2 mM FVHL solution. Meanwhile, 200 μl of the coloring solution was added to 40 μl of an FV solution (0, 5, 10, 20, or 50 μM), and determination was performed in the same way as above. Then, a calibration curve was created, and the each amount of FV released from FVHL by ACEP and ACER was determined. The calibration curve for FV revealed in which absorbance differences at FV concentrations (μM) are 0.019 at 5 μM, 0.033 at 10 μM, 0.065 at 20 μM, and 0.0154 at 50 μM, respectively. Meanwhile, the absorbance difference showing FV released by the ACEP reaction was found to be −0.006, while the absorbance difference showing FV released by the ACER reaction was found to be 0.000. Those results revealed that FV is hardly released from FVHL by ACEP and ACER in a general reaction. Moreover, the absorbance difference in the case where the same determination was performed by adding the coloring solution to 40 μl of a sample (25 μM FV, 10 U/ml ACER) was found to be 0.062, so that it was found that ACER hardly inhibits a coloring reaction in the coloring solution.

the β-solution-supplemented well and the control solution-supplemented well larger than a difference in the absorbance between the α-solution-supplemented well and the control solution-supplemented well. Thus the protease of object was screened. The samples to be used include: carboxypeptidase B (manufactured by Sigma-Aldrich Corp.); carboxypeptidase W (manufactured by Wako Pure Chemical Industries, Ltd.); carboxypeptidase Y (manufactured by Oriental Yeast Co., Ltd.); protease (type XXVII nagase: manufactured by Sigma-Aldrich Corp.); protease (type VIII Subtilisin Carlsberg: manufactured by Sigma-Aldrich Corp.); protease (type XXIV Bacterial: manufactured by Sigma-Aldrich Corp.); Proteinase K (manufactured by Wako Pure Chemical Industries, Ltd.); neutral proteinase (manufactured by Toyobo Co., Ltd.); carboxypeptidase A (manufactured by Wako Pure Chemical Industries, Ltd.); thermolysin (manufactured by Wako Pure Chemical Industries, Ltd.); and distilled water. To confirm a degree of color development caused by a developing solution, 10 μl of 1 mM FVH (manufactured by Peptide Institute Inc.) and 1 mM FVL (manufactured by Peptide Institute Inc.) were placed in a well severally, followed by adding 50 μl of the control solution. The whole was incubated at 37° C. for 60 minutes. Then, 50 μl of distilled water and 50 μl of the developing solution were added and the whole was left at room temperature for 30 minutes, followed by the

TABLE 3

(VHLT disclosed as SEQ ID NO:37)

| | FOD923 | | | FOD474 | | | FOD2 | | | FOD923M | | |
|---|---|---|---|---|---|---|---|---|---|---|---|---|
| Substrate | enzyme conc. (U/ml) | absorbance difference (A1 − Ab) | relative activity (%) | enzyme conc. (U/ml) | absorbance difference (A1 − Ab) | relative activity (%) | enzyme conc. (U/ml) | absorbance difference (A1 − Ab) | relative activity (%) | enzyme conc. (U/ml) | absorbance difference (A1 − Ab) | relative activity (%) |
| FZK | 0.083 | 0.043 | 39 | 0.17 | 0.032 | 15 | 0.3 | 0.123 | 100 | 1.07 | 0.130 | 3.1 |
| FV | 0.025 | 0.217 | 556 | 0.05 | 0.289 | 445 | 1.5 | 0.109 | 18 | 0.016 | 0.290 | 464 |
| FVL | 0.17 | 0.009 | 3.4 | 5 | 0.059 | 0.91 | 150 | −0.001 | 0 | 1.07 | 0.050 | 1.2 |
| FVH | 0.05 | 0.078 | 100 | 0.17 | 0.221 | 100 | 150 | −0.001 | 0 | 0.032 | 0.125 | 100 |
| FVHL | 50 | 0.067 | 0.09 | 50 | 0.002 | 0 | 150 | 0.000 | 0 | 3.2 | 0.030 | 0.24 |
| FVHLT | 500 | 0.007 | 0.009 | 50 | 0.002 | 0 | 150 | 0.001 | 0 | 32 | 0.028 | 0.022 |
| β-glycated pentapeptide | 500 | 0.000 | 0 | 50 | 0.002 | 0 | 150 | 0.001 | 0 | 32 | 0.043 | 0.034 |
| α-glycated pentapeptide | 50 | 0.008 | 0.01 | 50 | 0.003 | 0 | 150 | −0.001 | 0 | 32 | 0.003 | 0.002 |

Example 1

Screening of Protease for Hemoglobin A1c Determination (pH 7.5)

A screening method is shown in which a protease that cleaves a glycated peptide from N-terminal-glycated pentapeptide of a hemoglobin β-chain without substantially cleaving a glycated amino acid or glycated peptide from N-terminal-glycated pentapeptide of a hemoglobin α-chain. Each 10 μl of a sample for screening was placed in 3 wells of a 96-well plate, respectively. Then, the first well was supplemented with 50 μl of an α-solution, the second well was supplemented with 50 μl of a β-solution, and the third well was supplemented with 50 μl of a control solution. After the plate was incubated at 37° C. for 60 minutes, 50 μl of distilled water and 50 μl of a developing solution were added, and the whole was left at room temperature for 30 minutes. Then, the absorbance at a measuring wavelength of 550 nm and a reference wavelength of 595 nm were determined using a Microplate Reader (model 550, manufactured by Bio-Rad), to select a sample having a difference in the absorbance between determination in a similar manner as described above. The results are shown in Table 4 and Table 5. The results confirmed that carboxypeptidase B, carboxypeptidase W, neutral proteinase, and thermolysin were the proteases that cleave a glycated peptide from an N-terminal glycated pentapeptide of a hemoglobin β-chain without substantially cleaving a glycated amino acid or glycated peptide from N-terminal glycated pentapeptide of a hemoglobin α-chain at pH 7.5.

<α-Solution>

50 mM Tris-HCl (pH7.5)

0.1% Triton X-100

0.2 mM α-Glycated pentapeptide (manufactured by Peptide Institute Inc.)

<α-Solution>

50 mM Tris-HCl (pH7.5)

0.1% Triton X-100

0.2 mM β-Glycated pentapeptide (manufactured by Peptide Institute Inc.)

<Control Solution>

50 mM Tris-HCl (pH7.5)

0.1% Triton X-100

<Developing Solution>

100 mM Tris-HCl (pH7.5)

0.09% 4-Aminoantipyrine (manufactured by Wako Pure Chemical Industries, Ltd.)

0.06% TODB (manufactured by Dojindo Laboratories)

15 U/ml Peroxidase (manufactured by Sigma-Aldrich Corp.)

18.75 U/ml FOD923

(TODB: N,N-bis(4-sulfobutyl)-3-methylaniline)

TABLE 4

RAW DATA (pH 7.5)

|  | α-Solution | β-Solution | control solution |
|---|---|---|---|
| carboxypeptidase B (100 U/ml) | 0.036 | 0.127 | 0.028 |
| carboxypeptidase W (520 U/ml) | 0.035 | 0.194 | 0.028 |
| carboxypeptidase Y (1010 U/ml) | 0.240 | 0.209 | 0.031 |
| protease type XXVII (810 U/ml) | 0.021 | 0.031 | 0.016 |
| protease type VIII (1100 U/ml) | 0.023 | 0.020 | 0.012 |
| protease type XXIV (1070 U/ml) | 0.018 | 0.033 | 0.010 |
| proteinase K (520 U/ml) | 0.031 | 0.077 | 0.017 |
| neutral proteinase (4000 U/ml) | 0.029 | 0.196 | 0.026 |
| distilled water | 0.028 | 0.039 | 0.028 |
| 1 mM fructosyl-Val-His | — | — | 0.188 |
| 1 mM fructosyl-Val-Leu | — | — | 0.198 |

TABLE 5

RAW DATA (pH 7.5)

|  | α-Solution | β-Solution | control solution |
|---|---|---|---|
| carboxypeptidase A (1000 U/ml) | 0.022 | 0.145 | 0.018 |
| thermolysin (75 kU/ml) | 0.053 | 0.249 | 0.055 |
| distilled water | 0.013 | 0.011 | 0.010 |
| 1 mM fructosyl-Val-His | — | — | 0.169 |
| 1 mM fructosyl-Val-Leu | — | — | 0.161 |

Example 2

Screening of Protease for Hemoglobin A1c Determination (pH 3.5)

A screening method is shown in which a protease that cleaves a glycated peptide from N-terminal-glycated pentapeptide of a hemoglobin β-chain without substantially cleaving a glycated amino acid or glycated peptide from N-terminal-glycated pentapeptide of a hemoglobin α-chain. Each 10 μl of a sample for screening was placed in 3 wells of a 96-well plate, respectively. Then, the first well was supplemented with 50 μl of an α-solution, the second well was supplemented with 50 μl of a β-solution, and the third well was supplemented with 50 μl of a control solution. After the plate was incubated at 37° C. for 60 minutes, 50 μl of pH-regulating solution and 50 μl of a developing solution were added, and the whole was left at room temperature for 30 minutes. Then, the absorbance at a measuring wavelength of 550 nm and a reference wavelength of 595 nm were determined using a Microplate Reader (model 550, manufactured by Bio-Rad), to select a sample having a difference in the absorbance between the β-solution-supplemented well and the control solution-supplemented well larger than a difference in the absorbance between the α-solution-supplemented well and the control solution-supplemented well. Thus the protease of object was screened. The samples to be used include: carboxypeptidase B (manufactured by Sigma-Aldrich Corp.); carboxypeptidase W (manufactured by Wako Pure Chemical Industries, Ltd.); carboxypeptidase Y (manufactured by Oriental Yeast Co., Ltd.); protease (type XXVII nagase: manufactured by Sigma-Aldrich Corp.); protease (type VIII Subtilisin Carlsberg: manufactured by Sigma-Aldrich Corp.); protease (type XXIV Bacterial: manufactured by Sigma-Aldrich Corp.); Proteinase K (manufactured by Wako Pure Chemical Industries, Ltd.); neutral proteinase (manufactured by Toyobo Co., Ltd.); and distilled water. To confirm a degree of color development caused by a developing solution, 10 μl of 1 mM FVH (manufactured by Peptide Institute Inc.) and 1 mM FVL (manufactured by Peptide Institute Inc.) were placed in a well severally, followed by adding 50 μl of the control solution. The whole was incubated at 37° C. for 60 minutes. Then, 50 μl of a pH-regulating solution and 50 μl of the developing solution were added and the whole was left at room temperature for 30 minutes, followed by the determination in a similar manner as described above. The results are shown in Table 6. The results confirmed that carboxypeptidase B was the protease that cleaves a glycated peptide from an N-terminal glycated pentapeptide of a hemoglobin β-chain without substantially cleaving a glycated amino acid or glycated peptide from N-terminal glycated pentapeptide of a hemoglobin α-chain at pH 3.5.

<α-Solution>

50 mM Acetate-sodium acetate (pH3.5)

0.1% Triton X-100

0.2 mM α-Glycated pentapeptide (manufactured by Peptide Institute Inc.)

<β-Solution>

50 mM Acetate-sodium acetate (pH3.5)

0.1% Triton X-100

0.2 mM β-Glycated pentapeptide (manufactured by Peptide Institute Inc.)

<Control Solution>

50 mM Acetate-sodium acetate (pH3.5)

0.1% Triton X-100

<pH-Regulating Solution>

100 mM CAPS—NaOH (pH 11.0)

(CAPS: 3-cyclohexylaminopropane sulfonic acid: manufactured by Dojindo Laboratories)

<Developing Solution>

100 mM Tris-HCl (pH7.5)

0.09% 4-aminoantipyrine (manufactured by Wako Pure Chemical Industries, Ltd.)

0.06% TODB (manufactured by Dojindo Laboratories)

15 U/ml Peroxidase (manufactured by Sigma-Aldrich Corp.)

18.75 U/ml FOD923

(TODB: N,N-bis(4-sulfobutyl)-3-methylaniline)

TABLE 6

RAW DATA (pH 3.5)

| | α-Solution | β-Solution | control solution |
|---|---|---|---|
| carboxypeptidase B (100 U/ml) | 0.063 | 0.147 | 0.060 |
| carboxypeptidase W (520 U/ml) | 0.211 | 0.184 | 0.032 |
| carboxypeptidase Y (1010 U/ml) | 0.195 | 0.206 | 0.034 |
| protease type XXVII (810 U/ml) | 0.025 | 0.021 | 0.019 |
| protease type VIII (1100 U/ml) | 0.019 | 0.018 | 0.016 |
| protease type XXIV (1070 U/ml) | 0.013 | 0.012 | 0.012 |
| proteinase K (520 U/ml) | 0.024 | 0.026 | 0.023 |
| neutral proteinase (4000 U/ml) | 0.036 | 0.040 | 0.035 |
| distilled water | 0.038 | 0.040 | 0.038 |
| 1 mM fructosyl-Val-His | — | — | 0.192 |
| 1 mM fructosyl-Val-Leu | — | — | 0.180 |

Example 3

Screening of Protease for Hemoglobin A1c Determination Derived from Microorganisms Various bacteria were cultured with shaking in Difco Lactobacilli MRS Broth (manufactured by Becton, Dickinson and Company), a MM medium (2.5% mannose, 2.5% beer yeast extract, pH7.0), and a YPG medium (2% glucose, 1% polypeptone, 2% yeast extract, 0.1% potassium dihydrogen phosphate, 0.05% magnesium sulfate heptahydrate, pH 7.0) at a temperature of from 28 to 30° C. for 1 to 7 days. Then, cells were removed by centrifugation from the culture solutions to obtain culture supernatants. A sample was prepared by diluting the obtained culture supernatants 10-fold with a 10 mM potassium phosphate buffer (pH7.5), and the determination was performed in a similar manner as Example 1. Table 7 shows the results from the bacteria cultured in MRS Broth, Table 8 shows the results from the bacterium cultured in the MM medium, and Table 9 shows the results from the bacterium cultured in the YPG medium (note that a reference wavelength was not determined in Table 9).

TABLE 7

RAW DATA (pH 7.5)

| | α-Solution | β-Solution | control solution |
|---|---|---|---|
| Bacillus sp. (FERM BP-08641) | 0.063 | 0.229 | 0.058 |
| distilled water | 0.040 | 0.033 | 0.049 |
| 1 mM fructosyl-Val-His | — | — | 0.218 |
| 1 mM fructosyl-Val-Leu | — | — | 0.238 |

TABLE 8

RAW DATA (pH 7.5)

| | α-Solution | β-Solution | control solution |
|---|---|---|---|
| Bacillus subtilis NBRC3037 | 0.062 | 0.198 | 0.066 |
| distilled water | 0.018 | 0.021 | 0.015 |
| 1 mM fructosyl-Val-His | — | — | 0.172 |
| 1 mM fructosyl-Val-Leu | — | — | 0.181 |

TABLE 9

RAW DATA (pH 7.5)

| | α-Solution | β-Solution | control solution |
|---|---|---|---|
| Lysobacter enzymogenes YK-366 (FERM BP-10010) | 0.170 | 0.696 | 0.168 |
| Aeromonas hydrophila NBRC3820 | 0.156 | 0.510 | 0.152 |

Example 4

Method of Purifying Protease Derived from Bacillus sp. ASP842 (FERM BP-08641) and Physicochemical Property Thereof Bacillus sp. ASP842 (FERM BP-08641) were cultured with shaking in four 500 ml-Erlenmeyer flasks which was supplemented with 150 ml of Difco Lactobacilli MRS Broth (manufactured by Becton, Dickinson and Company) at 28° C. for 3 days. Then, cells were removed from the culture solutions by centrifugation to obtain a culture supernatant (77 mU/ml, 560 ml). The culture supernatant was added with 210 g of ammonium sulfate and 8.4 g of perlite (manufactured by Toko Perlite Industry Co., Ltd.) and the whole was stirred. Then, precipitated proteases were collected by filtration with Filter Paper No. 5A (manufactured by Toyo-Roshi Kaisha, Ltd.) having a diameter of 90 mm. Subsequently, the precipitants was suspended in a 10 mM potassium phosphate buffer (pH 7.5), followed by filtration using Filter Paper 5A (manufactured by Toyo-Roshi Kaisha, Ltd.), thereby obtaining a filtrate having a protease activity (215 mU/ml, 90 ml). The filtrate was subjected to dialysis against 5 L of a 10 mM potassium phosphate buffer (pH7.5). The dialyzed protease solution was adsorbed to DEAE-Sepharose FF (manufactured by Amersham) in a column (26φ×94 mm) equilibrated with a 10 mM potassium phosphate buffer (pH 7.5), and a fraction having protease activity (217 mU/ml, 54 ml) was obtained by elution with NaCl gradient of 0 M to 0.5 M. After ammonium sulfate was added to be the concentration of 1 M in the fraction, the fraction was adsorbed to Phenyl-Sepharose CL-4B (manufactured by Amersham) in a column (15φ×150 mm) equilibrated with 1 M ammonium sulfate and a 10 mM potassium phosphate buffer (pH 7.5). Then, a fraction having protease activity (237 mU/ml, 18 ml) was eluted with a gradient of 1M ammonium sulfate, 0% ethylene glycol to 0M ammonium sulfate, 20% ethylene glycol, and concentrated with Amicon Ultra 10000 MWCO (manufactured by Millipore), thereby to obtain a purified protease (13.9 U/ml, 0.42 ml). The reagent and method for determining the activity of the protease of the invention are described below.

<Determination Reagent>

50 mM Tris-HCl (pH7.5)

2 mM Calcium chloride 0.1% Triton X-100

0.03% 4-Aminoantipyrine 0.02% TOOS

5 U/ml Peroxidase

5 U/ml FOD923

0.25 mM Substrate

<Determination Method>

0.2 ml of a determination reagent was placed in a test tube and preheated at 37° C. for 5 minutes. Then, 0.02 ml of an enzyme solution was added thereto and a reaction was carried out for 10 minutes. After the reaction, 0.5 ml of 0.5% SDS was added thereto to terminate the reaction. Then, absorbance at the wavelength 555 nm (Aa) was determined. In addition, distilled water was added as a blank instead of the enzyme solution to determine absorbance (Ab) by performing a similar operation. An enzymatic activity was obtained from a difference between the absorbance (Aa) and the absorbance of a blank (Ab) (Aa−Ab). One unit of the enzyme activity was defined as an amount of an enzyme that allows generating 1 µmol of hydrogen peroxide per minute at 37° C. Note that, β-glycated pentapeptide was used as a substrate.

<Physicochemical Properties>

(1) Substrate Specificity

Determination was carried out according to <Determination Method> in Example 4, except that the concentration of FOD923 was changed to 50 U/ml and 0.25 mM β-glycated pentapeptide, 0.25 mM α-glycated pentapeptide, 0.03 mM FVH, 0.03 mM FVL, and 0.03 mM FV were used as substrate. In addition, similar determination in which FOD923 is changed to FOD2 was performed. Furthermore, similar determination was performed using neutral protease (manufactured by Toyobo Co., Ltd.) for comparison. Table 10 shows difference in the obtained absorbances (Aa−Ab). The results confirmed that the protease of the invention cleaved FVH from β-glycated pentapeptide without cleaving a glycated amino acid or glycated peptide from α-glycated pentapeptide, in the same manner as neutral protease (manufactured by Toyobo Co., Ltd.) cleaves.

TABLE 10

| | FOD 923 | | | FOD 2 | | |
|---|---|---|---|---|---|---|
| RAW DATA | DW | neutral proteinase | protease ASP842 | DW | neutral proteinase | protease ASP842 |
| β-glycated pentapeptide | 0.044 | 0.417 | 0.258 | 0.030 | 0.028 | 0.029 |
| α-glycated pentapeptide | 0.036 | 0.036 | 0.034 | 0.025 | 0.020 | 0.025 |
| FVH | 0.163 | 0.159 | 0.150 | 0.024 | 0.044 | 0.024 |
| FVL | 0.172 | 0.173 | 0.165 | 0.024 | 0.024 | 0.022 |
| FV | 0.152 | 0.161 | 0.162 | 0.216 | 0.209 | 0.217 |
| DW | 0.030 | 0.031 | 0.030 | 0.026 | 0.022 | 0.024 |

(2) Optimum pH

FIG. 2 shows the results of determination according to the determination method described in Example 4, except that 50 mM Tris-HCl (pH 8.0, 8.5), 50 mM PIPES (pH 6.0, 6.5, 7.0) and 50 mM citrate-sodium citrate (pH 5.5, 6.0, 6.5) were used instead of 50 mM Tris-HCl (pH 7.5) respectively and 0.25 mM substrate was changed to 0.1 mM β-glycated pentapeptide. The results confirmed that pH of about 6.0 is optimum.

(3) pH Stability

Figure 3:
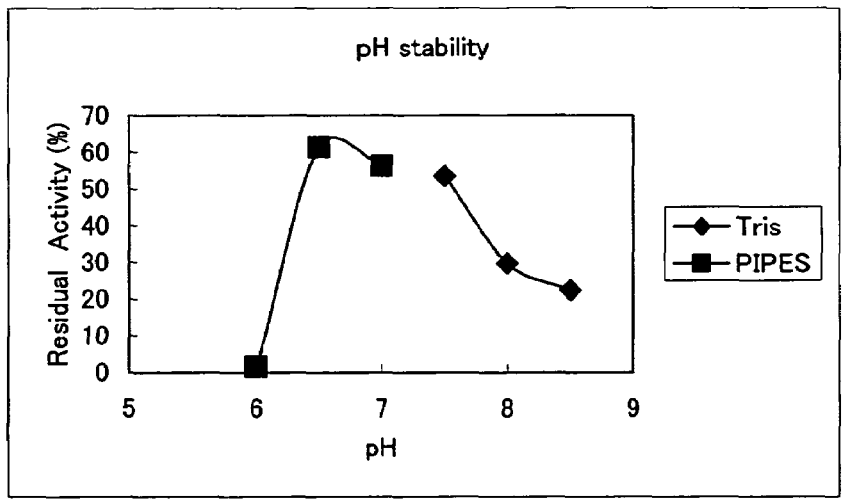
FIG. 3 shows the pH stability of a protease derived from *Bacillus* sp. ASP 842.

The enzyme was treated with 50 mM Tris-HCl (pH 7.5, 8.0, 8.5) and 50 mM PIPES (pH 6.0, 6.5, 7.0) at 50° C. for 20 minutes and a residual activity thereof was determined. FIG. 3 shows the results.

(4) Optimum Temperature

Figure 4:
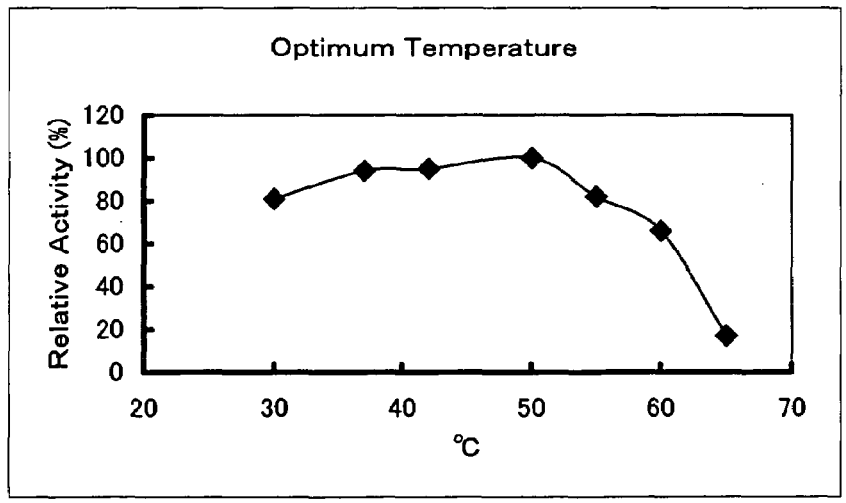
FIG. 4 shows the optimum temperature for a protease derived from *Bacillus* sp. ASP 842.

20 µl of a protease solution were added to 100 µl of a reaction solution (50 mM Tris-HCl (pH 7.5), 2 mM calcium chloride, 0.1% Triton X-100, 2.5 mM β-pentapeptide). A reaction was carried out at 30, 37, 42, 50, 55, 60, and 65° C. (10 minutes for each temperature) followed by the termination of the reaction by adding 5 µL of 0.5 M EDTA. Then, 95 µl of a developing solution (0.03% 4-aminoantipyrine, 0.02% TOOS, 50 U/ml peroxidase, 10.5 U/ml FOD923) was added thereto and a reaction was carried out at 37° C. for 5 minutes. Subsequently, 95 µl of 0.5% SDS was added thereto and absorbance at 555 nm was determined, thereby to determine the optimum temperature. FIG. 4 shows the results.

(5) Thermal Stability

Figure 5:
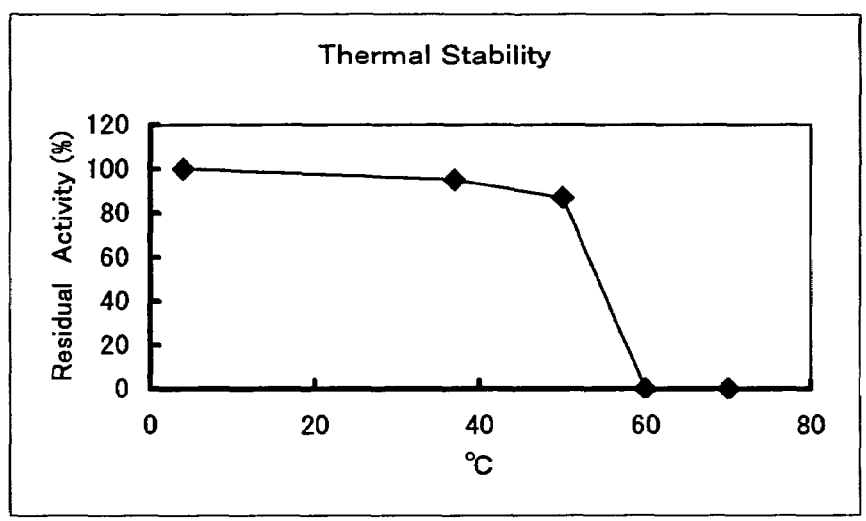
FIG. 5 shows the thermal stability of a protease derived from *Bacillus* sp. ASP 842.

The protease was placed in 50 mM Tris-HCl (pH 7.5) and treated at 4, 37, 50, 60, and 70° C. (10 minutes for each temperature), followed by determining residual activities. FIG. 5 shows the results.

(6) Molecular Weight
   35 kDa (SDS-PAGE)
   32,721 Da (MALDI-TOF MASS analysis)

Example 5

Culture Method and Purification Method for Protease Derived from *Aeromonas hydrophila* NBRC 3820 Strain and Enzymological Properties Thereof <Culture Method>

Each 100 ml of a YPG medium (2.0% glucose, 1.0% polypeptone, 2.0% yeast extract, 0.1% KH2PO4, 0.05% MgSO4.7H2O, pH 7.0) was placed in ten 500 ml-Sakaguchi flasks and sterilized, followed by inoculating *Aeromonas hydrophila* NBRC 3820. The whole was cultured with shaking at 30° C. for 2 days.

<Purification Method>

The obtained culture solution was subjected to centrifugation. Ammonium sulfate was added to the obtained culture supernatant to be 40% saturated and the centrifuged supernatant was provided to a column of Butyl Toyopearl 650M (30φ×150 mm, manufactured by Tosoh Corp.) equilibrated with 0.1 M Tris-HCl buffer (pH 7.3) in which 40% saturated ammonium sulfate was added. Washing was performed with 0.1 M Tris-HCl buffer (pH 7.3) containing ammonium sulfate added to be 10% saturated, and elution was performed with 0.1 M Tris-HCl buffer (pH 7.3). After an active fraction of the eluate was dialyzed against a 50 mM Tris-HCl buffer (pH 7.3), the active fraction was provided to a column of DEAE-Sepharose Fast Flow (30φ×150 mm, manufactured by Amersham) equilibrated with the same buffer and was subjected to elution with NaCl having a gradient of 0 to 0.5 M. Ammonium sulfate was added to an active fraction of the eluate to be 40% saturated. The whole was provided to a column of Butyl-Toyopearl 650 M (18φ×150 mm, manufactured by Tosoh Corp.) equilibrated with 0.1 M Tris-HCl buffer (pH 7.3) in which 40% saturated ammonium sulfate was added, and was subjected to elution with saturated ammonium sulfate having a linear gradient of 40% to 0%. Active fractions were collected and dialyzed against distilled water thereby obtaining a purified protease. Table 11 shows procedures of the purification.

The activity of the enzyme of the invention was determined as follows. 0.45 ml of a 100 mM Tris-HCl buffer (pH 7.5) in which β-glycated pentapeptide was dissolved to be 0.5 mM was placed in a cell having an optical path length of 1 cm. The whole was preheated at 37° C. for 5 minutes followed by adding 0.05 ml of an enzyme solution, and a reaction was carried out for 10 minutes. After the reaction, 0.5 ml of a determination reagent (a 100 mM Tris-HCl buffer (pH 7.5) containing 0.04% TOOS, 0.06% 4-aminoantipyrine, peroxidase 10 U, and ketoamine oxidase 10 U derived from *Curvularia clavata* YH923) was added thereto. After color was developed for 2 minutes, 2 ml of 0.5% SDS was added to terminate the reaction, then absorbance at the wavelength 550 nm (Aa) was determined. In addition, absorbance (Ab) was determined by performing a similar operation using various buffer solutions containing no substrates as blank. An enzymatic activity was obtained from a difference between the absorbance (Aa) and the absorbance of a blank (Ab) (Aa−Ab).

TABLE 11

Purification of protease derived from *Aeromonas hydrophila* NBRC3820

| purification steps | total protein ($A_{280}$) | total activity (U) | specific activity (U/$A_{280}$) | recovery (%) |
|---|---|---|---|---|
| 40-80% ammonium sulfate precipitation | 32,500 | 455 | 0.01 | 100.0 |
| Butyl-Toyopearl 650M | 31.5 | 302 | 9.60 | 66.5 |
| DEAE-sepharose FF | 13.4 | 132 | 9.82 | 29.0 |
| Butyl-Toyopearl 650M | 11.4 | 112 | 9.85 | 24.7 |

<Physicochemical Properties>

(1) Actions

Table 12 shows actions of the protease derived from *Aeromonas hydrophila* NBRC 3820 of the present invention on α-glycated pentapeptide and β-glycated pentapeptide. Concentrations of respective substrates during the reaction were set to be 0.25 mM. The protease derived from *Aeromonas hydrophila* NBRC 3820 (1.0 U) was added thereto and a reaction was carried out at 30° C. for 5 to 60 minutes. Then, the reaction solution was brought into a protein sequencer (manufactured by Shimadzu Corp.) and an amino acid sequence at N-terminal of the peptide produced by the action of the protease was determined.

As the result, the protease derived from *Aeromonas hydrophila* NBRC 3820 did not act on α-glycated pentapeptide, while it cleaved a peptide bond between histidine and leucine in β-glycated pentapeptide and produced FVH and leucyl-threonyl-proline (LTP).

Figure 6:
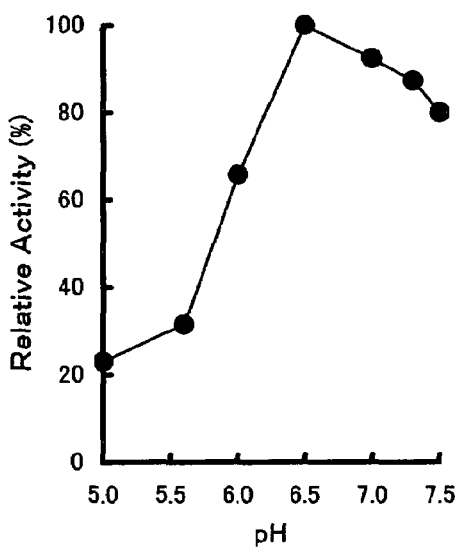
FIG. 6 shows the optimum pH for a protease derived from *Aeromonas hydrophila* NBRC 3820.

(2) Optimum pH 0.45 ml of various buffers having pH of 3.0 to 11.0 (a 100 mM acetate buffer with pH 3-5, a 100 mM citrate buffer with pH 5-7, a 100 mM Tris-HCl buffer with pH 7-9, and a 100 mM borate buffer with pH 9-11) in which β-glycated pentapeptide was dissolved to be 0.5 mM respectively were placed in cells having an optical path length of 1 cm. The whole was preheated at 37° C. for 5 minutes followed by adding 0.05 ml of an enzyme solution, and a reaction was carried out for 10 minutes. After the reaction, 0.5 ml of a determination reagent (a 100 mM Tris-HCl buffer (pH 7.5) containing 0.04% TOOS, 0.06% 4-aminoantipyrine, peroxidase 10 U, and ketoamine oxidase 10 U derived from *Curvularia clavata* YH923) was added thereto. After color was developed for 2 minutes, 2 ml of 0.5% SDS was added to terminate the reaction, then absorbance at the wavelength 550 nm (Aa) was determined. In addition, absorbance (Ab) was determined by performing a similar operation using various buffer solutions containing no substrates as blank. An enzymatic activity was obtained from a difference between the absorbance (Aa) and the absorbance of a blank (Ab) (Aa−Ab). FIG. 6 shows the results.

(3) pH Stability

Figure 7:
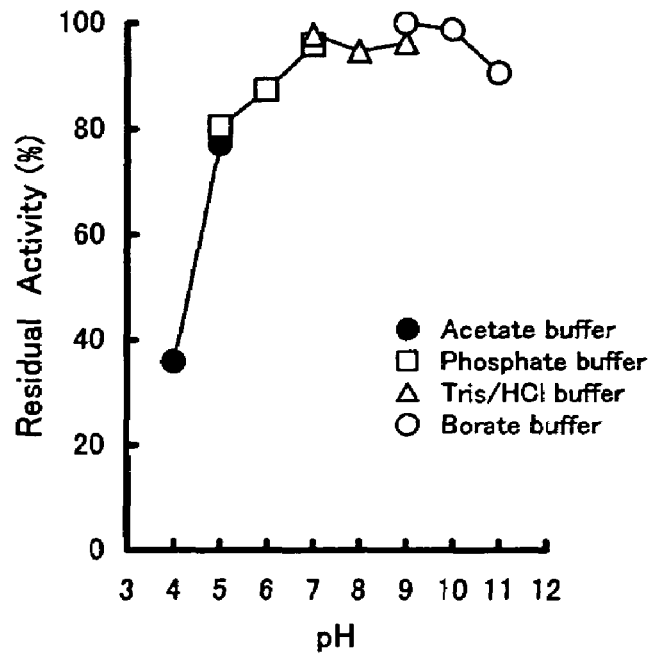
FIG. 7 shows the pH stability of a protease derived from *Aeromonas hydrophila* NBRC 3820.

The enzyme solution was treated with 10 mM various buffers at 4° C. for 24 hours and residual activities thereof were determined according to the activity determination method described in <Purification Method>. FIG. 7 shows the results.

Figure 8:
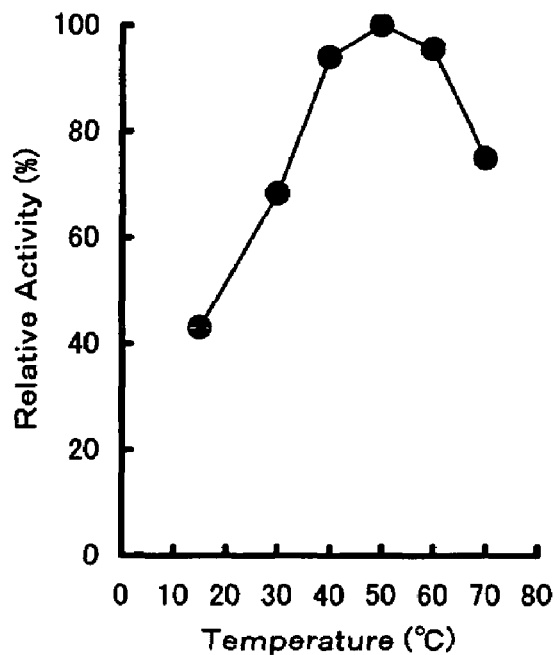
FIG. 8 shows the optimum temperature for a protease derived from *Aeromonas hydrophila* NBRC 3820.

(4) Optimum Temperature 0.45 ml of a 100 mM Tris-HCl buffer (pH 7.5) in which β-glycated pentapeptide was dissolved to be 0.5 mM was placed in a cell having an optical path length of 1 cm. The whole was preheated at from 15 to 70° C. for 5 minutes followed by adding 0.05 ml of an enzyme solution, and a reaction was carried out for 10 minutes. After the reaction, the whole was cooled on ice. Then, 0.5 ml of a determination reagent (a 100 µM Tris-HCl buffer (pH 7.5) containing 0.04% TOOS, 0.06% 4-aminoantipyrine, peroxidase 10 U, and ketoamine oxidase 10 U derived from *Curvularia clavata* YH923) was added thereto. After color was developed for 2 minutes, 2 ml of a 0.5% SDS solution was added to terminate the reaction, then absorbance at the wavelength 550 nm (Aa) was determined. In addition, absorbance (Ab) was determined by performing a similar operation using various buffer solutions containing no FVH as blank. An enzymatic activity was obtained from a difference between the absorbance (Aa) and the absorbance of a blank (Ab) (Aa−Ab). FIG. 8 shows the results for an optimum temperature obtained by changing temperature from 15 to 70°.

(5) Thermal Stability

Figure 9:
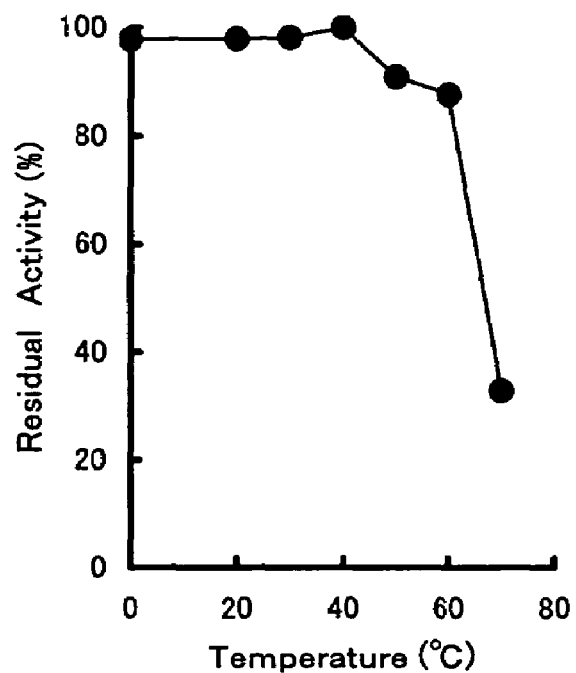
FIG. 9 shows the thermal stability of a protease derived from *Aeromonas hydrophila* NBRC 3820.

The enzyme solution was treated with a 100 mM Tris-HCl buffer (pH 7.5) for 30 minutes for each temperature and residual activities thereof were determined according to the activity determination method for the enzyme described above. FIG. 9 shows the results.

(6) Molecular Weight

The molecular weight of the enzyme of the invention was obtained by gel filtration using YMC-Pack Diol-200G (6.0φ× 300 mm, manufactured by YMC). Bovine serum albumin, ovalbumin, and a soybean trypsin inhibitor (all manufactured by Sigma Corp.) were used as standard proteins. As a result, the molecular weight was about 33,000.

SDS-PAGE (sodium dodesyl sulfate-polyacrylamide gel electrophoresis) using 10% gel of Laemmli's method resulted in a molecular weight of about 33,000. Note that, SDS-PAGE Standard Low (manufactured by Bio-Rad) was used as a standard protein.

The above results revealed that the protease of the invention derived from *Aeromonas hydrophila* NBRC 3820 is a monomer.

(7) Amino Acid Sequence of N-Terminal Portion

According to the above method, a purified enzyme obtained from a culture solution of *Aeromonas hydrophila* NBRC 3820 was dissolved in distilled water and subjected to analysis using an N-terminal sequencer (PPSQ-21, manufactured by Shimadzu Corp.). The obtained sequence was as shown by SEQ ID NO: 12. Homology search was conducted for the obtained amino acid sequence of the N-terminal portion with known proteases, resulting that the obtained amino acid sequence of the N-terminal portion has 98% homology to an elastase derived from *Aeromonas hydrophila*.

```
                                          (SEQ ID NO: 12)
Val Asp Ala Thr Gly Pro Gly Gly Asn Val Lys Thr

Gly Lys Tyr Phe Tyr Gly
```

(8) Partial Amino Acid Sequence

Segments of the enzyme were obtained to determine its sequence, according to "Method of purifying minor proteins for microsequence, p 48-52, 1992, Yodosha Co., Ltd.", using 60 g of a freeze-dried product of the purified enzyme obtained from the culture solution of *Aeromonas hydrophila* NBRC3820 according to the above method. That is, 50 μl of 45 mM dithiothreitol was added and the whole was treated at 50° C. for 15 minutes, followed by adding 5 μl of 100 mM iodoacetoamide and being left for 15 minutes. Subsequently, 140 μl of distilled water and 1.0 μg of endoproteinase Lys-C (manufactured by Roche Diagnostics) were added thereto and the whole was incubated overnight at 37° C. The segmented enzymes were separated by HPLC thereby obtaining respective enzyme fragments. The respective fragments were subjected to analysis using the N-terminal sequencer (PPSQ-21, manufactured by Shimadzu Corp.). The following SEQ ID NOS: 13 and 14 show the obtained sequences. The two obtained partial amino acid sequences were completely matched with the amino acid sequence of the elastase derived from of *Aeromonas hydrophila*, respectively.

```
                                          (SEQ ID NO: 13)
     Leu Asp Val Ala Ala His Glu Val Ser His (SEQ ID NO: 14)
     Phe Gly Asp Gly Ala Thr
```

Table 12 shows the above-described properties of the protease derived from *Aeromonas hydrophila* NBRC 3820.

TABLE 12

|  | *Aeromonas hydrophila* NBRC3820 |
|---|---|
| Molecular weight (Da) |  |
| SDS-PAGE | 33,000 |
| Optimal reaction pH (37 degree C., 10 min) | pH 6.5-7.0 |
| pH stability (5 degree C., 24 h) | pH 6.0-11.0 |
| Optimal reaction temperature (pH 7.5, 10 min) | 50 degree C. |
| Thermal stability (pH 7.5, 10 min) | ~60 degree C. |
| Substrate specificity | ↓ |
| F-VHLTP (β-chain) (SEQ ID NO: 36) | 100 |
|  | ↓ |
| F-VHLTP (β-chain) (SEQ ID NO: 36) | N.D. |
|  | ↓ |
| F-VLSPA (α-chain) (SEQ ID NO: 50) | N.D. |
| Elastin degradation | + |
| N-terminal amino acid sequence | VNATGPGGNVKTGKYFYG (SEQ ID NO: 48) |
| Reaction pattern | ↓ |
|  | Frc-Val-His-Leu-Thr-Pro (SEQ ID NO: 36) |

Example 6

Culture Method and Purification Method for Protease Derived from *Lysobacter enzymogenes* YK-366 (FERM BP-10010) Strain and Enzymological Properties thereof <Purification Method>

Active fractions were collected by the same method as the production method and purification method described in Example 5 and dialyzed against distilled water to thereby obtaining a purified protease. Table 13 shows process of the purification. An activity determination method to be performed was the same as the method in Example 5.

TABLE 13

Purification of protease derived from *Lysobacter enzymogenes* YK-366

| purification steps | total protein ($A_{280}$) | total activity (U) | specific activity ($U/A_{280}$) | recovery (%) |
|---|---|---|---|---|
| 40-80% ammonium sulfate precipitation | 39,500 | 524 | 0.01 | 100.0 |
| Butyl-Toyopearl 650M | 36.8 | 261 | 7.09 | 49.8 |
| DEAE-sepharose FF | 5.6 | 49 | 8.75 | 9.4 |
| Butyl-Toyopearl 650M | 5.1 | 41 | 8.04 | 7.8 |

<Physicochemical Properties>

(1) Actions

Table 14 shows actions of the protease derived from *Lysobacter enzymogenes* YK-366 of the present invention on α-glycated pentapeptide and β-glycated pentapeptide. The action of the protease derived from *Lysobacter enzymogenes* YK-366 on α-glycated pentapeptide and β-glycated pentapeptide was investigated according to the method described in (1) of Example 5. As a result, the protease derived from *Lysobacter enzymogenes* YK-366 did not act on α-glycated pentapeptide, while it cleaved a peptide bond between histidine and leucine in β-glycated pentapeptide, and produced FVH and LTP.

(2) Optimum pH

Figure 10:
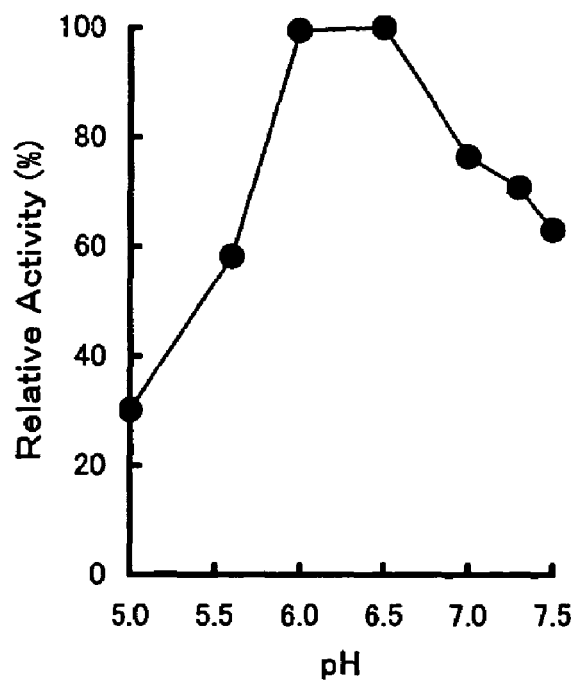
FIG. 10 shows the optimum pH for a protease derived from *Lysobacter enzymogenes* YK-366.

FIG. 10 shows the results obtained by investigating the optimum pH of the protease derived from *Lysobacter enzymogenes* YK-366 according to the method described in (2) of Example 5.

(3) pH Stability

Figure 11:
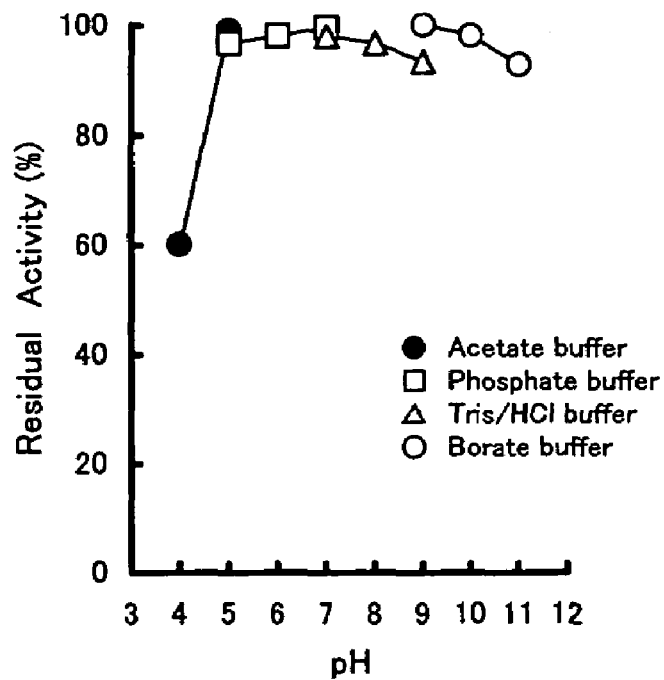
FIG. 11 shows the pH stability of a protease derived from *Lysobacter enzymogenes* YK-366.

FIG. 11 shows the results obtained by investigating the pH stability of the protease derived from *Lysobacter enzymogenes* YK-366 according to the method described in (3) of Example 5.

(4) Optimum Temperature

Figure 12:
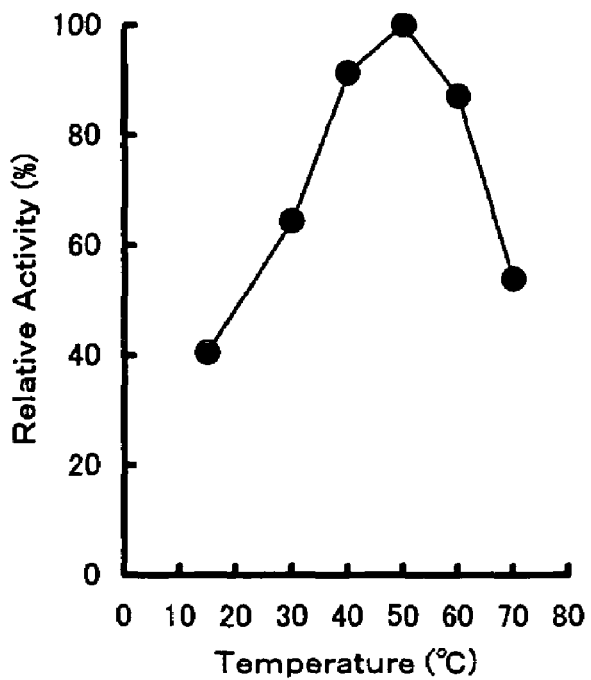
FIG. 12 shows the optimum temperature for a protease derived from *Lysobacter enzymogenes* YK-366.

FIG. 12 shows the results obtained by investigating the optimum temperature of the protease derived from *Lysobacter enzymogenes* YK-366 according to the method described in (4) of Example 5.

(5) Thermal Stability

Figure 13:
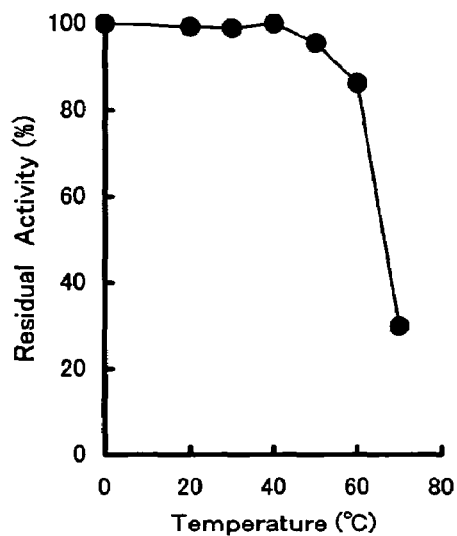
FIG. 13 shows the thermal stability of a protease derived from *Lysobacter enzymogenes* YK-366.

FIG. 13 shows the results obtained by investigating the thermal stability of the protease derived from *Lysobacter enzymogenes* YK-366 according to the method described in (5) of Example 5.

(6) Molecular Weight

As the results of obtaining the molecular weight by the gel filtration and SDS-PAGE according to the method described in (6) of Example 5, the molecular weight was about 35,000 respectively.

The above result revealed that the protease of the present invention derived from *Lysobacter enzymogenes* YK-366 is a monomer.

(7) Amino Acid Sequence of N-Terminal Portion

According to the above method, the purified enzyme obtained from the culture solution of *Lysobacter enzymogenes* YK-366 was dissolved in distilled water and subjected to analysis using the N-terminal sequencer (PPSQ-21, manufactured by Shimadzu Corp.). The obtained sequence was as shown by SEQ ID NO: 15.

```
                                        (SEQ ID NO: 15)
Ala Leu Val Gly Thr Gly Pro Gly Gly Asn Gln Lys

Thr Gly Gln Tyr Glu Tyr Gly Thr
```

(8) Partial Amino Acid Sequence

Segments of the enzyme were obtained to determine sequence thereof, according to a conventional method ("Method of purifying minor proteins for microsequence, p 48-52, 1992, Yodosha Co., Ltd."), using 60 g of a freeze-dried product of the purified enzyme obtained from the culture solution of *Lysobacter enzymogenes* YK-366 according to the above method. That is, 50 µl of 45 mM dithiothreitol was added and the whole was treated at 50° C. for 15 minutes, followed by adding 5 µl of 100 mM iodoacetoamide and being left for 15 minutes. Subsequently, 140 µl of distilled water and 1.0 µg of endoproteinase Lys-C (manufactured by Roche Diagnostics) were added thereto and the whole was incubated overnight at 37° C. The segmented enzymes were separated by HPLC thereby obtaining respective enzyme fragments. The respective fragments were subjected to analysis using an N-terminal sequencer (PPSQ-21, manufactured by Shimadzu Corp.). The following SEQ ID NOS: 16 and 17 show the obtained sequences.

```
Tyr Ser Xaa Asn Tyr Glu Asn Ala    (SEQ ID NO: 16)

Phe Gly Asp Gly Ala Thr            (SEQ ID NO: 17)
```

Table 14 shows the above-described properties of the protease derived from *Lysobacter enzymogenes* NBRC 3820.

TABLE 14

| | *Lysobacter enzymogenes* YK-366 |
|---|---|
| Molecular weight (Da) | |
| SDS-PAGE | 35,000 |
| Optimal reaction pH (37 degree C., 10 min) | pH 6.0-6.5 |
| pH stability (5 degree C., 24 h) | pH 5.0-11.0 |
| Optimal reaction temperature (pH 7.5, 10 min) | 50 degree C. |
| Thermal stability (pH 7.5, 10 min) | ~60 degree C. |
| Substrate specificity |  |

TABLE 14-continued

| | *Lysobacter enzymogenes* YK-366 |
|---|---|
| F-VHLTP (β-chain) (SEQ ID NO: 36) | 100 |
| ↓ | |
| F-VHLTP (β-chain) (SEQ ID NO: 36) | N.D. |
| ↓ | |
| F-VLSPA (α-chain) (SEQ ID NO: 50) | N.D. |
| Elastin degradation | + |
| N-terminal amino acid sequence | ALVGTGPGGNQKTGQYEYGT (SEQ ID NO: 49) |
| Reaction pattern | ↓ |
| | Frc-Val-His-Leu-Thr-Pro (SEQ ID NO: 36) |

Example 7

Acquisition of Mutant Ketoamine Oxidase having Decreased Activity on FZK by Gene Modification <Construction of Mutant Library of Ketoamine Oxidase Derived from *Curvularia clavata* YH923>

Construction of a mutant library of FOD923 was created from error-prone PCR that utilizes misreading of DNA polymerase. The error-prone PCR employed pPOSFOD923 described in the above reference example as a template, was performed using a P51 primer and a P52 primer (given in the following SEQ ID NOS: 18 and 19) and Ready-To-Go PCR beads (manufactured by Amersham) such that magnesium chloride was added to be a final concentration of 2.5 mM. PCR was conducted under the cycle conditions of: 94° C.×40 seconds, 55° C.×30 seconds, 72° C.×1 minute; and 25 cycles.

```
                                    (SEQ ID NO: 18)
P51     ACACCATGGCGCCCTCAAGAGCAAACACT (SEQ ID NO: 19)
P52     TTCGAGCTCTATAACTTGGACTTGACAACATCGTC
```

An amplified PCR product was purified using a GFX PCR DNA and Gel Band Purification-kit (manufactured by Amersham).

0.2 µg of the purified PCR product was digested by restriction enzymes NcoI and SacI and collected by ethanol precipitation. Meanwhile, 0.5 µg of pPOSFOD923 was also digested by the same restriction enzymes, and a DNA fragment of 2.9 kbp containing no ketoamine oxidase gene was separated by agarose-gel electrophoresis and collected using a GFX PCR DNA and Gel Band Purification-kit. Both DNA fragments described above were subjected to a reaction using a Ligation High kit (manufactured by Toyobo Co., Ltd.) at 16° C. for 30 minutes to ligate each other. By using the ligated DNA fragment, a competent cell of *Escherichia coli* JM109 was transformed. The transformant was spread on an LB agar medium containing 50 µg/ml of ampicillin and static cultured at 37° C. until colonies grew to about 1-2 mm.

<Screening of Mutant Ketoamine Oxidase Having Decreased Activity on FZK>

100 µl of a preliminary sterilized expression medium (a medium containing 3% of sorbitol, 1.5% of polypeptone, 1.5% of yeast extract, and 50 µg/ml of ampicillin and adjusted to pH 7.0) was added to a 96-well microplate. Grown transformants were inoculated thereto and cultured overnight at 30° C. After the termination of the culture, each 5 µl of the culture solution was dispensed into two wells of a 96-well plate and 50 µl of a determination reagent (a 50 mM Tris-HCl buffer (pH 7.5) containing 1 mM FVH or FZK, 0.02% TOOS, 0.02% 4-aminoantipyrine and 10 U/ml peroxidase) was added to each well, and a reaction was carried out at 30° C. for 10-60 minutes. 150 µl of 0.5% SDS was added thereto to terminate the reaction and absorbance was determined at 550 nm using a Microreader (model 450, manufactured by Bio-Rad). From the constructed mutant library, a recombinant which produces ketoamine oxidase that act on FVH but has a decreased activity on FZK was selected. As a result of the screening, 923-F1 and 923-F2 were obtained as favorable mutant strains. Ketoamine oxidase genes harbored by those mutant strains were sequenced and resulted that mutations were introduced in the bases indicated by Table 15.

TABLE 15

| | gene mutation | corresponding amino acid mutation | restriction enzyme used | FZK/FVH |
|---|---|---|---|---|
| FOD923 | — | — | — | 1.1 |
| 923-F1 | 185 g→a | 62 R→H | — | 0.24 |
| 923-F2 | 172 a→g | 58 I→V | — | 0.025 |
| | 185 g→a | 62 R→H | | |
| | 988 t→c | 330 F→L | | |
| 923-I58V | 172 a→g | 58 I→V | XbaI | 0.12 |
| 923-F330L | 988 t→c | 330 F→L | NcoI Bst1107I | 0.95 |
| 923-Fro2 | 172 a→g | 58 I→V | NcoI | 0.025 |
| | 185 g→a | 62 R→H | Bst1107I | |

Note:
The described base numbers are counted from the position 471, which is considered as the first position, in the base sequence according to SEQ ID NO: 1, except intron sites.

<Confirmation of Substrate Specificity of Mutant Ketoamine Oxidase>

Colonies from the selected strain was inoculated to 5 ml of an LB medium (containing 50 µg/ml of ampicillin) and cultured with shaking at 30° C. for 20 hours. Cells were collected from the culture solution after the termination of the culture by centrifugation, were suspended in 5 ml of a 0.1 M Tris-HCl buffer (pH 7.5), and were solubilized by ultrasonic breaking. The solubilized solution was subjected to centrifugation (8,000 rpm, 10 minutes) and the obtained supernatant was used as a crude enzyme solution of ketoamine oxidase. Specificity (a specific activity of the activity on FZK to the activity on FVH; indicated as FZK/FVH hereinafter) was obtained using those crude enzyme solutions and FVH and FZK as substrates according to the activity determination method described in <Screening of Mutant Ketoamine Oxidase having Decreased Action on FZK>. As a result, FZK/FVH ratios of 923-F1 and 923-F2 were 0.24 and 0.025 respectively as shown in Table 15, revealed that the activities on FZK of the mutant enzymes have largely decreased.

<Identification of Effective Mutational Position>

To identify an effective mutational position that affected on improvement of the above-described substrate specificity, mutant ketoamine oxidase having introduced the point mutations indicated in Table 15 was created by the following method.

Figure 14:
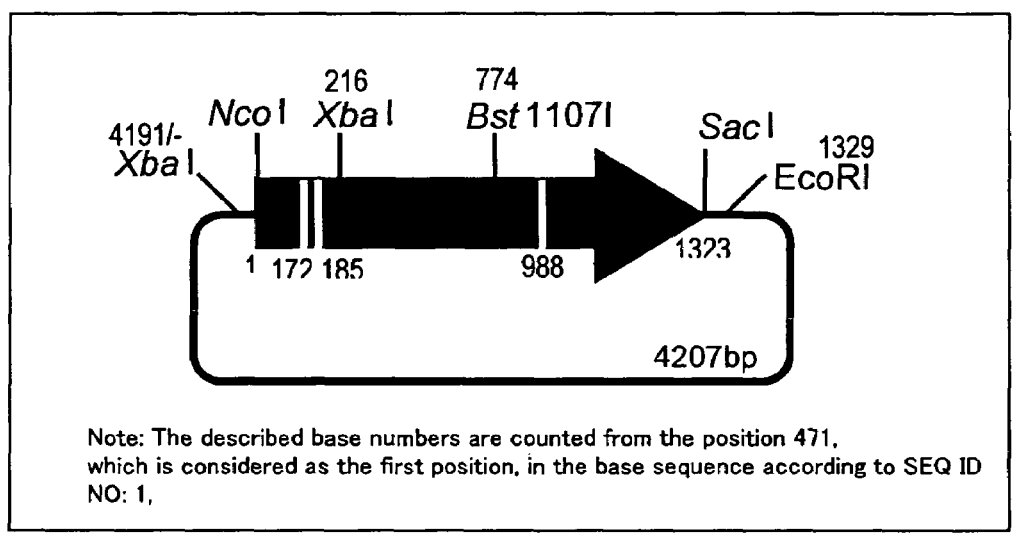
FIG. 14 shows a restriction map of a plasmid pPOS-FOD923.

1) Mutant enzymes 923-F330L and 923-Fro2 were obtained from *Escherichia coli* transformed by using a plasmid obtained by: treating a gene of a wild type or mutation-type enzyme 923-F2 with the restriction enzymes indicated by Table 15, based on the restriction enzyme map of the plasmid pPOSFOD923 shown in FIG. 14; cleaving a fragment containing the mutational position of interest; and inserting the fragment into the other plasmid treated with the same restriction enzymes.

2) A mutant enzyme 923-I58V was obtained from *Escherichia coli* transformed by using a plasmid obtained by: performing PCR with mutant primers P53 and P54 (indicated by SEQ ID NOS: 20 and 21) to amplify a region containing the mutation of interest; treating the obtained fragment with the restriction enzymes shown in Table 15; and inserting the fragment into pPOSFOD923 cleaved by the same restriction enzymes. Table 15 shows the result of evaluation of those mutant enzymes, by the determination method described in <Screening of Mutant Ketoamine Oxidase having Decreased Action on FZK>. It revealed that a substitution of isoleucine of amino acid no. 58 (I58) by valine or a substitution of arginine of amino acid no. 62 (R62) by histidine is effective to decrease the activity on FZK.

P53

CGACTCTAGAGGAATAACACCATGGCGCCCTC (SEQ ID NO: 20, including a XbaI site locating at downstream of the multicloning site of pPOS2)

P54

GCTTCTAGACTCAATTGGAGATCGACCT-TGTTCCGCAAGCGGATACCCATGACCT TAT (SEQ ID NO: 21, a complementary sequence to the sequence from 637 to 694 of SEQ ID NO: 1 containing a mutation such that the amino acid 581 is substituted by V, in FOD923)

<Test for Point Mutation of Effective Mutant Amino Acid Residue>

The isoleucine of the highly effective amino acid no. 58 (I58) was substituted by another amino acid to search for an effective point mutation-type ketoamine oxidase. P53 (SEQ ID NO: 20) and primers (P55-64) having the sequence indicated in (Table 15-2) were used to create a mutant strain by the method shown in 2) of <Identification of Effective Mutational Position>. Results obtained by determining an activity of the mutant enzyme of the activity on FZK to the activity on FVK by the method described in <Screening of Mutant Ketoamine Oxidase having Decreased Action on FZK> was shown in (Table 15-2).

The results revealed that substitutions of isoleucine of the amino acid no. 58 (I58) by threonine, asparagine, cysteine, serine, and alanine were also effective for decreasing the activity on FZK, other than by valine.

TABLE 15-2

| Strain | codon of amino acid at 58th position | Amino Acid Mutation | Primer No. | used primer (complementary chain) Sequence | SEQ ID NO | FZK/FVH |
|---|---|---|---|---|---|---|
| FOD923 | atc | — | — | — | — | 0.95 |
| 923-F2 | gtc | I58V, R62H, F330L | — | — | | 0.025 |
| 923-I58V | gtc | I58V | P54 | GCTTCTAGACTCAATTGGAGATCGACCTTGTTCCGCAAGCGGATACCCATGACCTTAT | 21 | 0.12 |
| 923-I58F | ttt | I58F | P55 | GCTTCTAGACTCAATTGGAGATCGACCTTGTTCCGCAAGCGGATACCCATAAACTTAT | 22 | 6.4 |
| 923-I58L | ctg | I58L | P56 | GCTTCTAGACTCAATTGGAGATCGACCTTGTTCCGCAAGCGGATACCCATCAGCTTAT | 23 | 1.6 |
| 923-I58M | atg | I58M | P57 | GCTTCTAGACTCAATTGGAGATCGACCTTGTTCCGCAAGCGGATACCCATCATCTTAT | 24 | 2.3 |
| 923-I58T | acc | I58T | P58 | GCTTCTAGACTCAATTGGAGATCGACCTTGTTCCGCAAGCGGATACCCATGGTCTTAT | 25 | 0.12 |
| 923-I58A | gcg | I58A | P59 | GCTTCTAGACTCAATTGGAGATCGACCTTGTTCCGCAAGCGGATACCCATCGCCTTAT | 26 | 0.30 |
| 923-I58Y | tat | I58Y | P60 | GCTTCTAGACTCAATTGGAGATCGACCTTGTTCCGCAAGCGGATACCCATATACTTAT | 27 | 54 |
| 923-I58N | aac | I58N | P61 | GCTTCTAGACTCAATTGGAGATCGACCTTGTTCCGCAAGCGGATACCCATGTTCTTAT | 28 | 0.16 |
| 923-I58C | tgc | I58C | P62 | GCTTCTAGACTCAATTGGAGATCGACCTTGTTCCGCAAGCGGATACCCATGCACTTAT | 29 | 0.16 |
| 923-I58S | agc | I58S | P63 | GCTTCTAGACTCAATTGGAGATCGACCTTGTTCCGCAAGCGGATACCCATGCTCTTAT | 30 | 0.19 |
| 923-I58G | ggc | I58G | P64 | GCTTCTAGACTCAATTGGAGATCGACCTTGTTCCGCAAGCGGATACCCATGCCCTTAT | 31 | 0.73 |

<Production of Mutant Ketoamine Oxidase>

Mutant ketoamine oxidase was purified by the same method as described in the reference example and produced.

Specificity of the mutant fructosyl aminoxidase of the present invention to various substrates are as shown in Table 16. Note that, concentration of each substrate was set to be 1 mM and other reaction conditions were set according to the activity determination method described in <Screening of Mutant Ketoamine Oxidase having Decreased Action on FZK>. The results indicated that 923-F2 (hereinafter, also called as FOD923M) has the highest reactivity to FV and has also high reactivity to FVH, while it has reactivities of 2.5% and 0.5% to FZK and FVL respectively and has little reactivities compared to that of FVH, indicating that the enzyme of the invention is an enzyme that does not substantially act on FZK and FVL.

TABLE 16

| Substrate | FOD 923 | 923-F1 | 923-F2 |
|---|---|---|---|
| FVH | 100 | 100 | 100 |
| FZK | 95 | 24 | 2.5 |
| FV | 630 | 680 | 220 |
| FVL | 2.6 | — | 0.5 |

<Mutant of Ketoamine Oxidase Derived from *Neocosmospora vasinfecta* 474>

Ketoamine oxidase derived from *Neocosmospora vasinfecta* 474 (FOD474) has high homology to ketoamine oxidases containing FOD923 and its amino acid sequence at an N-terminal region containing 158 of FOD923 is highly conserved as shown in FIG. 1. Using pPOSFOD474, FOD474 mutant strain 474-F1 in which 158 of FOD474 is substituted by a different amino acid (threonine) was acquired. Table 17 shows specificity of FOD474 and 474-F1 to various substrates. For the substrate specificity to FVH also was improved in FOD474, it indicated that the amino acid region no. 58 is a site that strongly affect on the specificity to FVH even in a case of a ketoamine oxidase derived from other microorganism species.

TABLE 17

| Substrate | FOD 474 | 474-F1 |
|---|---|---|
| FVH | 100 | 100 |
| FZK | 40 | 20 |
| FV | 540 | 380 |

Example 8 pH Dependency of Activity of Ketoamine Oxidase FOD923, FOD474, and FOD923M on FVH and FZK 20 µl of an enzyme solution was added to 200 µl of a reaction solution (50 mM buffer, 0.1% Triton X-100, 0.03% 4-aminoantipyrine, 0.02% TOOS, 5 U/ml peroxidase, 2 mM substrate). The whole was incubated at 37° C. for 5 minutes and then 500 µl of 0.5% SDS was added thereto followed by determining absorbance at 555 nm. Tris-HCl (pH 7.5, 8.0, 8.5), PIPES (pH 6.0, 6.5, 7.0), and Bistris-HCl (pH 5.0, 5.5, 6.0, 6.5) were used as the buffers for determination. Also, absorbance was determined using a reaction solution containing no substrates. Differences in the absorbance when FVH and FZK each were used as a substrate and concentrations of the enzyme in the enzyme solution to be used are described in Table 18. Table 19 shows a specific activity (%) represented by (FZK/FVH) when FVH and FZK each were used as a substrate. The results confirmed that the specificity to FVH significantly increases when pH is around 6.

Example 9

Substrate Specificity of Ketoamine Oxidase FOD923M

Determination was performed by the same method described in <Reference Example: Substrate Specificity of Ketoamine Oxidase derived from *Curvularia clavata* YH923 (FERM BP-10009), Ketoamine Oxidase derived from *Neocosmospora vasinfecta* 474, and Ketoamine Oxidase derived from *Fusarium oxysporum* (manufactured by Asahi Kasei Pharma)>. Table 3 shows the results.

C. for 200 seconds in a cell having an optical path length of 1 cm followed by adding 10 μl of R3 thereto and incubating at 37° C. for 100 seconds. Subsequently, 10 L of R4 was added thereto and the whole was incubated at 37° C. for 100 seconds. During the process, absorbency at 730 nm 180 seconds after R2 was added (A1), absorbency at 730 nm 90 seconds after R3 was added (A2), and absorbency at 730 nm 90 seconds after R4 was added (A3) are determined. In addition, the same operation as described above using the same sample except R1 (−protease) was used instead of R1 (+protease) was carried out, and absorbency at 730 nm 180 seconds after R2 was added (A1b), absorbency at 730 nm 90 seconds after R3 was added (A2b), and absorbency at 730 nm 90 seconds after R4 was added (A3b) are also determined. Amount of a gly-

TABLE 18

|  | Enzyme conc. |  | Bistris | | | | PIPES | | | Tris | | |
| --- | --- | --- | --- | --- | --- | --- | --- | --- | --- | --- | --- | --- |
|  | (U/ml) | substrate | 5.0 | 5.5 | 6.0 | 6.5 | 6.0 | 6.5 | 7.0 | 7.5 | 8.0 | 8.5 |
| FOD923 | 0.1 | FVH | −0.002 | 0.020 | 0.048 | 0.063 | 0.057 | 0.073 | 0.070 | 0.066 | 0.042 | 0.025 |
|  | 0.1 | FZK | −0.001 | 0.005 | 0.011 | 0.015 | 0.013 | 0.022 | 0.033 | 0.030 | 0.041 | 0.049 |
| FOD474 | 0.167 | FVH | 0.023 | 0.084 | 0.187 | 0.273 | 0.265 | 0.303 | 0.243 | 0.163 | 0.104 | 0.063 |
|  | 0.833 | FZK | 0.012 | 0.022 | 0.042 | 0.063 | 0.066 | 0.093 | 0.132 | 0.162 | 0.200 | 0.210 |
| FOD923M | 0.04 | FVH | 0.005 | 0.057 | 0.168 | 0.189 | 0.192 | 0.181 | 0.075 | 0.062 | 0.017 | 0.009 |
|  | 0.64 | FZK | −0.001 | 0.012 | 0.030 | 0.045 | 0.033 | 0.038 | 0.045 | 0.036 | 0.049 | 0.060 |

TABLE 19

|  | Bistris | | | | PIPES | | | Tris | | |
| --- | --- | --- | --- | --- | --- | --- | --- | --- | --- | --- |
|  | 5.0 | 5.5 | 6.0 | 6.5 | 6.0 | 6.5 | 7.0 | 7.5 | 8.0 | 8.5 |
| FOD923 | — | 25.0 | 22.9 | 23.8 | 17.8 | 30.1 | 47.1 | 45.5 | 97.6 | 196.0 |
| FOD474 | 10.4 | 5.2 | 4.9 | 4.6 | 5.0 | 6.1 | 10.9 | 19.9 | 38.5 | 66.7 |
| FOD923M | — | 1.3 | 1.1 | 1.5 | 1.1 | 1.3 | 3.8 | 3.6 | 18.0 | 41.7 |

Example 10

Determination of Hemoglobin A1c

Figure 15:
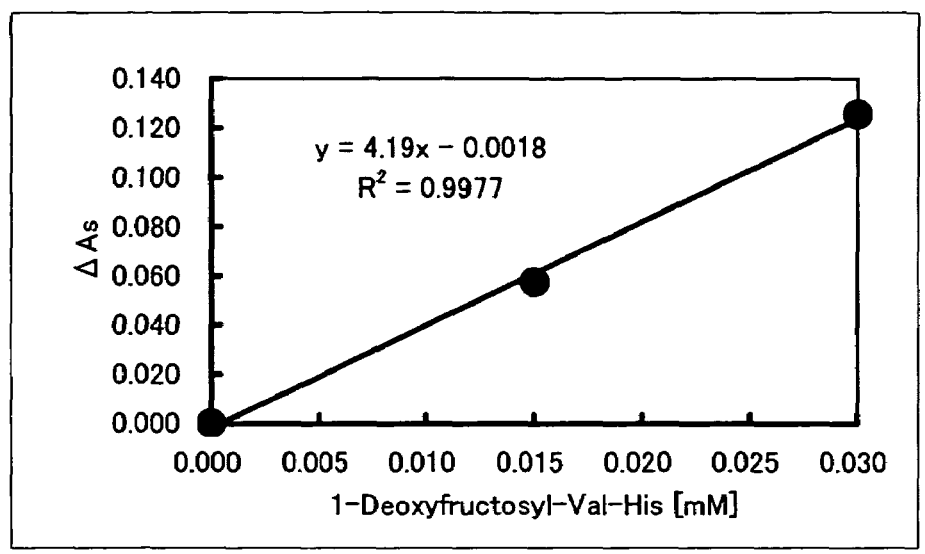
FIG. 15 shows the relationship between an absorbance difference ΔAs and an FVH concentration.

To create a calibration curve, 324 μl of R1 (−protease) and 90 μl of R2 are added to 36 μl of a hemoglobin A1c standard solution having FVH added thereto, in a cell having an optical path length of 1 cm. After the whole is incubated at 37° C. for 200 seconds, 10 μl of R3 is added and the whole is incubated at 37° C. for 100 seconds. Subsequently, 10 μl of R4 is added thereto and the whole is incubated at 37° C. for 100 seconds. During the process, absorbency at 730 nm 180 seconds after R2 was added (A1s), absorbency at 730 nm 90 seconds after R3 was added (A2s), and absorbency at 730 nm 90 seconds after R4 was added (A3s) are determined. Similarly, the same operation is performed with a hemoglobin A1c standard solution having no FVH added thereto, and absorbency at 730 nm 180 seconds after R2 was added (A1sb), absorbency at 730 nm 90 seconds after R3 was added (A2sb), and absorbency at 730 nm 90 seconds after R4 was added (A3sb) are also determined. The calibration curve shown in FIG. 15 was created from the relationship between the difference of the absorbance ΔAs=(A3s−A2s)−(A3sb−A2sb) and the FVH concentrations.

Next, 324 μl of R1 (+protease) was added to 36 μl of each low or high level hemoglobin A1c standard solution. The whole was incubated at 37° C. for 60 minutes followed by adding 90 μL of R2 thereto. The whole was incubated at 37° cated β-chain N-terminal of hemoglobin in each low or high level hemoglobin A1c standard solution can be obtained from the relationship between the difference of the absorbance ΔA=(A3−A2)−(A3b−A2b) and the FVH concentrations. As shown in Table 20, the theoretical values agree well with the determined values. Note that, the difference of the absorbance ΔAε=(A2−A1)−(A2b−A1b) is considered to be proportional to the amount of glycated ε-amino groups of lysine residues in the glycated hemoglobin.

<R1 (+Protease)>

20 mM Tris-HCl (pH 7.5)

0.1% Triton X-100

150 mM Sodium chloride 2 mM Calcium chloride 2.1 kU/ml neutral proteinase derived from *Bacillus* sp. (manufactured by Toyobo Co., Ltd.)

<R1 (−Protease)>

20 mM TrisvHCl (pH 7.5)

0.1% Triton X-100

150 mM Sodium chloride 2 mM Calcium chloride

<R2>

20 mM Tris-HCl (pH 7.5)

6.35 mM WST3 (manufactured by Dojindo Laboratories)

0.08 mM DA-64 (manufactured by Wako Pure Chemical Industries, Ltd.)

25 U/ml Peroxidase (manufactured by Sigma-Aldrich Corp.)

(WST-3: 2-(4-iodophenyl)-3-(2,4-dinitrophenyl)-5-(2,4-disulfophenyl)-2H-tetrazolium)

(DA-64: N-(carboxymethyl aminocarbonyl)-4,4'-bis(dimethylamino)-diphenylamine)

<R3>

500 U/ml FOD2

<R4>

500 U/ml FOD923

<Low Level Hemoglobin A1c Standard Solution>

To prepare, an available freeze-dried product of calibrator for hemoglobin determination (Determiner Control for HbA1c: manufactured by Kyowa Medex Co., Ltd.) having a low value (represented hemoglobin A1c value (JDS value): 5.6%) was dissolved in distilled water to be 4 mg/ml.

By a conversion using the equation (JDS value)=0.9259 (IFCC value)+1.6697, described in "Rinsho Kensa, 46 (6) 729-734, 2002", the hemoglobin A1c value (IFCC value) is converted to be 4.2%. Consequently, when hemoglobin is a tetramer consisting of two α-chains and two β-chains and has a molecular weight of 64,550, a theoretical value for the concentration of the glycated β-chain N-terminals in this standard solution will be 0.0052 mM.

<High level Hemoglobin A1c Standard Solution>

To prepare, an available freeze-dried product of calibrator for hemoglobin determination (Determiner Control for HbA1c: manufactured by Kyowa Medex Co., Ltd.) having a high value (represented hemoglobin A1c value (JDS value): 10.2%) was dissolved in distilled water to be 4 mg/ml.

By a conversion using the equation (JDS value)=0.9259 (IFCC value)+1.6697, described in "Rinsho Kensa, 46 (6) 729-734, 2002", the hemoglobin A1c value (IFCC value) is converted to be 9.2%. Consequently, when hemoglobin is a tetramer consisting of two α-chains and two β-chains and has a molecular weight of 64,550, a theoretical value for the concentration of the glycated β-chain N-terminals in this standard solution will be 0.0114 mM.

<Hemoglobin A1c Standard Solution Having FVH Added Thereto>

To prepare, FVH (manufactured by Peptide Institute Inc.) was added to the above low level hemoglobin A1c standard solution to be 0.030 mM and 0.015 mM.

<Hemoglobin A1c Standard Solution Having No FVH Added Thereto>

The above low level hemoglobin A1c standard solution was used.

Example 11

Figure 16:
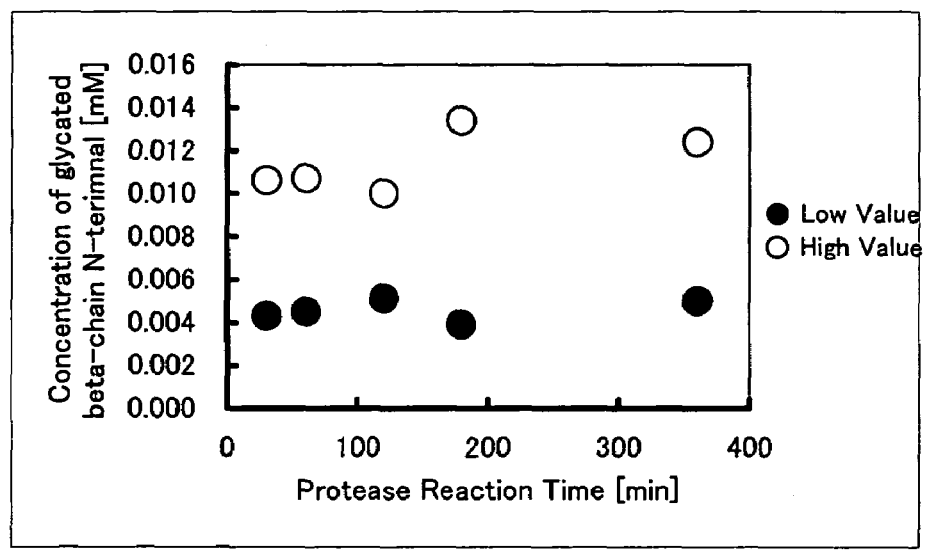
FIG. 16 shows the relationship between a protease reaction time and a resultant determined value.

Relationship between Reaction Time for Protease and Determined Value of Hemoglobin A1c Reaction times for protease in the low and high hemoglobin A1c standard solutions used in Example 10 varied from 30 minutes to 360 minutes. FIG. 16 shows the obtained determined values of hemoglobin A1c. It indicates that the agreement of the theoretical value and the determined value in Example 10 is not accidentally obtained by limiting the reaction time for protease to be 60 minutes. It also indicates that the determined values are almost stable with time when the reaction time for protease varies from 30 minutes to 360 minutes and therefore an actual amount of glycated β-chain N-terminals in glycated hemoglobin is determined by the present determination method.

Example 12

1) Evaluation of Effect of pH in Degradation Reaction of Glycated Hemoglobin by Neutral Proteinase Derived from *Bacillus* sp. (Manufactured by Toyobo Co., Ltd.)

Figure 17:
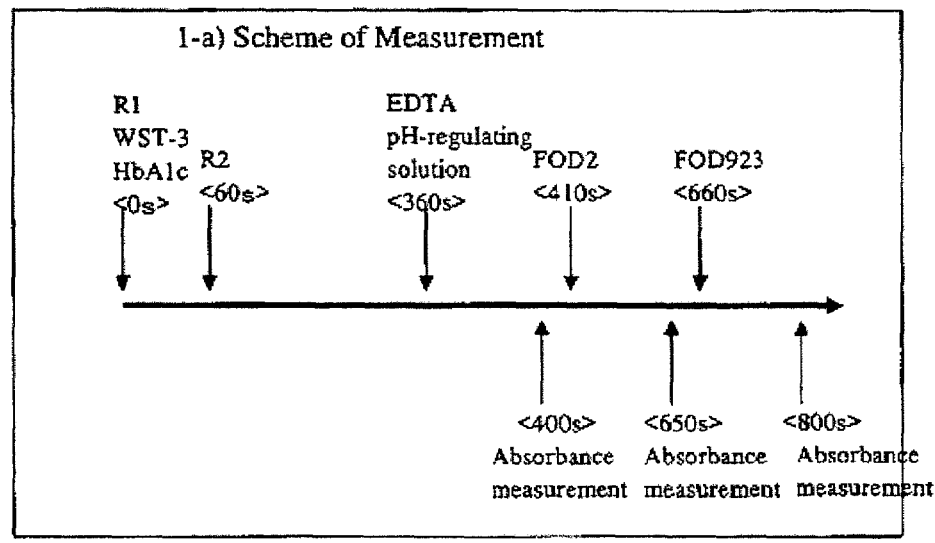
FIG. 17 shows a determination scheme in the case where an FVH amount is determined using FOD923 after elimination of signals derived from a glycated lysine and a peptide including a glycated lysine with FOD2 after degradation of glycated hemoglobin by a protease.

1-a) Case where the Amount of FVH is Determined Using FOD923 after Glycated Lysine and Peptides Containing the Glycated Lysine were Digested by FOD2, After a Protease Reaction 30.4 µl of 20 mM WST3 and 36 µl of a glycated hemoglobin sample were added to 324 µl of a R1 reaction solution (20 mM buffer, surfactant, sodium chloride, 2 mM calcium chloride, 1.2 kU/ml neutral proteinase (manufactured by Toyobo Co., Ltd.)). After 60 seconds, 44.6 µl of a R2 reaction solution (100 mM buffer, 50 U/ml peroxidase, 0.16 mMDA-64) was added thereto, and 5 µl of 0.5 M EDTA and 15 µl of a pH-regulating solution were added thereto after further 300 seconds. After further 50 seconds, 10 µl of 1,500 U/ml of FOD2 was added thereto, 5 µl of 500 U/ml of FOD923 was added thereto after further 250 seconds, and the whole was subjected to a reaction for 150 seconds. All reactions were carried out at 37° C. in a cell of an absorptiometer. The absorbance at 730 nm was monitored to obtain a difference (A1) between the absorbance at 240 seconds after FOD2 was added and the absorbance at 140 seconds after FOD923 was added. FIG. 17 shows a scheme of the determination.

A similar operation was carried out in a case where FVH was preliminarily added to the R1 reaction solution to be 3.33 µM, to obtain a difference of absorbances (A2). Also, the same operation except that 5 µl of 0.5 M EDTA and 15 µl of a pH-regulating solution was added before glycated hemoglobin was added, not after a R2 reaction solution was added, was carried out thereby obtaining a difference of absorbances in a blank reaction (Ab).

The FVH that was cleaved from glycated hemoglobin by protease can be calculated from an equation "determined value (µM)=(A1−Ab)/(A2−A1)×30" with those differences of absorbances. Note that, EDTA was added to terminate or inhibit the reaction of the protease. The pH-regulating solution was added to adjust pH at a reaction of ketoamine oxidase FOD2 and FOD923 to be about 7.5. Combinations of the buffer, surfactant, concentration of sodium chloride, and a pH-regulating solution to be used in the R1 and R2 reaction solutions and determinations thereof were shown in Table 21.

Figure 18:
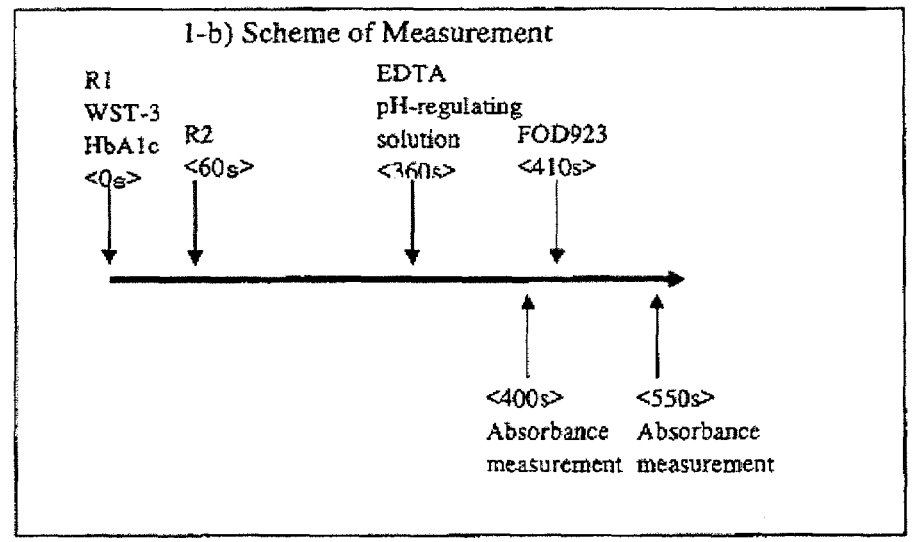
FIG. 18 shows a determination scheme in the case where an FVH amount is determined using FOD923 without elimination of signals derived from a glycated lysine and a peptide including a glycated lysine after degradation of glycated hemoglobin by a protease.

1-b) Case where the Amount of FVH is Determined Using FOD923 Such that Glycated Lysine and Peptide Containing the Glycated Lysine are Not Digested by FOD2, after a Protease Reaction 30.4 µl of 20 mM WST3 was added to 324 µl of a R1 reaction solution (20 mM buffer, surfactant, sodium chloride, 2 mM calcium chloride, 1.2 kU/ml neutral proteinase (manufactured by Toyobo Co., Ltd.)) and 36 µl of a glycated hemoglobin sample was added thereto. After 60 seconds, 44.6 µl of a R2 reaction solution (100 mM buffer, 50 U/ml peroxidase, 0.16 mM DA-64) was added thereto, and 5 µl of 0.5 M EDTA and 15 µl of a pH-regulating solution were added thereto after further 300 seconds. After further 50 seconds, 5 µl of 500 U/ml of FOD923 was added thereto, and the whole was subjected to a reaction for 150 seconds. All reactions were carried out at 37° C. in a cell of an absorptiometer. The absorbance at 730 nm was monitored to obtain a difference (A1) between the absorbance at 40 seconds after the 0.5 M EDTA and a pH-regulating solution were added and the absorbance at 140 seconds after FOD923 was added. FIG. 18 shows a scheme of the determination.

A similar operation was carried out in a case where FVH was preliminarily added to the R1 reaction solution to be 3.33 µM, to obtain a difference of absorbances (A2). Also, the same operation except that 5 µl of 0.5 M EDTA and 15 µl of a pH-regulating solution was added before glycated hemoglobin was added, not after R2 reaction solution was added, was carried out thereby obtaining a difference of absorbances in a blank reaction (Ab). The FVH that was cleaved from glycated hemoglobin by protease can be calculated from an equation "determined value (µM)=(A1−Ab)/(A2−A1)×30" with those differences of absorbances. Note that, EDTA was added to terminate or inhibit the reaction of the protease. The pH-regulating solution was added to adjust pH at a reaction of ketoamine oxidase FOD2 and FOD923 to be about 7.5. Combinations of the buffer, surfactant, concentration of sodium chloride, and a pH-regulating solution to be used in the R1 and R2 reaction solutions and determinations thereof were shown in Table 21.

TABLE 20

|  | ΔA | measured value [mM] | theoretical value [mM] |
|---|---|---|---|
| Low level hemoglobin A1c standard solution | 0.0172 | 0.0045 | 0.0052 |
| High level hemoglobin A1c standard solution | 0.0430 | 0.0107 | 0.0114 |

(2) Evaluation of Effect of pH in Degradation Reaction of Glycated Hemoglobin by Protease Derived from *Bacillus* sp. ASP842

2-a) Case where the Amount of FVH is Determined Using FOD923 after Glycated Lysine and Peptides Containing the Glycated Lysine are Digested by FOD2, after a Protease Reaction For the R1 reaction solution in 1-a) of Example 12, a protease derived from *Bacillus* sp. ASP842 was added thereto to be 0.85 U/ml instead of 1.2 kU/ml neutral proteinase (manufactured by Toyobo Co., Ltd.). An operation similar to 1-a) was carried out using combinations of the buffer, surfactant, concentration of sodium chloride, and a pH-regulating solution to be used in the R1 and R2 reaction solutions as shown in Table 22. Table 22 also shows the determination.

2-b) Case where the Amount of FVH is Determined Using FOD923, Such that Glycated Lysine and Peptides Containing the Glycated Lysine are Not Digested by FOD2, after a Protease Reaction For the R1 reaction solution in 1-b) of Example 12, a protease derived from *Bacillus* sp. ASP842 was added thereto to be 0.85 U/ml instead of 1.2 kU/ml neutral proteinase (manufactured by Toyobo Co., Ltd.). An operation similar to 1-b) was carried out using combinations of the buffer, surfactant, concentration of sodium chloride, and a pH-regulating solution to be used in the R1 and R2 reaction solutions as shown in Table 22. Table 22 also shows the determination.

(3) Evaluation of Effect of pH in Degradation Reaction of Glycated Hemoglobin by Protease Derived from *Lysobacter enzymogenes* YK-366

Figure 19:
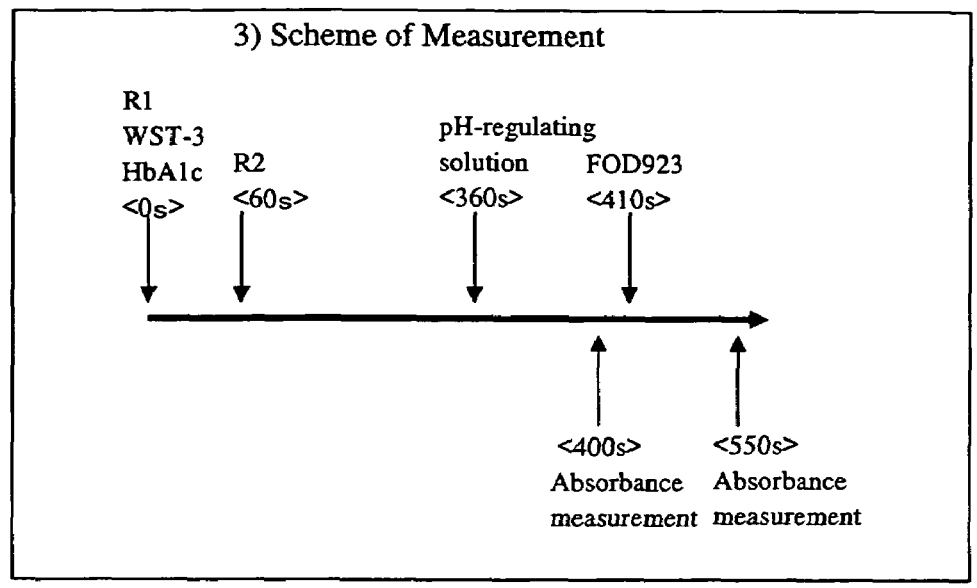
FIG. 19 shows a determination scheme in the case where an FVH amount is determined using FOD923M without elimination of signals derived from a glycated lysine and a peptide including a glycated lysine after degradation of glycated hemoglobin by a protease.

30.4 µl of 20 mM WST3, 36 µl of glycated hemoglobin sample, and 5 µl of distilled water were added to a R1 reaction solution (20 mM buffer, surfactant, sodium chloride, 2 mM calcium chloride, 0.43 U/ml protease derived from *Lysobacter enzymogenes* YK-366). After 60 seconds, 44.6 µl of a R2 reaction solution (100 mM buffer, 50 U/ml peroxidase, 0.16 mM DA-64) was added thereto, followed by adding 15 µl of a pH-regulating solution after further 300 seconds. After 50 seconds, 5 µl of 500 U/ml of FOD 923 was added thereto and a reaction was brought about for 150 seconds. All reactions were carried out at 37° C. in a cell of an absorptiometer. The absorbance at 730 nm was preliminarily monitored to obtain a difference (A1) between the absorbance at 40 seconds after the pH-regulating solution was added and the absorbance at 140 seconds after FOD923 was added. FIG. 19 shows a scheme of the determination.

TABLE 21

| pH | 5.0 | 5.5 | 6.0 | 6.5 | 7.0 | 7.5 |
|---|---|---|---|---|---|---|
| Buffer | MES | Bistris | Bistris | Bistris | Tris | Tris |
| Surfactant | 0.4% | 0.3% | 0.2% | 0.1% | 0.1% | 0.2% |
|  | Triton X-100 | Triton X-100 | Triton X-100 | Briji 35 | Triton X-100 | Triton X-100 |
| NaCl Conc. | 150 mM | 150 mM | 150 mM | 225 mM | 150 mM | 150 mM |
| pH-regulating solution | 1M Tris (pH 9.0) | 1M Tris (pH 9.0) | 1M Tris (pH 8.5) | 1M Tris (pH 8.5) | Distilled water | Distilled water |
| 1-a) measured value [µM] | 30.7 | 30.3 | 29.0 | 30.5 | 29.2 | 30.0 |
| 1-b) measured value [µM] | 29.7 | 30.7 | 28.8 | 32.7 | 36.1 | 34.6 |

TABLE 22

| pH | 5.0 | 5.5 | 6.0 | 7.0 | 7.5 |
|---|---|---|---|---|---|
| Buffer | Bistris | Bistris | Bistris | Tris | Tris |
| Surfactant | 0.4% | 0.3% | 0.2% | 0.2% | 0.2% |
|  | Triton X-100 | Triton X-100 | Triton X-100 | Triton X-100 | Triton X-100 |
| NaCl Conc. | 150 mM | 150 mM | 150 mM | 150 mM | 150 mM |
| pH-regulating solution | 1M Tris (pH 9.0) | 1M Tris (pH 9.0) | 1M Tris (pH 8.5) | Distilled water | Distilled water |
| 2-a) measured value [µM] | 29.5 | 28.2 | 29.2 | 29.3 | 31.4 |
| 2-b) measured value [µM] | 29.2 | 31.6 | 27.7 | 35.3 | 34.2 |

TABLE 23

| pH | 5.5 | 6.0 | 6.5 | 7.0 | 7.5 |
|---|---|---|---|---|---|
| Buffer | Bistris | Bistris | Bistris | Tris | Tris |
| Surfactant | 0.3% Triton X-100 | 0.2% Triton X-100 | 0.2% Triton X-100 | 0.1% Triton X-100 | 0.2% Triton X-100 |
| NaCl Conc. | 150 mM | 150 mM | 150 mM | 150 mM | 150 mM |
| pH-regulating solution | 1M Tris (pH 9.0) | 1M Tris (pH 8.5) | 1M Tris (pH 8.5) | Distilled water | Distilled water |
| measured value [μM] | 27.5 | 26.7 | 26.8 | 36.6 | 35.3 |

A similar operation was carried out in a case where FVH was preliminarily added to the R1 reaction solution to be 3.33 μM, to obtain a difference of absorbances (A2). Also, a similar operation using a protease inactivated by preliminarily treating it at 95° C. for 10 minutes was carried out thereby obtaining a difference of absorbances in a blank reaction (Ab).

The FVH that was cleaved from glycated hemoglobin by a protease can be calculated from an equation "determined value (μM)=(A1−Ab)/(A2−A1)×30" with those differences of absorbances.

An operation similar to one in 1-b) of Example 12 was carried out using combinations of the buffer, surfactant, concentration of sodium chloride, and a pH-regulating solution to be used in the R1 and R2 reaction solutions as shown in Table 23. Determinations thereof were shown in Table 23.

A glycated hemoglobin sample such that 5.9 mg/ml thereof is 16.7% in terms of IFCC value (a theoretical value for concentration of glycated β-chain N-terminal is to be 30.5 μM) was used. The results shown in Table 21 to Table 23 indicate that: the protease does not cleave a peptide containing glycated lysine which can be acted with FOD923 out from glycated hemoglobin, when pH in a protease reaction to be 5.0-6.0. Therefore, the results indicated that the amount of FVH was specifically and precisely determined (the amount of glycated β-chain N-terminals of the glycated hemoglobin) without digested by FOD2, i.e. the amount of hemoglobin A1c was precisely determined.

Example 13

Determination of FVH in Degradation Product of Glycated Hemoglobin by Protease with Mutant Ketoamine Oxidase FOD923 Having High Specificity 1-a) Case where the Amount of FVH is Determined Using FOD 923M after Glycated Lysine and Peptides Containing the Glycated Lysine are Digested by FOD2, after a Protease Reaction An operation similar to one in 1-a) of Example 12 was carried out, except Tris-HCl (pH 7.5) as the buffer of a R1 reaction solution, 0.1% Triton X-100 as the surfactant, and concentration of sodium chloride of 150 mM were used, and 5 μl of 32 U/ml of FOD923M instead of 5 μl of 500 U/ml of FOD923 was added. From determination, the determined value for FVH was 28.6 μM.

1-b) Case where the Amount of FVH is Determined Using FOD923M Such that Glycated Lysine and Peptides Containing the Glycated Lysine are Not Digested by FOD2, after a Protease Reaction An operation similar to one in 1-b) of Example 12 was carried out, except Tris-HCl (pH 7.5) as the buffer of a R1 reaction solution, 0.1% Triton X-100 as the surfactant, and concentration of sodium chloride of 150 mM were used, and 5 μl of 32 U/ml of FOD923M instead of 5 μL of 500 U/ml of FOD923 was added. From determination, the determined value for FVH was 30.0 μM.

From the above, the use of ketoamine oxidase having high specificity allows determination for the amount of FVH (the amount of glycated β-chain N-terminals of glycated hemoglobin) specifically without being digested by FOD2 under pH 7.5 (i.e. a condition in which the protease cleaves glycated lysine and peptides containing the glycated lysine from glycated hemoglobin), i.e. it allows precise determination for the amount of hemoglobin A1c.

INDUSTRIAL APPLICABILITY

A method of specifically determining glycated β-chain N-terminals of glycated hemoglobin using enzymes without operating to separate and a kit involving determination reagents can be provided.

[Reference to Deposited Biological Materials]

(1)

i. Name and address of depository institution at which the biological material of interest is deposited.

International Patent Organism Depositary, National Institute of Advanced Industrial Science and Technology Tsukuba Central 6, 1-1-1 Higashi, Tsukuba, Ibaraki, Japan (post code: 305-8566)

ii. Date when the biological material was deposited to the depository institution of i.

Feb. 12, 2003 (original deposit date)

Apr. 12, 2004 (date of transfer to the deposition under Budapest Treaty from the original deposition)

iii. Accession number for the deposition assigned by the depository institution of i.

FERM BP-10009

(2)

i. Name and address of depository institution to which the biological material of interest is deposited International Patent Organism Depositary, National Institute of Advanced Industrial Science and Technology Tsukuba Central 6, 1-1-1 Higashi, Tsukuba, Ibaraki, Japan (post code: 305-8566)

ii. Date when the biological material was deposited to the depository institution of i.

Feb. 24, 2004 (original deposit date)

iii. Accession number for the deposition assigned by the depository institution of i.

FERM BP-08641

(3)

i. Name and address of depository institution to which the biological material of interest is deposited
International Patent Organism Depositary, National Institute of Advanced Industrial Science and Technology
Tsukuba Central 6, 1-1-1 Higashi, Tsukuba, Ibaraki, Japan (post code: 305-8566)

ii. Date when the biological material was deposited to the depository institution of i.
Jan. 30, 2004 (original deposit date)
Apr. 12, 2004 (date of transfer to the deposition under Budapest Treaty from the original deposition)

iii. Accession number for the deposition assigned by the depository institution of i.
FERM BP-10010

(4)

i. Name and address of depository institution to which the biological material of interest is deposited
International Patent Organism Depositary, National Institute of Advanced Industrial Science and Technology
Tsukuba Central 6, 1-1-1 Higashi, Tsukuba, Ibaraki, Japan (post code: 305-8566)

ii. Date when the biological material was deposited to the depository institution of i.
Feb. 24, 2004 (original deposit date)

iii. Accession number for the deposition assigned by the depository institution of i.
FERM BP-08642

The invention claimed is:

1. A method of specifically determining a glycated β-chain N-terminal of glycated hemoglobin, the method comprising:
reacting the glycated hemoglobin with enzymes comprising (i) a protease comprising carboxypeptidase B, neutral protease, carboxypeptidase A, thermolysin, *Bacillus* sp. ASP842 protease, *Lysobacter enzymogenes* YK-366 protease, or *Aeromonas hydrophila* NBRC 3820 protease, and (ii) a ketoamine oxidase having at least 75% sequence homology with SEQ ID NO: 1, without an operation for increasing the purity or concentration of glycated hemoglobin or a substance derived from glycated hemoglobin;
wherein the ketoamine oxidase (ii) has a reactivity to ε-1-deoxyfructosyl-(α-benzyloxycarbonyl-L-lysine) of 30% or less compared with that to 1-deoxyfructosyl-L-valyl-L-histidine.

2. The determination method according to claim 1, wherein the method is performed under a reaction condition of pH 5.0 to 6.0.

3. The determination method according to claim 1, wherein the method is performed under a reaction condition of pH 5.5 to 6.5.

* * * * *

SEQUENCE LISTING

```
<160> NUMBER OF SEQ ID NOS: 50

<210> SEQ ID NO 1
<211> LENGTH: 2212
<212> TYPE: DNA
<213> ORGANISM: Curvlaria claveta
<220> FEATURE:
<221> NAME/KEY: CDS
<222> LOCATION: (471)..(752)
<220> FEATURE:
<221> NAME/KEY: CDS
<222> LOCATION: (808)..(1230)
<220> FEATURE:
<221> NAME/KEY: CDS
<222> LOCATION: (1280)..(1695)
<220> FEATURE:
<221> NAME/KEY: CDS
<222> LOCATION: (1751)..(1952)

<400> SEQUENCE: 1
ggtatcagat cagatacaag atagacccca gattttctgt tatcagcacg ctccgatatc     60
gacaaggcga aggtgcgttg agtgctccag tttaggagat acggacagcc cgtcttcgat    120
tgacgttgtg ctgacgtccg atgagctaac ttcgttggga tattataaca gtcaggatca    180
ccaagcgaga cccaggcgcc atcccatggc cgagcgtcgc ccccagtcag cggtacatgg    240
agcggaaggc ttcaattact caatcaaaac ttgttggagc tcgcaattga gcggggagta    300
tgcctcgcta tcgtatcatt gagctggtgg cgtgtgcaga cttcattgat acttaaccgg    360
cgggcgttga gcctgaccca ttgtggattg cttctgatca cggcttgcgc cttcgtccag    420
caaaacttca gccatccggg aatccgacca cacatcctcg tcatttcgac atg gcg      476
                                                          Met Ala
                                                          1 ccc tca aga gca aac act tct gtt atc gtt gtc ggt ggc ggt ggc act    524
Pro Ser Arg Ala Asn Thr Ser Val Ile Val Val Gly Gly Gly Gly Thr
 5              10                  15 att ggc tct tca acc gct ctt cat cta gtc cgc tcg ggc tac aca cca    572
Ile Gly Ser Ser Thr Ala Leu His Leu Val Arg Ser Gly Tyr Thr Pro
20                  25                  30 tct aac atc acc gtt ctt gac aca tac cct atc cca tca gcg cag tca    620
Ser Asn Ile Thr Val Leu Asp Thr Tyr Pro Ile Pro Ser Ala Gln Ser
35                  40                  45                  50 gct gga aat gac ctg aat aag atc atg ggt atc cgc ttg cgg aac aag    668
Ala Gly Asn Asp Leu Asn Lys Ile Met Gly Ile Arg Leu Arg Asn Lys
        55                  60                  65
```

```
gtc gat ctc caa ttg agt cta gaa gcc agg cag atg tgg aga gag gat    716
Val Asp Leu Gln Leu Ser Leu Glu Ala Arg Gln Met Trp Arg Glu Asp
 70                  75                  80 gac cta ttc aaa gag tat ttc cac aac act gga aga gtatgtacag tcagca  768
Asp Leu Phe Lys Glu Tyr Phe His Asn Thr Gly Arg
 85                  90 gagtgactgt ttgaagattg gagctgacgg aagatgtag ctc gac tgt gca cat     822
                                          Leu Asp Cys Ala His
                                           95 ggg gaa gag gga ctt gca gat ttg aga cag gca tac cag gct ctg ctc    870
Gly Glu Glu Gly Leu Ala Asp Leu Arg Gln Ala Tyr Gln Ala Leu Leu
100                 105                 110                 115 gac gct aac gcg ggt ctc gaa gaa aca aca gaa tgg ctt gac tcc gaa    918
Asp Ala Asn Ala Gly Leu Glu Glu Thr Thr Glu Trp Leu Asp Ser Glu
120                 125                 130 gac gaa att cta aag aaa atg ccg ctt ctg gac cgc gag caa atc aag    966
Asp Glu Ile Leu Lys Lys Met Pro Leu Leu Asp Arg Glu Gln Ile Lys
135                 140                 145 ggc tgg aaa gcg gtt tac agc caa gac ggc ggc tgg ctg gct gca gca    1014
Gly Trp Lys Ala Val Tyr Ser Gln Asp Gly Gly Trp Leu Ala Ala Ala
150                 155                 160 aaa gcc atc aat gct ata ggc gag tac ttg cga gac caa gga gtt aag    1062
Lys Ala Ile Asn Ala Ile Gly Glu Tyr Leu Arg Asp Gln Gly Val Lys
165                 170                 175 ttt ggt ttt ggt ggt gct gga tcg ttc aag cag cct ctt ttg gcc gag    1110
Phe Gly Phe Gly Gly Ala Gly Ser Phe Lys Gln Pro Leu Leu Ala Glu
180                 185                 190                 195 gga gtg tgc att ggc gta gag aca gtc gac ggg acg agg tac tac gcc    1158
Gly Val Cys Ile Gly Val Glu Thr Val Asp Gly Thr Arg Tyr Tyr Ala
200                 205                 210 gat aaa gtt gtg ctt gca gct ggt gct tgg agt ccg gta ttg gtc gac    1206
Asp Lys Val Val Leu Ala Ala Gly Ala Trp Ser Pro Val Leu Val Asp
215                 220                 225 ctg gaa gat caa tgc gtt tca aaa gtaggtcttt gtgacggtgc tgcttcatat  1260
Leu Glu Asp Gln Cys Val Ser Lys
230                 235 gcaaatctaa ctttgttag gct tgg gta tat gct cac ata cag ctt acg cct  1312
                    Ala Trp Val Tyr Ala His Ile Gln Leu Thr Pro
                    240                 245 gag gaa gca gca gag tac aaa aac gtg cct gtg gta tac aac ggc gac    1360
Glu Glu Ala Ala Glu Tyr Lys Asn Val Pro Val Val Tyr Asn Gly Asp
250                 255                 260 gtc ggc ttc ttc ttc gag cct gac gag cac ggc gtt atc aag gtt tgt    1408
Val Gly Phe Phe Phe Glu Pro Asp Glu His Gly Val Ile Lys Val Cys
265                 270                 275 gac gaa ttt cca ggt ttt aca cgc ttc aag caa cat cag cca tat ggc    1456
Asp Glu Phe Pro Gly Phe Thr Arg Phe Lys Gln His Gln Pro Tyr Gly
280                 285                 290 gcc aaa gca ccg aaa cgt atc tcc gtg ccc aga tcg gca gcg aag cac    1504
Ala Lys Ala Pro Lys Arg Ile Ser Val Pro Arg Ser Ala Ala Lys His
295                 300                 305                 310 ccg acg gat act tac ccc gat gcg tcg gag aag agc atc cgc aag gcc    1552
Pro Thr Asp Thr Tyr Pro Asp Ala Ser Glu Lys Ser Ile Arg Lys Ala
315                 320                 325 att gca act ttc ctg ccc aag ttc aca gag aag gag cta ttc aac cgg    1600
Ile Ala Thr Phe Leu Pro Lys Phe Thr Glu Lys Glu Leu Phe Asn Arg
330                 335                 340 cat cta tgt tgg tgt acg gat acg gct gac gct gcg cta ttg atg tgt    1648
His Leu Cys Trp Cys Thr Asp Thr Ala Asp Ala Ala Leu Leu Met Cys
345                 350                 355
```

```
gag cat ccc gag tgg aag aac ttt gtg ctg gcg aca ggg gac agc gg gt    1697
Glu His Pro Glu Trp Lys Asn Phe Val Leu Ala Thr Gly Asp Ser Gly
360                 365                 370 atgtatctca tcctttggtg ccagaacaac atgtactgac ctggtttgcc tag g cac      1754
                                                              His
                                                              375 aca ttc aaa ctt ttg cca aat atc ggc aag cat gtg gtt gag ctt ctc      1802
Thr Phe Lys Leu Leu Pro Asn Ile Gly Lys His Val Val Glu Leu Leu
        380                 385                 390 gag ggt aca ctc gcg gag gat ctg gca cat gca tgg aga tgg cgg cct      1850
Glu Gly Thr Leu Ala Glu Asp Leu Ala His Ala Trp Arg Trp Arg Pro
395                 400                 405 ggt act ggc gat gcg ctg aaa tca aga aga gcg gca ccg gcg aag gat      1898
Gly Thr Gly Asp Ala Leu Lys Ser Arg Arg Ala Ala Pro Ala Lys Asp
410                 415                 420 tta gca gat atg cct ggc tgg aag cat gac gat gtt gtc aag tcc aag      1946
Leu Ala Asp Met Pro Gly Trp Lys His Asp Asp Val Val Lys Ser Lys
425                 430                 435 tta tag tgatggaaac tcgtcttgta gcgtgtctag gatagtaatc aaacgcgctc tc    2004
Leu
440 tgtcttaagc aacggagatt tgttgtgcta gacgggaaga gtaaggagta accacaaaat    2064 aagcaacttg aattagtcgt gttgaccgga accatggtgc attttgtttc tgaacttagg    2124 atttcaccga agatggccat gatggcagag aaagggaagt cgcacagggc agcttggtg     2184 cgactggtgc aggggaaaga atctgatc                                       2212

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
aargcyatya acgcyatygg                                                20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
acsacgtgct trccratgtt                                                20

<210> SEQ ID NO 4
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
cacacatcct cgtcatttcg ccatggcgcc ctcaagagca aac                      43

<210> SEQ ID NO 5
<211> LENGTH: 46
```

-continued

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
cacgctacaa gacgagtttc gagctctata acttggactt gacaac           46

<210> SEQ ID NO 6
<211> LENGTH: 202
<212> TYPE: DNA
<213> ORGANISM: Aerococcus viridans

<400> SEQUENCE: 6
aaaagttctt gatttataag ggtttctgga cttcttactg tactagtaca atttcgcccc    60
ttgtaccatt tttctgatac agaaacaata ttgtactgaa aaagggtat ttttggctaa   120 ttatggacct cacaaaggat atttgtggca attcattgga ataagctgtt ttaagtgcta   180
ttatttcaat tgtgatattt tt                                            202

<210> SEQ ID NO 7
<211> LENGTH: 61
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ctagaggaat aacaccatgg ccgtcgacgc tagcatgcat ggatcccggg taccgagctc    60
g                                                                   61

<210> SEQ ID NO 8
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
aattcgagct cggtacccgg gatccatgca gctagcgtcg acggccatgg tgttattcct    60

<210> SEQ ID NO 9
<211> LENGTH: 1323
<212> TYPE: DNA
<213> ORGANISM: Neocosmospora vasinfecta
<220> FEATURE:
<221> NAME/KEY: CDS
<222> LOCATION: (1)..(1323)

<400> SEQUENCE: 9 atg acc acc ccc cgc aaa gaa acc acc gtc ctc atc atc gga ggc ggc     48
Met Thr Thr Pro Arg Lys Glu Thr Thr Val Leu Ile Ile Gly Gly Gly
1               5                   10                  15 ggc aca atc ggc tcc tcc acc gcc cta cac ctc ctc cgc gca ggc tac     96
Gly Thr Ile Gly Ser Ser Thr Ala Leu His Leu Leu Arg Ala Gly Tyr
            20                  25                  30 acc ccc tcc aac atc acc gtc ctc gac acc tac ccc atc ccg tca gct    144
Thr Pro Ser Asn Ile Thr Val Leu Asp Thr Tyr Pro Ile Pro Ser Ala
        35                  40                  45 cag tcc gcc ggc aac gac cta aac aag atc atg ggc atc cgc ctg cgg    192
Gln Ser Ala Gly Asn Asp Leu Asn Lys Ile Met Gly Ile Arg Leu Arg
```

```
                50                  55                  60
aac aaa gtc gac ctg cag ctc agc ctg gaa gcg cgg gac atg tgg cgc    240
Asn Lys Val Asp Leu Gln Leu Ser Leu Glu Ala Arg Asp Met Trp Arg
 65                  70                  75                  80 aac gac gcg ctg ttc cgg ccc ttt ttc cac aat acg ggc cgg ctg gac    288
Asn Asp Ala Leu Phe Arg Pro Phe Phe His Asn Thr Gly Arg Leu Asp
 85                  90                  95 tgc gag agc agc gcg gag ggg gtg gag ggt ttg cgg agg gag tat cag    336
Cys Glu Ser Ser Ala Glu Gly Val Glu Gly Leu Arg Arg Glu Tyr Gln
100                 105                 110 aag ctg gtt gag gcg ggt gtg ggg ttg gag gag acg cat gag tgg ctt    384
Lys Leu Val Glu Ala Gly Val Gly Leu Glu Glu Thr His Glu Trp Leu
115                 120                 125 gat agt gag gag gcg att ttg gag aag gca ccg ttg ttg cag agg gag    432
Asp Ser Glu Glu Ala Ile Leu Glu Lys Ala Pro Leu Leu Gln Arg Glu
130                 135                 140 gag atc gag ggg tgg aag gcg att tgg agt gag gag ggg ggt tgg ttg    480
Glu Ile Glu Gly Trp Lys Ala Ile Trp Ser Glu Glu Gly Gly Trp Leu
145                 150                 155                 160 gct gct gct aag gcg att aac gcc atc ggg gag gag ttg cag cgg cag    528
Ala Ala Ala Lys Ala Ile Asn Ala Ile Gly Glu Glu Leu Gln Arg Gln
165                 170                 175 ggg gtt agg ttt ggg ttt ggg ggt gct ggg tcc ttc aag cgg cct ttg    576
Gly Val Arg Phe Gly Phe Gly Gly Ala Gly Ser Phe Lys Arg Pro Leu
180                 185                 190 ttt gct gat gat ggg aca act tgc atc ggt gtg gaa acg gtc gac ggg    624
Phe Ala Asp Asp Gly Thr Thr Cys Ile Gly Val Glu Thr Val Asp Gly
195                 200                 205 acc cag tac cat gcg gac aaa gtc gtc ctg gcc gct ggg gcg tgg agt    672
Thr Gln Tyr His Ala Asp Lys Val Val Leu Ala Ala Gly Ala Trp Ser
210                 215                 220 ccg gcc ctg gtc gac ctg gaa gag cag tgc tgc tcc aag gcg tgg gtg    720
Pro Ala Leu Val Asp Leu Glu Glu Gln Cys Cys Ser Lys Ala Trp Val
225                 230                 235                 240 tac gca cac atg cag ctg acc ccg gag gaa gcg gcc gta tac aag ggc    768
Tyr Ala His Met Gln Leu Thr Pro Glu Glu Ala Ala Val Tyr Lys Gly
245                 250                 255 tgt ccg gtt gtc tac cac ggc gat gtc ggc ttc ttc ttc gag ccg aac    816
Cys Pro Val Val Tyr His Gly Asp Val Gly Phe Phe Phe Glu Pro Asn
260                 265                 270 gag aac ggg gtg atc aaa gtc tgc gac gag ttc cct ggg ttc act cgg    864
Glu Asn Gly Val Ile Lys Val Cys Asp Glu Phe Pro Gly Phe Thr Arg
275                 280                 285 ttc aag cag cac cag ccg tac ggc gcg ccg gca ccg aag cct gtc tcg    912
Phe Lys Gln His Gln Pro Tyr Gly Ala Pro Ala Pro Lys Pro Val Ser
290                 295                 300 gtc ccg cgg tct cat gcc aaa cat ccc acc gac acg tac cca gac gcg    960
Val Pro Arg Ser His Ala Lys His Pro Thr Asp Thr Tyr Pro Asp Ala
305                 310                 315                 320 tct gag gag agc atc aag cga gct gtt tcg acg ttc ctg ccg aga ttc    1008
Ser Glu Glu Ser Ile Lys Arg Ala Val Ser Thr Phe Leu Pro Arg Phe
325                 330                 335 aag gac aag ccg ctg ttc aac cgg gcg ctg tgc tgg tgc acc gat aca    1056
Lys Asp Lys Pro Leu Phe Asn Arg Ala Leu Cys Trp Cys Thr Asp Thr
340                 345                 350 gcc gac tcg gcg ctg ctc atc tgt gag cat ccg aga tgg aag aac ttc    1104
Ala Asp Ser Ala Leu Leu Ile Cys Glu His Pro Arg Trp Lys Asn Phe
355                 360                 365 atc ctg gcc acg ggc gac agc ggg cac agt ttt aag ctg ttg ccc att    1152
Ile Leu Ala Thr Gly Asp Ser Gly His Ser Phe Lys Leu Leu Pro Ile
```

```
Ile Leu Ala Thr Gly Asp Ser Gly His Ser Phe Lys Leu Leu Pro Ile
370                 375                 380 att ggc aag cat gtt gtt gag ctg gtc gag ggc agg tta gct gat gat    1200
Ile Gly Lys His Val Val Glu Leu Val Glu Gly Arg Leu Ala Asp Asp
385                 390                 395                 400 ttg gct gag gcg tgg agg tgg cgg ccc ggt cag ggg gat gcg cgc aag    1248
Leu Ala Glu Ala Trp Arg Trp Arg Pro Gly Gln Gly Asp Ala Arg Lys
405                 410                 415 tcg atc cgt gct gcg ccg gca aag gat ctg gct gat atg ccc ggt tgg    1296
Ser Ile Arg Ala Ala Pro Ala Lys Asp Leu Ala Asp Met Pro Gly Trp
420                 425                 430 aag cac gat cag gac agc gag tca aga                                 1323
Lys His Asp Gln Asp Ser Glu Ser Arg
435                 440

<210> SEQ ID NO 10
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10 tttttcatg accacccccc gcaaagaaac caccgtcctc                          40

<210> SEQ ID NO 11
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
tttttgagct catcttgact cgctgtcctg atcgtgcttc                         40

<210> SEQ ID NO 12
<211> LENGTH: 18
<212> TYPE: PRT
<213> ORGANISM: Aeromonas hydrophila

<400> SEQUENCE: 12

Val Asp Ala Thr Gly Pro Gly Gly Asn Val Lys Thr Gly Lys Tyr Phe
1               5                   10                  15
Tyr Gly

<210> SEQ ID NO 13
<211> LENGTH: 10
<212> TYPE: PRT
<213> ORGANISM: Aeromonas hydrophila

<400> SEQUENCE: 13

Leu Asp Val Ala Ala His Glu Val Ser His
1               5                   10

<210> SEQ ID NO 14
<211> LENGTH: 6
<212> TYPE: PRT
<213> ORGANISM: Aeromonas hydrophila

<400> SEQUENCE: 14

Phe Gly Asp Gly Ala Thr
1               5
```

<210> SEQ ID NO 15
<211> LENGTH: 20
<212> TYPE: PRT
<213> ORGANISM: Lysobacter enzymogenes

<400> SEQUENCE: 15

Ala Leu Val Gly Thr Gly Pro Gly Gly Asn Gln Lys Thr Gly Gln Tyr
1               5                   10                  15

Glu Tyr Gly Thr
        20

<210> SEQ ID NO 16
<211> LENGTH: 8
<212> TYPE: PRT
<213> ORGANISM: Lysobacter enzymogenes
<220> FEATURE:
<221> NAME/KEY: MOD_RES
<222> LOCATION: (3)
<223> OTHER INFORMATION: variable amino acid

<400> SEQUENCE: 16

Tyr Ser Xaa Asn Tyr Glu Asn Ala
1               5

<210> SEQ ID NO 17
<211> LENGTH: 6
<212> TYPE: PRT
<213> ORGANISM: Lysobacter enzymogenes

<400> SEQUENCE: 17

Phe Gly Asp Gly Ala Thr
1               5

<210> SEQ ID NO 18
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
acaccatggc gccctcaaga gcaaacact                                    29

<210> SEQ ID NO 19
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
ttcgagctct ataacttgga cttgacaaca tcgtc                             35

<210> SEQ ID NO 20
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
cgactctaga ggaataacac catggcgccc tc                                32

```
<210> SEQ ID NO 21
<211> LENGTH: 58
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
gcttctagac tcaattggag atcgaccttg ttccgcaagc ggatacccat gaccttat        58

<210> SEQ ID NO 22
<211> LENGTH: 58
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
gcttctagac tcaattggag atcgaccttg ttccgcaagc ggatacccat aaacttat        58

<210> SEQ ID NO 23
<211> LENGTH: 58
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
gcttctagac tcaattggag atcgaccttg ttccgcaagc ggatacccat cagcttat        58

<210> SEQ ID NO 24
<211> LENGTH: 58
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
gcttctagac tcaattggag atcgaccttg ttccgcaagc ggatacccat catcttat        58

<210> SEQ ID NO 25
<211> LENGTH: 58
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
gcttctagac tcaattggag atcgaccttg ttccgcaagc ggatacccat ggtcttat        58

<210> SEQ ID NO 26
<211> LENGTH: 58
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
gcttctagac tcaattggag atcgaccttg ttccgcaagc ggatacccat cgccttat        58
```

```
<210> SEQ ID NO 27
<211> LENGTH: 58
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
gcttctagac tcaattggag atcgaccttg ttccgcaagc ggatacccat atacttat          58

<210> SEQ ID NO 28
<211> LENGTH: 58
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
gcttctagac tcaattggag atcgaccttg ttccgcaagc ggatacccat gttcttat          58

<210> SEQ ID NO 29
<211> LENGTH: 58
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
gcttctagac tcaattggag atcgaccttg ttccgcaagc ggatacccat gcacttat          58

<210> SEQ ID NO 30
<211> LENGTH: 58
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
gcttctagac tcaattggag atcgaccttg ttccgcaagc ggatacccat gctcttat          58

<210> SEQ ID NO 31
<211> LENGTH: 58
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
gcttctagac tcaattggag atcgaccttg ttccgcaagc ggatacccat ggccttat          58

<210> SEQ ID NO 32
<211> LENGTH: 440
<212> TYPE: PRT
<213> ORGANISM: Curvralia cravatae

<400> SEQUENCE: 32

Met Ala Pro Ser Arg Ala Asn Thr Ser Val Ile Val Gly Gly Gly
1               5                   10                  15

Gly Thr Ile Gly Ser Ser Thr Ala Leu His Leu Val Arg Ser Gly Tyr
            20                  25                  30
```

-continued

```
Thr Pro Ser Asn Ile Thr Val Leu Asp Thr Tyr Pro Ile Pro Ser Ala
         35                  40                  45
Gln Ser Ala Gly Asn Asp Leu Asn Lys Ile Met Gly Ile Arg Leu Arg
     50                  55                  60
Asn Lys Val Asp Leu Gln Leu Ser Leu Glu Ala Arg Gln Met Trp Arg
 65                  70                  75                  80
Glu Asp Asp Leu Phe Lys Glu Tyr Phe His Asn Thr Gly Arg Leu Asp
                 85                  90                  95
Cys Ala His Gly Glu Glu Gly Leu Ala Asp Leu Arg Gln Ala Tyr Gln
            100                 105                 110
Ala Leu Leu Asp Ala Asn Ala Gly Leu Glu Glu Thr Thr Glu Trp Leu
        115                 120                 125
Asp Ser Glu Asp Glu Ile Leu Lys Lys Met Pro Leu Leu Asp Arg Glu
    130                 135                 140
Gln Ile Lys Gly Trp Lys Ala Val Tyr Ser Gln Asp Gly Gly Trp Leu
145                 150                 155                 160
Ala Ala Ala Lys Ala Ile Asn Ala Ile Gly Glu Tyr Leu Arg Asp Gln
                165                 170                 175
Gly Val Lys Phe Gly Phe Gly Ala Gly Ser Phe Lys Gln Pro Leu
            180                 185                 190
Leu Ala Glu Gly Val Cys Ile Gly Val Glu Thr Val Asp Gly Thr Arg
        195                 200                 205
Tyr Tyr Ala Asp Lys Val Val Leu Ala Ala Gly Ala Trp Ser Pro Val
    210                 215                 220
Leu Val Asp Leu Glu Asp Gln Cys Val Ser Lys Ala Trp Val Tyr Ala
225                 230                 235                 240
His Ile Gln Leu Thr Pro Glu Glu Ala Glu Tyr Lys Asn Val Pro
                245                 250                 255
Val Val Tyr Asn Gly Asp Val Gly Phe Phe Phe Glu Pro Asp Glu His
            260                 265                 270
Gly Val Ile Lys Val Cys Asp Glu Phe Pro Gly Phe Thr Arg Phe Lys
        275                 280                 285
Gln His Gln Pro Tyr Gly Ala Lys Ala Pro Lys Arg Ile Ser Val Pro
    290                 295                 300
Arg Ser Ala Ala Lys His Pro Thr Asp Thr Tyr Pro Asp Ala Ser Glu
305                 310                 315                 320
Lys Ser Ile Arg Lys Ala Ile Ala Thr Phe Leu Pro Lys Phe Thr Glu
                325                 330                 335
Lys Glu Leu Phe Asn Arg His Leu Cys Trp Cys Thr Asp Thr Ala Asp
            340                 345                 350
Ala Ala Leu Leu Met Cys Glu His Pro Glu Trp Lys Asn Phe Val Leu
        355                 360                 365
Ala Thr Gly Asp Ser Gly His Thr Phe Lys Leu Leu Pro Asn Ile Gly
    370                 375                 380
Lys His Val Val Glu Leu Leu Glu Gly Thr Leu Ala Glu Asp Leu Ala
385                 390                 395                 400
His Ala Trp Arg Trp Arg Pro Gly Thr Gly Asp Ala Leu Lys Ser Arg
                405                 410                 415
Arg Ala Ala Pro Ala Lys Asp Leu Ala Asp Met Pro Gly Trp Lys His
            420                 425                 430
Asp Asp Val Val Lys Ser Lys Leu
        435                 440
```

<210> SEQ ID NO 33
<211> LENGTH: 441
<212> TYPE: PRT
<213> ORGANISM: Neocosmospora vasinfecta

<400> SEQUENCE: 33

```
Met Thr Thr Pro Arg Lys Glu Thr Val Leu Ile Ile Gly Gly
1               5                   10                  15

Gly Thr Ile Gly Ser Ser Thr Ala Leu His Leu Leu Arg Ala Gly Tyr
            20                  25                  30

Thr Pro Ser Asn Ile Thr Val Leu Asp Thr Tyr Pro Ile Pro Ser Ala
        35                  40                  45

Gln Ser Ala Gly Asn Asp Leu Asn Lys Ile Met Gly Ile Arg Leu Arg
    50                  55                  60

Asn Lys Val Asp Leu Gln Leu Ser Leu Glu Ala Arg Asp Met Trp Arg
65                  70                  75                  80

Asn Asp Ala Leu Phe Arg Pro Phe Phe His Asn Thr Gly Arg Leu Asp
                85                  90                  95

Cys Glu Ser Ser Ala Glu Gly Val Glu Gly Leu Arg Arg Glu Tyr Gln
            100                 105                 110

Lys Leu Val Glu Ala Gly Val Gly Leu Glu Glu Thr His Glu Trp Leu
        115                 120                 125

Asp Ser Glu Glu Ala Ile Leu Gly Lys Ala Pro Leu Leu Gln Arg Glu
    130                 135                 140

Glu Ile Glu Gly Trp Lys Ala Ile Trp Ser Glu Gly Gly Trp Leu
145                 150                 155                 160

Ala Ala Ala Lys Ala Ile Asn Ala Ile Gly Glu Glu Leu Gln Arg Gln
                165                 170                 175

Gly Val Arg Phe Gly Phe Gly Gly Ala Gly Ser Phe Lys Arg Pro Leu
            180                 185                 190

Phe Ala Asp Asp Gly Thr Thr Cys Ile Gly Val Glu Thr Val Asp Gly
        195                 200                 205

Thr Gln Tyr His Ala Asp Lys Val Val Leu Ala Ala Gly Ala Trp Ser
    210                 215                 220

Pro Ala Leu Val Asp Leu Glu Glu Gln Cys Cys Ser Lys Ala Trp Val
225                 230                 235                 240

Tyr Ala His Met Gln Leu Thr Pro Glu Glu Ala Ala Val Tyr Lys Gly
                245                 250                 255

Cys Pro Val Val Tyr His Gly Asp Val Gly Phe Phe Phe Glu Pro Asn
            260                 265                 270

Glu Asn Gly Val Ile Lys Val Cys Asp Glu Phe Pro Gly Phe Thr Arg
        275                 280                 285

Phe Lys Gln His Gln Pro Tyr Gly Ala Pro Ala Pro Lys Pro Val Ser
    290                 295                 300

Val Pro Arg Ser His Ala Lys His Pro Thr Asp Thr Tyr Pro Asp Ala
305                 310                 315                 320

Ser Glu Glu Ser Ile Lys Arg Ala Val Ser Thr Phe Leu Pro Arg Phe
                325                 330                 335

Lys Asp Lys Pro Leu Phe Asn Arg Ala Leu Cys Trp Cys Thr Asp Thr
            340                 345                 350

Ala Asp Ser Ala Leu Leu Ile Cys Glu His Pro Arg Trp Lys Asn Phe
        355                 360                 365

Ile Leu Ala Thr Gly Asp Ser Gly His Ser Phe Lys Leu Leu Pro Ile
    370                 375                 380
```

```
Ile Gly Lys His Val Val Glu Leu Val Glu Gly Arg Leu Ala Asp Asp
385                 390                 395                 400

Leu Ala Glu Ala Trp Arg Trp Arg Pro Gly Gln Gly Asp Ala Arg Lys
                405                 410                 415

Ser Ile Arg Ala Ala Pro Ala Lys Asp Leu Ala Asp Met Pro Gly Trp
            420                 425                 430

Lys His Asp Gln Asp Ser Glu Ser Arg
        435                 440

<210> SEQ ID NO 34
<211> LENGTH: 437
<212> TYPE: PRT
<213> ORGANISM: Coniochaeta sp.

<400> SEQUENCE: 34

Met Thr Ser Asn Arg Ala Asp Thr Arg Val Ile Val Gly Gly Gly
1               5                   10                  15

Gly Thr Ile Gly Ser Ser Thr Ala Leu His Leu Val Arg Ser Gly Tyr
                20                  25                  30

Ala Pro Ala Asn Ile Thr Val Leu Asp Thr Phe Glu Ile Pro Ser Ala
            35                  40                  45

Gln Ser Ala Gly His Asp Leu Asn Lys Ile Met Gly Ile Arg Leu Arg
    50                  55                  60

Asn Lys Val Asp Leu Gln Met Ser Leu Glu Ala Arg Gln Met Trp Lys
65                  70                  75                  80

Glu Asp Glu Leu Phe Gln Pro Phe Phe His Asn Thr Gly Arg Met Asp
                85                  90                  95

Cys Glu His Thr Pro Glu Gly Ile Glu Asp Leu Lys Lys Gln Tyr Gln
            100                 105                 110

Ala Leu His Asp Ala Gly Ala Gly Leu Glu Lys Thr His Ala Trp Leu
        115                 120                 125

Asp Asn Glu Asp Glu Ile Leu Ser Lys Met Pro Leu Leu Gln Arg Asp
130                 135                 140

Gln Ile Gln Gly Trp Lys Ala Ile Trp Ser Gln Asp Gly Gly Trp Leu
145                 150                 155                 160

Ala Ala Ala Lys Ala Ile Asn Ala Ile Gly Gln Phe Leu Lys Glu Arg
                165                 170                 175

Gly Val Lys Phe Gly Phe Gly Ala Gly Ser Phe Lys Gln Pro Leu
            180                 185                 190

Phe Asp Asp Glu Gly Thr Thr Cys Ile Gly Val Glu Thr Ala Asp Gly
        195                 200                 205

Thr Lys Tyr Tyr Ala Asp Lys Val Val Leu Ala Ala Gly Ala Trp Ser
210                 215                 220

Pro Thr Leu Val Asp Leu Glu Asp Gln Cys Cys Ser Lys Ala Trp Val
225                 230                 235                 240

Tyr Ala His Ile Gln Leu Thr Pro Glu Glu Ala Glu Tyr Lys Gly
                245                 250                 255

Val Pro Val Val Tyr Asn Gly Glu Phe Gly Phe Phe Glu Pro Asn
            260                 265                 270

Glu Phe Gly Val Ile Lys Val Cys Asp Glu Phe Pro Gly Phe Ser Arg
        275                 280                 285

Phe Lys Glu His Gln Pro Tyr Gly Ala Pro Ser Pro Lys His Ile Ser
    290                 295                 300

Val Pro Arg Ser His Ala Lys His Pro Thr Asp Thr Tyr Pro Asp Ala
305                 310                 315                 320
```

Ser Glu Val Ser Ile Lys Lys Ala Ile Ala Thr Phe Leu Pro Arg Phe
            325                 330                 335

Gln Asp Lys Glu Leu Phe Asn Arg Ala Leu Cys Trp Cys Thr Asp Thr
            340                 345                 350

Ala Asp Ala Ala Leu Leu Met Cys Glu His Pro Lys Trp Lys Asn Phe
            355                 360                 365

Ile Leu Ala Thr Gly Asp Ser Gly His Ser Phe Lys Ile Leu Pro Asn
            370                 375                 380

Val Gly Lys His Val Val Glu Leu Ile Glu Gly Arg Leu Pro Glu Glu
385                 390                 395                 400

Met Ala Tyr Gln Trp Arg Trp Arg Pro Gly Gly Asp Ala Leu Lys Ser
            405                 410                 415

Arg Arg Ala Ala Pro Pro Lys Asp Leu Ala Asp Met Pro Gly Trp Lys
            420                 425                 430

His Asp Pro Lys Leu
            435

<210> SEQ ID NO 35
<211> LENGTH: 437
<212> TYPE: PRT
<213> ORGANISM: Eupenicillium terrenum

<400> SEQUENCE: 35

Met Ala His Ser Arg Ala Ser Thr Lys Val Val Val Gly Gly Gly Gly
1               5                   10                  15

Gly Thr Ile Gly Ser Ser Thr Ala Leu His Leu Ile Arg Ser Gly Tyr
            20                  25                  30

Thr Pro Ser Asn Ile Thr Val Leu Asp Val Tyr Lys Thr Pro Ser Leu
            35                  40                  45

Gln Ser Ala Gly His Asp Leu Asn Lys Ile Met Gly Ile Arg Leu Arg
        50                  55                  60

Asn Gly Pro Asp Leu Gln Leu Ser Leu Glu Ser Leu Asp Met Trp Gln
65                  70                  75                  80

Asn Asp Glu Leu Phe Lys Pro Phe His Gln Val Gly Met Ile Asp
            85                  90                  95

Cys Ser Ser Lys Glu Gly Ile Glu Asn Leu Arg Arg Lys Tyr Gln
            100                 105                 110

Thr Leu Leu Asp Ala Gly Ile Gly Leu Glu Lys Thr Asn Val Trp Leu
            115                 120                 125

Glu Ser Glu Asp Glu Ile Leu Ala Lys Ala Pro Asn Phe Thr Arg Glu
        130                 135                 140

Gln Val Lys Gly Trp Lys Gly Leu Phe Cys Thr Asp Gly Gly Trp Leu
145                 150                 155                 160

Ala Ala Ala Lys Ala Ile Asn Ala Ile Gly Ile Phe Leu Gln Asp Lys
            165                 170                 175

Gly Val Lys Phe Gly Phe Gly Ala Gly Thr Phe Gln Gln Pro Leu
            180                 185                 190

Phe Ala Ala Asp Gly Lys Thr Cys Ile Gly Leu Glu Thr Thr Asp Gly
            195                 200                 205

Thr Lys Tyr Phe Ala Asp Lys Val Val Leu Ala Ala Gly Ala Trp Ser
        210                 215                 220

Pro Thr Leu Val Asp Leu Glu Asp Gln Cys Val Ser Lys Ala Trp Val
225                 230                 235                 240

Phe Ala His Ile Gln Leu Thr Pro Lys Glu Ala Asp Ala Tyr Lys Asn

-continued

```
                  245                 250                 255
Val Pro Val Val Tyr Asp Gly Glu Tyr Gly Phe Phe Glu Pro Asn
            260                 265                 270

Glu Tyr Gly Val Ile Lys Val Cys Asp Glu Phe Pro Gly Phe Ser Arg
            275                 280                 285

Phe Lys Leu His Gln Pro Tyr Gly Ala Ala Ser Pro Lys Met Ile Ser
            290                 295                 300

Val Pro Arg Ser His Ala Lys His Pro Thr Asp Thr Tyr Pro Asp Ala
305                 310                 315                 320

Ser Glu Val Thr Ile Arg Lys Ala Ile Ala Arg Phe Leu Pro Glu Phe
                325                 330                 335

Lys Asp Lys Glu Leu Phe Asn Arg Thr Met Cys Trp Cys Thr Asp Thr
                340                 345                 350

Ala Asp Ala Asn Leu Leu Ile Cys Glu His Pro Lys Trp Lys Asn Phe
                355                 360                 365

Ile Leu Ala Thr Gly Asp Ser Gly His Ser Phe Lys Leu Leu Pro Asn
370                 375                 380

Ile Gly Lys His Val Val Glu Leu Leu Glu Gly Ser Leu Ser Gln Glu
385                 390                 395                 400

Met Ala Gly Ala Trp Arg Trp Arg Pro Gly Gly Asp Ala Leu Arg Ser
                405                 410                 415

Arg Arg Gly Ala Pro Ala Lys Asp Leu Ala Glu Met Pro Gly Trp Lys
                420                 425                 430

His Asp Ala His Leu
            435
```

<210> SEQ ID NO 36
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Val His Leu Thr Pro
1               5

<210> SEQ ID NO 37
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Val His Leu Thr
1

<210> SEQ ID NO 38
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
gccaaaagag gctgcttgaa cgat                                              24

<210> SEQ ID NO 39
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
gcatccagca ccaccaaaac aaac                                          24

<210> SEQ ID NO 40
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
tggtgccaga caacatgta ctgacc                                         26

<210> SEQ ID NO 41
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
acctggtttg cctaggcaca ca                                            22

<210> SEQ ID NO 42
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
caaagagtat ttccacaaca ctggaagact cgactgtgca catggggaag agg          53

<210> SEQ ID NO 43
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
cctcttcccc atgtgcacag tcgagtcttc cagtgttgtg gaaatactct ttg          53

<210> SEQ ID NO 44
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
gacctggaag atcaatgcgt ttcaaaagct tgggtatatg ctcacataca gcttac       56

```
<210> SEQ ID NO 45
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
gtaagctgta tgtgagcata tacccaagct tttgaaacgc attgatcttc caggtc        56

<210> SEQ ID NO 46
<211> LENGTH: 55
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
ctttgtgctg gcgacagggg acagcgggca cacattcaaa cttttgccaa atatc         55

<210> SEQ ID NO 47
<211> LENGTH: 55
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
gatatttggc aaaagtttga atgtgtgccc gctgtcccct gtcgccagca caaag         55

<210> SEQ ID NO 48
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Val Asn Ala Thr Gly Pro Gly Gly Asn Val Lys Thr Gly Lys Tyr Phe
1               5                   10                  15

Tyr Gly

<210> SEQ ID NO 49
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Ala Leu Val Gly Thr Gly Pro Gly Gly Asn Gln Lys Thr Gly Gln Tyr
1               5                   10                  15

Glu Tyr Gly Thr
20

<210> SEQ ID NO 50
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 50

Val Leu Ser Pro Ala
1               5
```